(12) United States Patent
Fabian et al.

(10) Patent No.: US 10,716,684 B2
(45) Date of Patent: Jul. 21, 2020

(54) SPINE SURGERY METHOD AND INSTRUMENTATION

(71) Applicants: Henry F. Fabian, Steamboat Springs, CO (US); Jeff Arnett, Steamboat Springs, CO (US)

(72) Inventors: Henry F. Fabian, Steamboat Springs, CO (US); Jeff Arnett, Steamboat Springs, CO (US)

(73) Assignee: Vertebration, Inc., Powell, OH (US)

( * ) Notice: Subject to any disclaimer, the term of this patent is extended or adjusted under 35 U.S.C. 154(b) by 201 days.

(21) Appl. No.: 16/008,297

(22) Filed: Jun. 14, 2018

(65) Prior Publication Data

US 2018/0360617 A1    Dec. 20, 2018

Related U.S. Application Data

(60) Provisional application No. 62/519,448, filed on Jun. 14, 2017.

(51) Int. Cl.
| | | |
|---|---|---|
| *A61F 2/44* | (2006.01) | |
| *A61F 2/46* | (2006.01) | |
| *A61B 17/70* | (2006.01) | |
| *A61F 2/30* | (2006.01) | |
| *A61B 90/00* | (2016.01) | |

(52) U.S. Cl.
CPC .......... *A61F 2/4611* (2013.01); *A61F 2/4425* (2013.01); *A61F 2/4455* (2013.01); *A61F 2/4684* (2013.01); *A61B 17/7074* (2013.01); *A61B 2090/062* (2016.02); *A61F 2002/3071* (2013.01); *A61F 2002/30179* (2013.01); *A61F 2002/30471* (2013.01); *A61F 2002/30492* (2013.01); *A61F 2002/30505* (2013.01); *A61F 2002/30579* (2013.01); *A61F 2002/30617* (2013.01); *A61F 2002/30904* (2013.01); *A61F 2002/443* (2013.01); *A61F 2002/4619* (2013.01); *A61F 2002/4627* (2013.01); *A61F 2002/4628* (2013.01); *A61F 2002/4662* (2013.01)

(58) Field of Classification Search
CPC ..... A61F 2/4611; A61F 2/4425; A61F 2/4455
See application file for complete search history.

(56) References Cited

U.S. PATENT DOCUMENTS

| | | | | |
|---|---|---|---|---|
| 2004/0225295 | A1* | 11/2004 | Zubok | A61F 2/442 606/90 |
| 2008/0287957 | A1* | 11/2008 | Hester | A61B 17/025 606/99 |
| 2013/0030535 | A1* | 1/2013 | Foley | A61B 17/1671 623/17.16 |
| 2013/0268077 | A1* | 10/2013 | You | A61F 2/4455 623/17.16 |
| 2014/0163684 | A1* | 6/2014 | Donner | A61B 17/7056 623/17.16 |
| 2020/0054459 | A1* | 2/2020 | Smith | A61F 2/4611 |

* cited by examiner

*Primary Examiner* — Christian A Sevilla
(74) *Attorney, Agent, or Firm* — Timothy D. Bennett; Emerson Thomson Bennett

(57) ABSTRACT

Surgical instrumentation may be used to insert a spinal implant into a vertebral space while in a contracted condition and then deploy the spinal implant into an expanded condition.

20 Claims, 57 Drawing Sheets

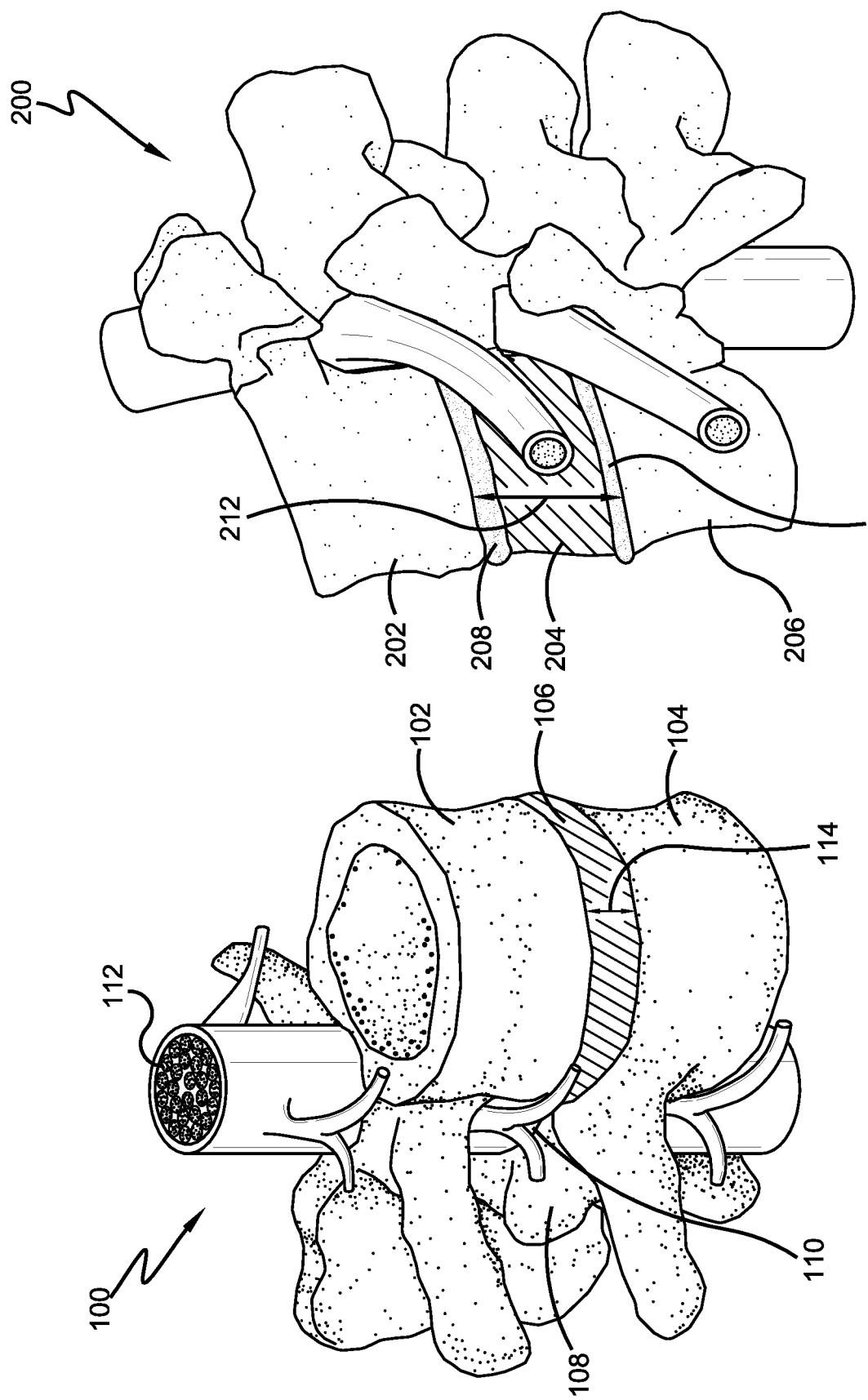

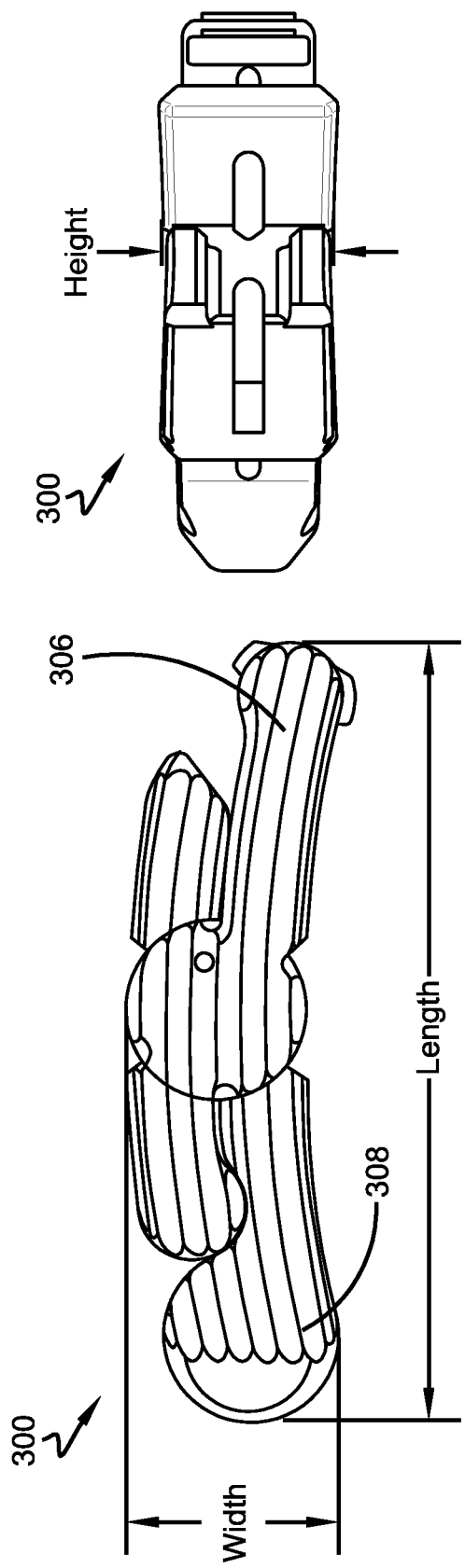
FIG. 7
FIG. 8
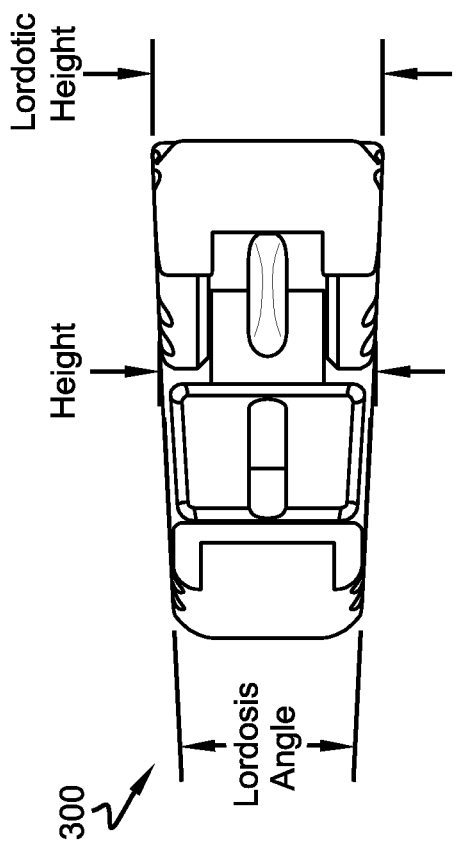
FIG. 9

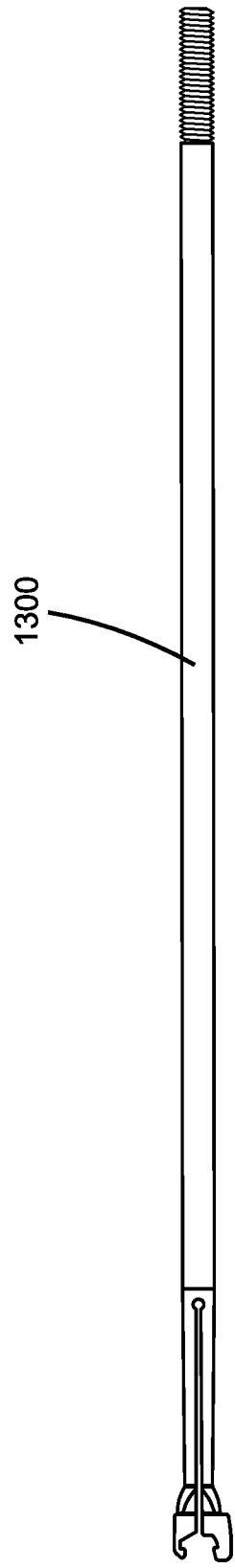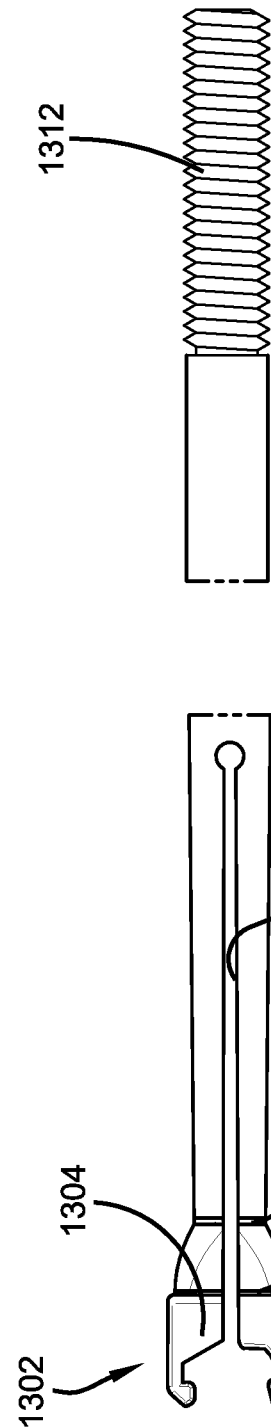
FIG. 39
FIG. 40
FIG. 41

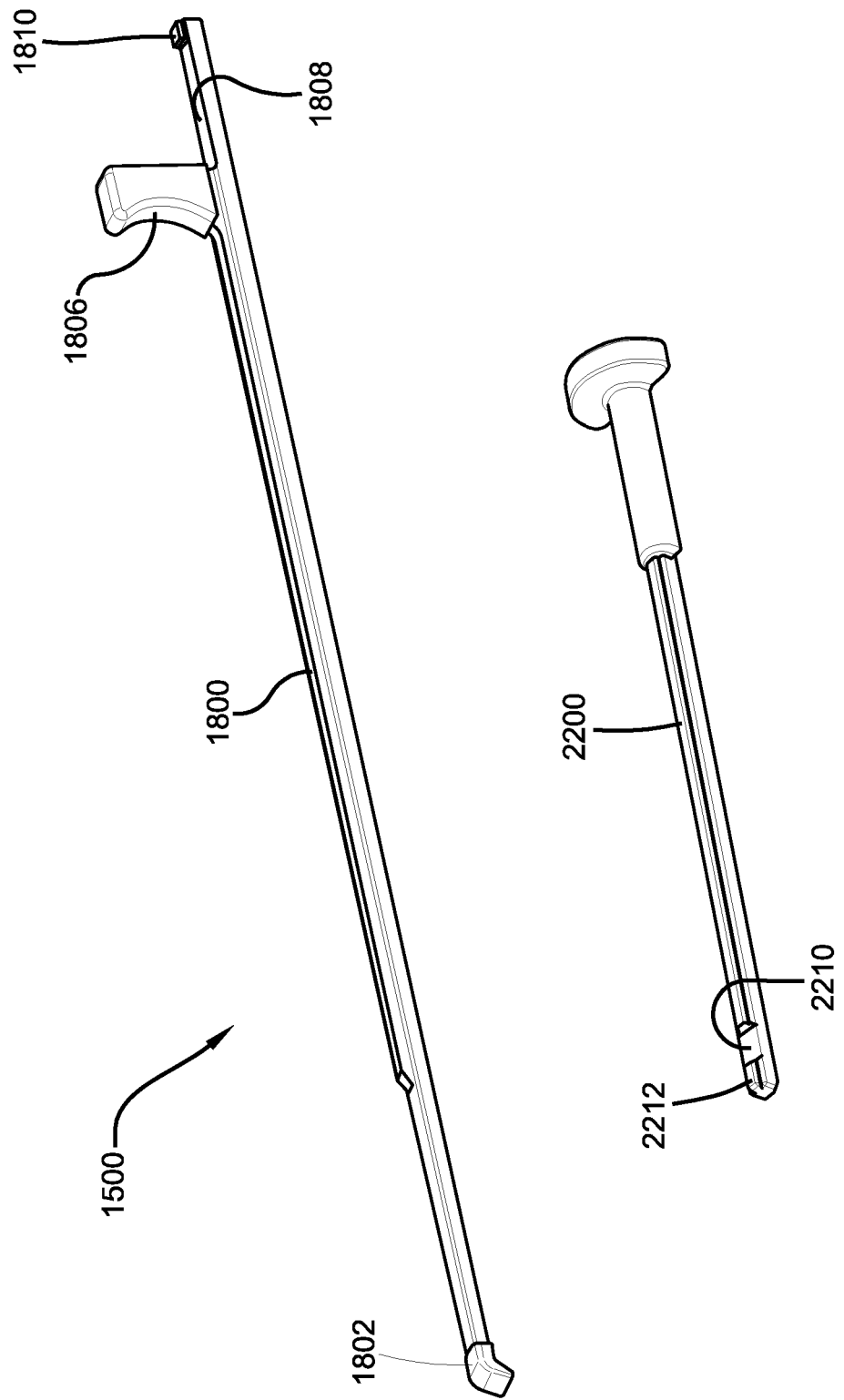

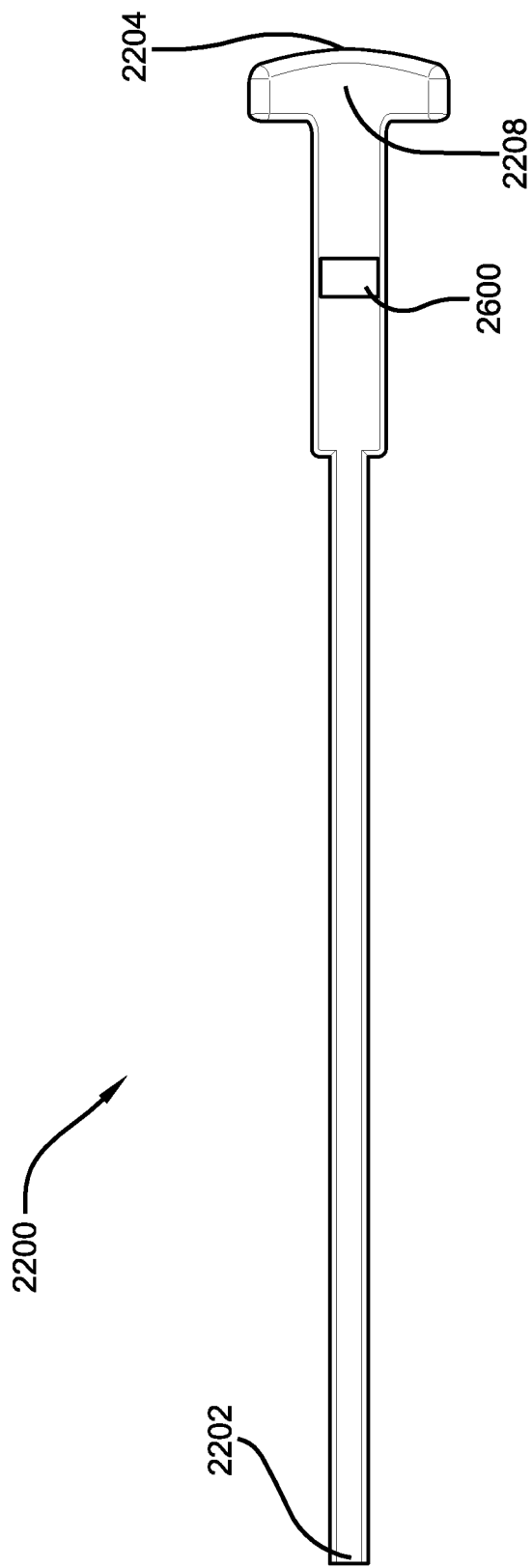

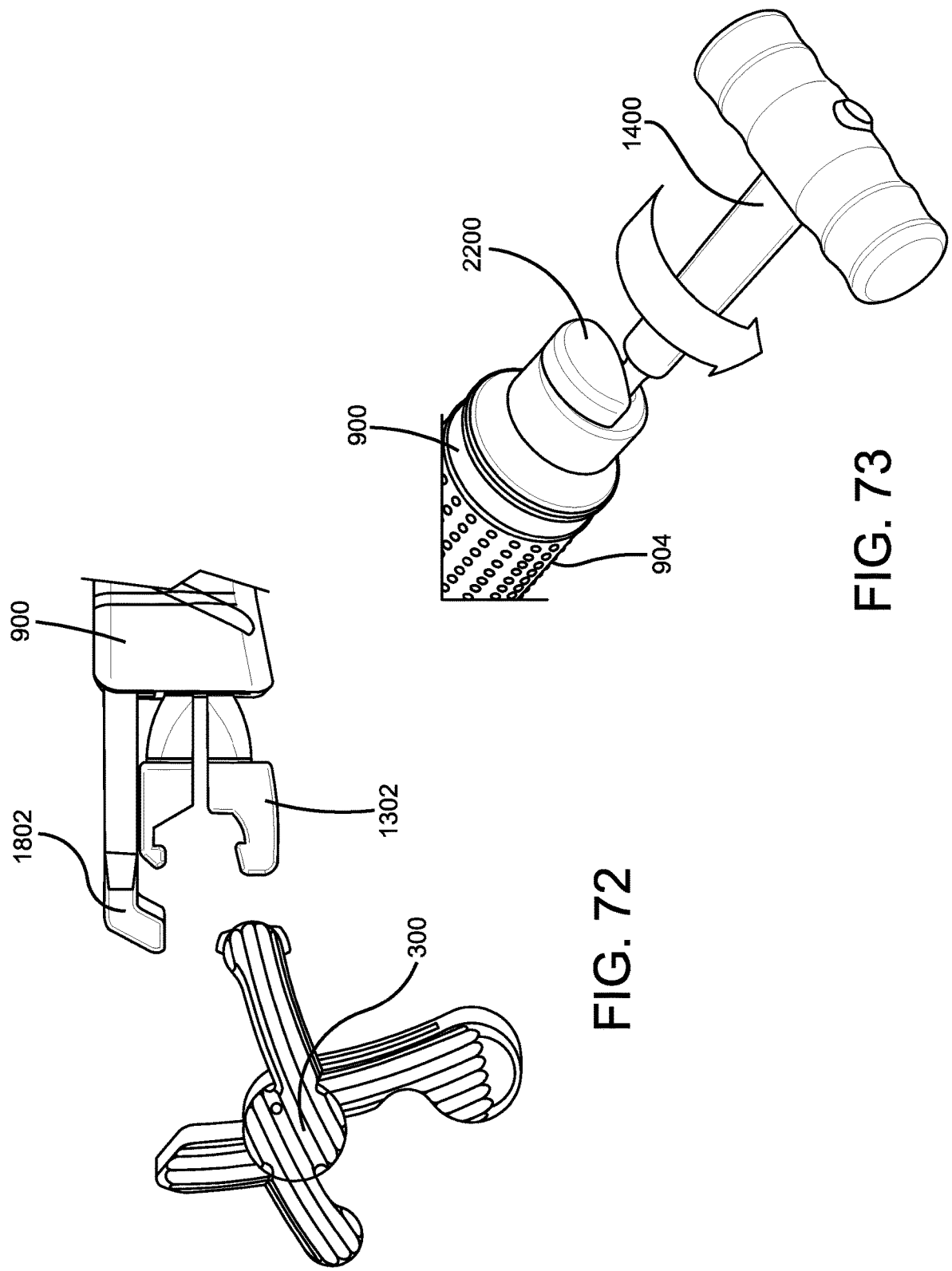

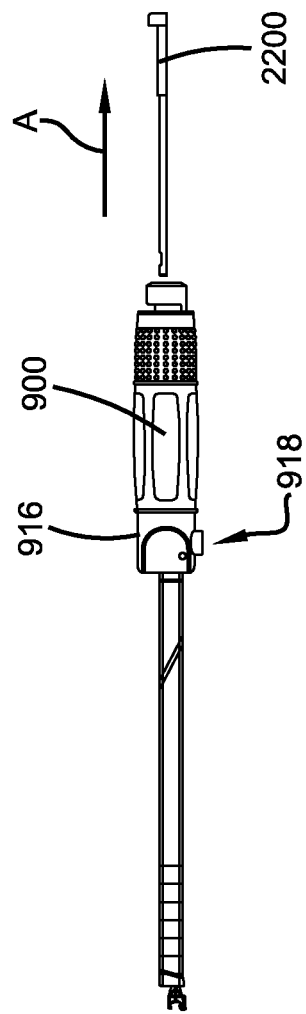
FIG. 74
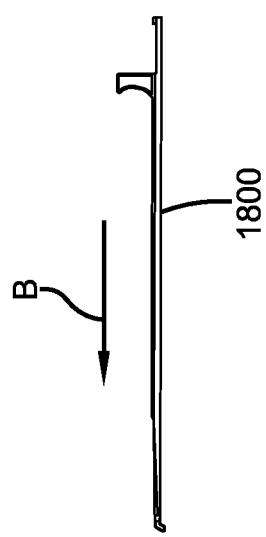
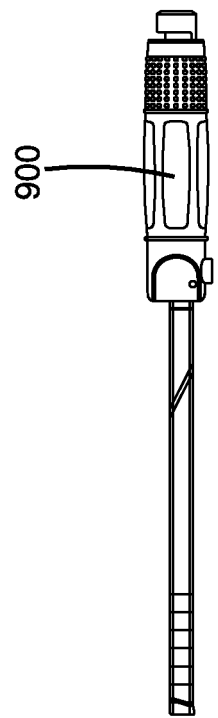
FIG. 75
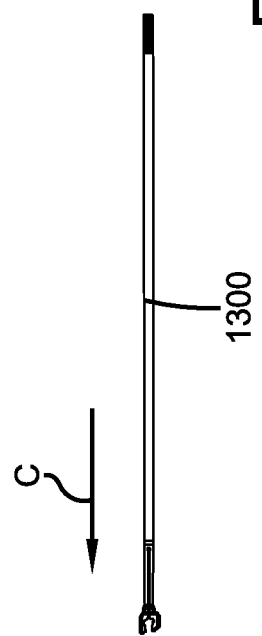

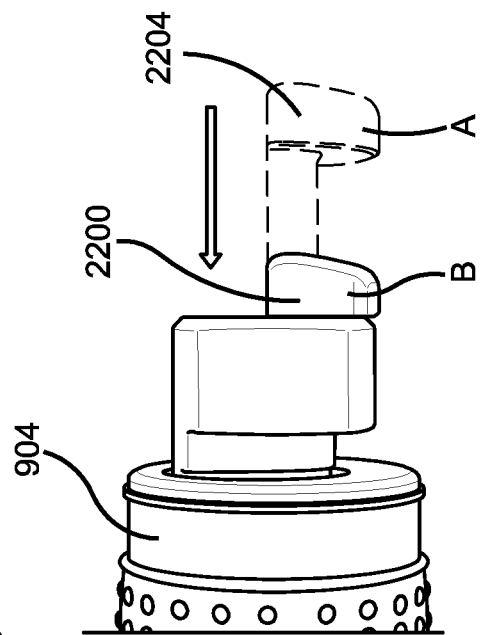
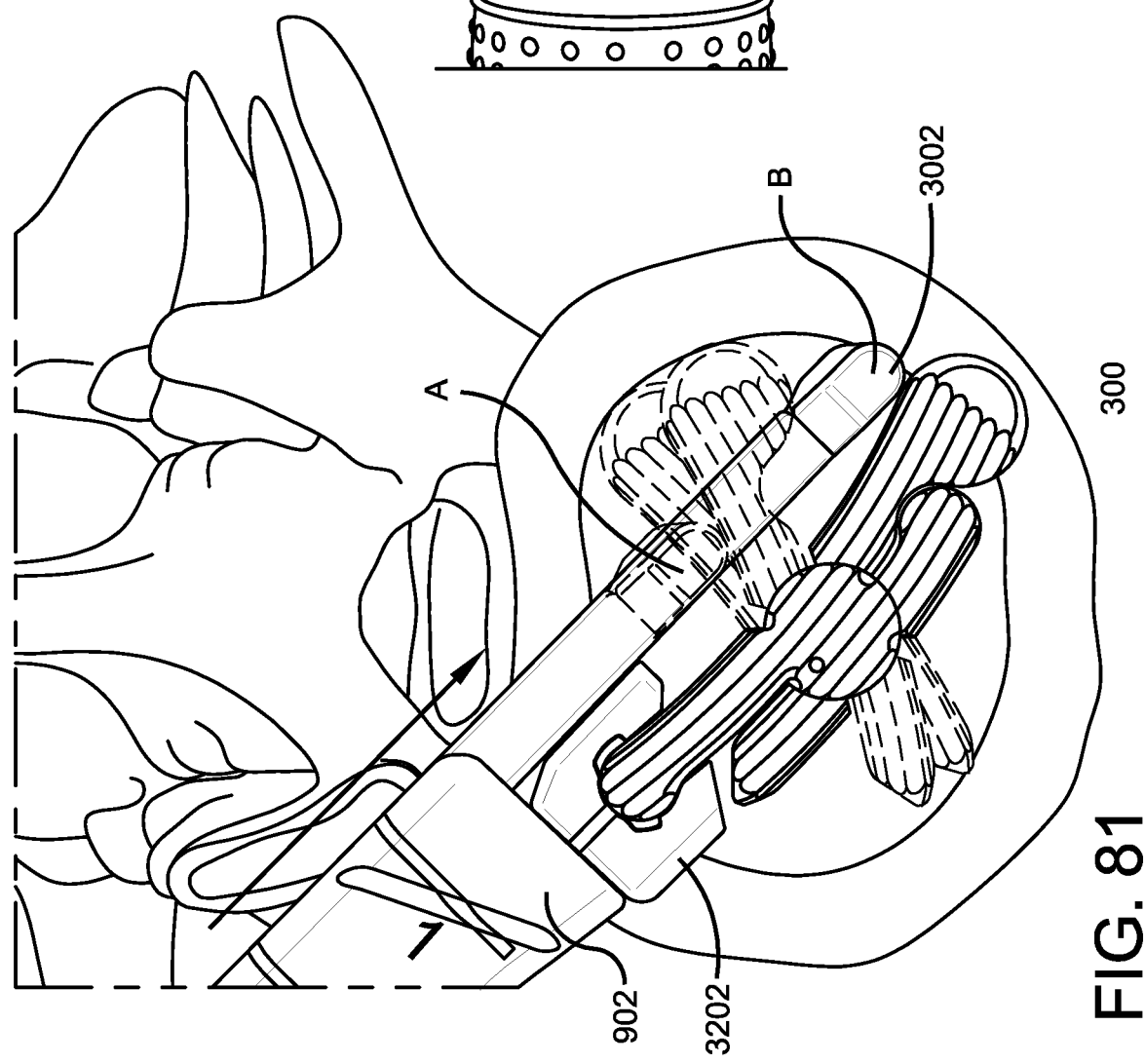
FIG. 82
FIG. 81

SPINE SURGERY METHOD AND INSTRUMENTATION

This application claims priority to U.S. Provisional Patent Application No. 62/519,448 entitled "SPINE SURGERY METHOD AND INSTRUMENTATION" filed on Jun. 14, 2017, the contents of which are incorporated herein.

I. BACKGROUND OF THE INVENTION

A. Field of Invention

This invention pertains to the art of methods and apparatuses regarding spine surgery and more specifically relates to surgical procedures, a spinal implant and surgical instrumentation used to position the spinal implant and to deploy the implant within a vertebral space.

B. Description of the Related Art

The volume of spinal surgeries to treat degenerative disc and facet disease has steadily increased over the past decades, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have limitations. One limitation is that the physical components are relatively large and bulky. This reduces surgeon visualization of the surgical site. Another limitation of known spinal surgical methods is that known surgical tools and implants are cumbersome and difficult to maneuver within the limited surgical space available. The limitations of current instrumentation in MIS spine surgery are noted particularly with regards to interbody fusion surgery.

The present invention provides methods and apparatuses for overcoming these limitations by providing surgical procedures, a spinal implant and surgical instrumentation used to position the spinal implant within a vertebral space while in a contracted or non-deployed condition and then adjust the spinal implant into an expanded or deployed condition while in the vertebral space.

II. SUMMARY OF THE INVENTION

According to some embodiments of this invention surgical instrumentation may be used with an associated vertebral space comprising a first vertebral body having a first endplate; and, a second vertebral body adjacent the first vertebral body having a second endplate. The surgical instrumentation may also be used with an associated spinal implant having first and second contact surfaces designed to contact the first and second endplates, respectively; a first member; and, a second member that is movable with respect to the first member to deploy the spinal implant. The surgical instrumentation may comprise: an inserter comprising: a proximal end; a distal end; a longitudinal length; a first longitudinally extending channel that extends for at least most of the longitudinal length; and, a second distinct longitudinally extending channel that extends for at least most of the longitudinal length; an implant gripping mechanism comprising: (1) a gripping device having: a proximal end; a distal end; and, a gripper positioned at the distal end of the gripping device; and, (2) a tool; and, an implant deployment mechanism comprising: (1) an inserter tamp having: a proximal end; and, a distal end; and, (2) an impactor. The implant gripping mechanism may be operable to: (1) position at least a portion of the gripping device within the first longitudinally extending channel; and, (2) access the proximal end of the gripping device through the proximal end of the first longitudinally extending channel with the tool to adjust the gripper to grip the associated spinal implant with the spinal implant juxtaposed to the distal end of the first longitudinally extending channel. The implant deployment mechanism may be operable to: (1) position at least a portion of the inserter tamp within the second longitudinally extending channel; and, (2) access the proximal end of the inserter tamp through the proximal end of the second longitudinally extending channel with the impactor to adjust the distal end of the inserter tamp to deploy the associated spinal implant while the gripper grips the associated spinal implant within the associated vertebral space.

According to other embodiments of this invention a method for use with an associated vertebral space comprising a first vertebral body having a first endplate and a second vertebral body adjacent the first vertebral body having a second endplate may comprise the steps of: (A) providing a spinal implant having first and second contact surfaces designed to contact the first and second endplates, respectively; a first member; and, a second member that is movable with respect to the first member to deploy the spinal implant; (B) providing surgical instrumentation comprising: (1) an inserter comprising: a proximal end; a distal end; a longitudinal length; a first longitudinally extending channel that extends for at least most of the longitudinal length; and, a second distinct longitudinally extending channel that extends for at least most of the longitudinal length; (2) an implant gripping mechanism comprising: (a) a gripping device having: a proximal end; a distal end; and, a gripper positioned at the distal end of the gripping device; and, (b) a tool; and, (3) an implant deployment mechanism comprising: (a) an inserter tamp having: a proximal end; and, a distal end; and, (b) an impactor; (C) providing the surgical instrumentation to be operable to: (1) position at least a portion of the gripping device within the first longitudinally extending channel; (2) access the proximal end of the gripping device through the proximal end of the first longitudinally extending channel with the tool to adjust the gripper to grip the spinal implant with the spinal implant juxtaposed to the distal end of the first longitudinally extending channel; (3) position at least a portion of the inserter tamp within the second longitudinally extending channel; and, (4) access the proximal end of the inserter tamp through the proximal end of the second longitudinally extending channel with the impactor to adjust the distal end of the inserter tamp to deploy the spinal implant while the gripper grips the spinal implant within the associated vertebral space.

Benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 1 is a side perspective view of a spinal segment showing a vertebral space defined by the intradiscal space usually occupied by a disc between two adjacent vertebral bodies.

FIG. 2 is a side perspective view of a spinal segment showing a vertebral space defined by the space usually occupied by a vertebral body and its two adjacent discs.

FIG. 7 is a top view of a spinal implant in a contracted condition.

FIG. 8 is a side view of the spinal implant shown in FIG. 7.

FIG. 9 is a side view of a deployed spinal implant.

FIG. 39 is a side view of a gripping device.

FIG. 40 is a close-up view of the distal end of the gripping device shown in FIG. 39.

FIG. 41 is a close-up view of the proximal end of the gripping device shown in FIG. 39.

FIG. 46 shows an implant deployment mechanism.

FIG. 50 is a side view of an impactor.

FIG. 72 is a top view of a gripper that has released a spinal implant.

FIG. 73 is a perspective view of the proximal end of an inserter illustrating a tool being rotated to release a spinal implant.

FIG. 74 is a side view illustrating how an inserter tamp and impactor can be removed from an inserter.

FIG. 75 is a side view illustrating how a gripping device can be removed from an inserter.

FIG. 81 illustrates a remover tamp being extended to adjust a spinal implant from a deployed condition into a collapsed condition within a vertebral space.

FIG. 82 is a side view of the proximal end of an inserter showing the impactor being moved to adjust the spinal implant into a collapsed condition.

IV. DETAILED DESCRIPTION

Figure 4:
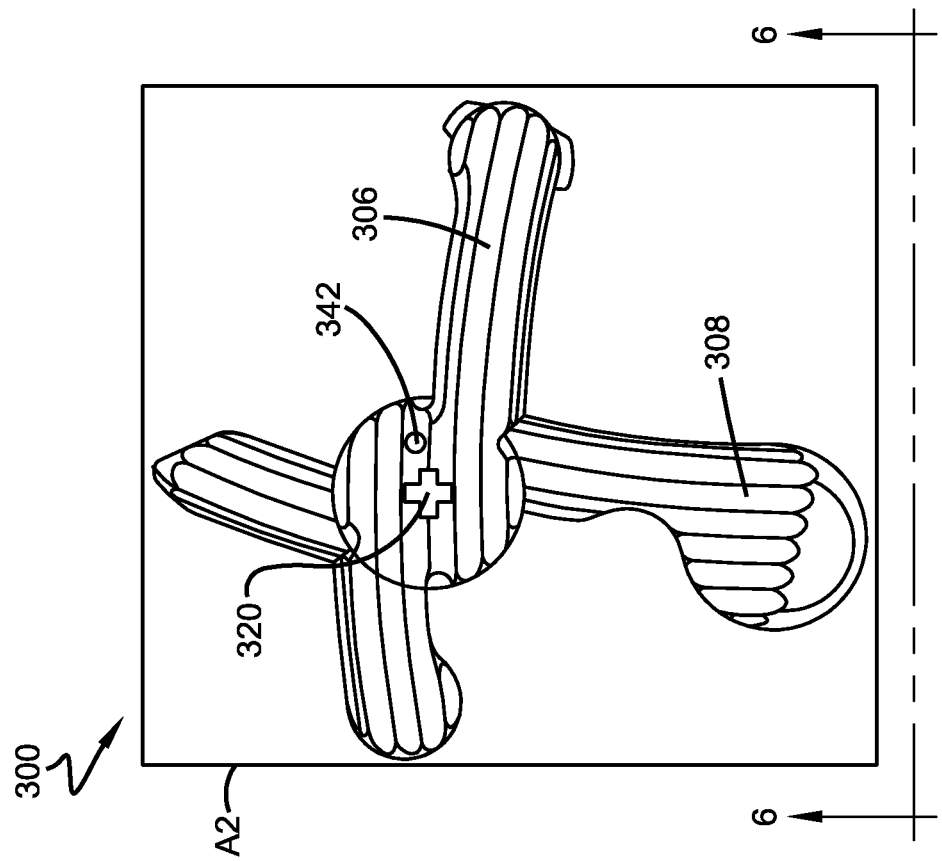
FIG. 4 is a top view of the spinal implant shown in FIG. 3 but in an expanded condition.

A spinal implant according to some aspects of the present teaching of this invention may be adjusted between a contracted or non-deployed condition and an expanded or deployed condition. This adjustment may be made when the implant is positioned within a vertebral space or when positioned outside of a vertebral space, such as prior to surgery. When an implant is adjusted from the expanded condition to the contracted condition while within a vertebral space, the resultant non-deployed condition is herein termed a collapsed condition. In some embodiments, a locking mechanism may be used to lock the implant in the deployed condition. The locking mechanism may be unlocked, permitting the implant to be adjusted from the deployed condition to the non-deployed condition.

Surgical instrumentation according to some aspects of the present teaching of this invention may be used to insert the implant within a vertebral space, while in the non-deployed condition, and adjust the implant into the deployed condition. In some embodiments, surgical instrumentation may be used to remove the implant from the vertebral space. In some embodiments the surgical instrumentation may be used to adjust the implant from the deployed condition into a collapsed condition before removing the implant. In what follows, numerous embodiments of spinal implants and surgical instrumentation will be described. Their use, according to some embodiments, will then be described.

Referring now to the drawings wherein the showings are for purposes of illustrating embodiments of the invention only and not for purposes of limiting the same, FIG. 1 illustrates a spinal segment 100 made up of two vertebral bodies 102, 104 attached together by ligaments with a disc 106 separating them. Facet joints 108 fit between the two vertebral bodies 102, 104 and allow for movement. The neural foramen 110 between the vertebral bodies 102, 104 allow space for the nerve roots to travel freely from the spinal cord 112 to the body. If it is required to remove the disc 106 and replaced it with an implant, the space occupied by the disc, the intradiscal space between the two adjacent vertebral bodies 102, 104, defines the vertebral space 114.

With reference now to FIG. 2, according to some aspects of the present teaching of this invention, a spinal segment 200 may be made up of three vertebrae 202, 204, 206 attached together by ligaments. If it is required to remove the middle vertebra 204 (it is shown diseased) along with the adjacent discs 208, 210, such as may be required because of a corpectomy defect, and replaced them with an implant, the space between the two outer vertebral bodies 202, 206, defines the vertebral space 212. It should be understood that these are simply two non-limiting examples of the vertebral space 114, 212 into which an implant can be inserted according to this invention because any vertebral space chosen with the sound judgment of a person of skill in the art can be used. As the components and operation of a spinal column is well known to those of skill in the art, further detail will not be provided here.

Figure 3:
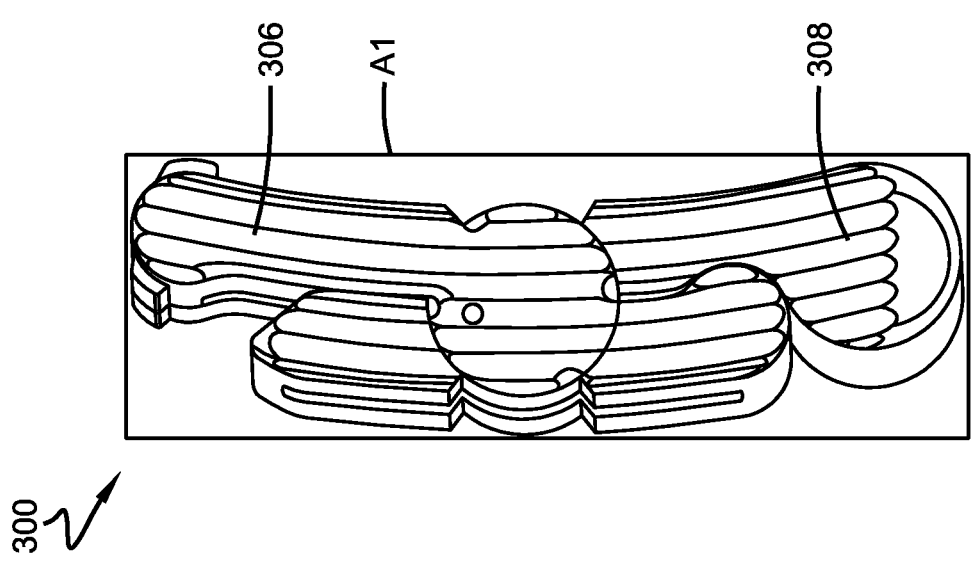
FIG. 3 is a top view of a spinal implant in a contracted condition.
Figure 6:
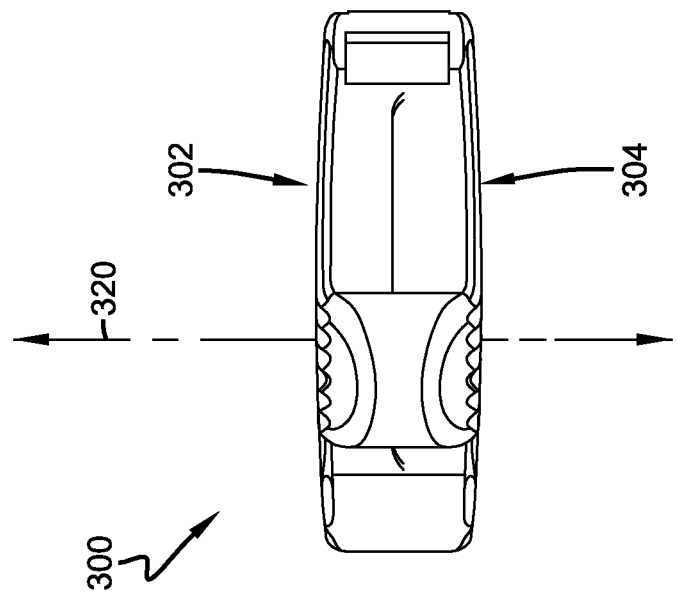
FIG. 6 is a view taken along the line 6-6 of FIG. 4.
Figure 5:
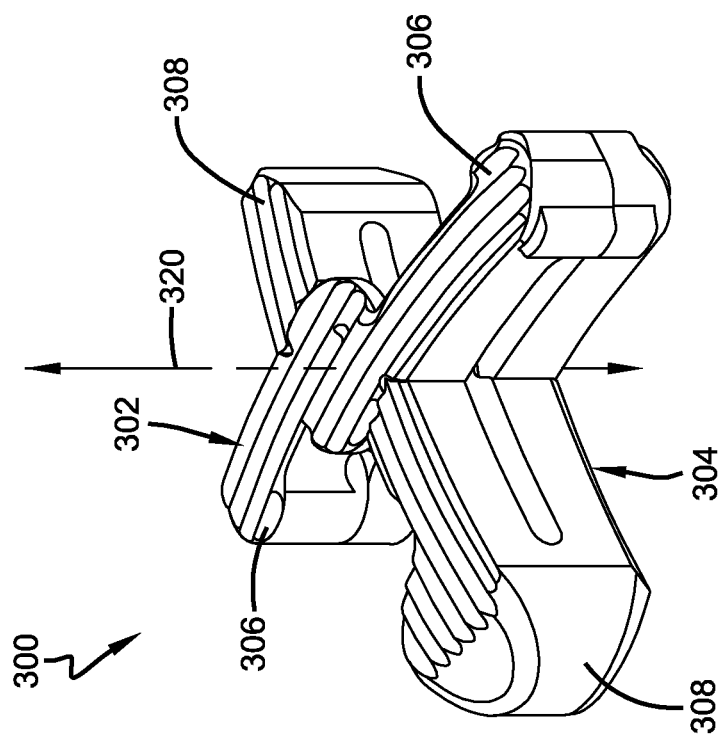
FIG. 5 is a top perspective view of the spinal implant shown in FIG. 4.

With reference now to FIGS. 3-9, according to some aspects of the present teaching of this invention, an implant 300 may positioned within the vertebral space in a non-deployed or contracted condition, as shown in FIGS. 3 and 7, and then may be adjusted within the vertebral space into a deployed or expanded condition, as shown in FIGS. 4 and 5. This expandable design is very beneficial for the surgeon. When in the non-deployed, contracted, reduced footprint condition, the implant 300 is small enough to be passed through a standard microdiscectomy type annulotomy, making it truly compatible with minimally invasive surgical (MIS) techniques. Once placed within the vertebral space, the implant 300 may be adjusted into the deployed or expanded condition where it provides a larger effective footprint area. This larger footprint is compatible with more invasive anterior lumbar interbody fusion or bilateral posterior techniques. The implant 300 may have two vertebral body endplate contact surfaces 302, 304 (top and bottom as shown in FIGS. 5 and 6) that face and contact the respective vertebral bodies within the vertebral space (shown in FIGS. 1 and 2). These vertebral body endplate contact surfaces 302, 304 may be serrated/knurled to facilitate cutting into bony endplates to prevent rotation or expulsion of the implant by external rotational or flexion-extension forces. Each vertebral body endplate contact surface 302, 304 may provide a first effective footprint area A1, as illustrated in FIG. 3, when in the non-deployed condition. The implant 300 vertebral body endplate contact surfaces 302, 304 may have a second larger effective footprint area A2, as illustrated in FIG. 4, when in the deployed condition. For purposes of this patent, "effective footprint area" is defined in U.S. Pat. No. 8,062,373 which is incorporated herein by reference in its entirety. As shown in FIGS. 7-9, the implant 300 may have a width, a length, a height a lordotic height and a lordosis angle when in the non-deployed condition.

Figure 10:
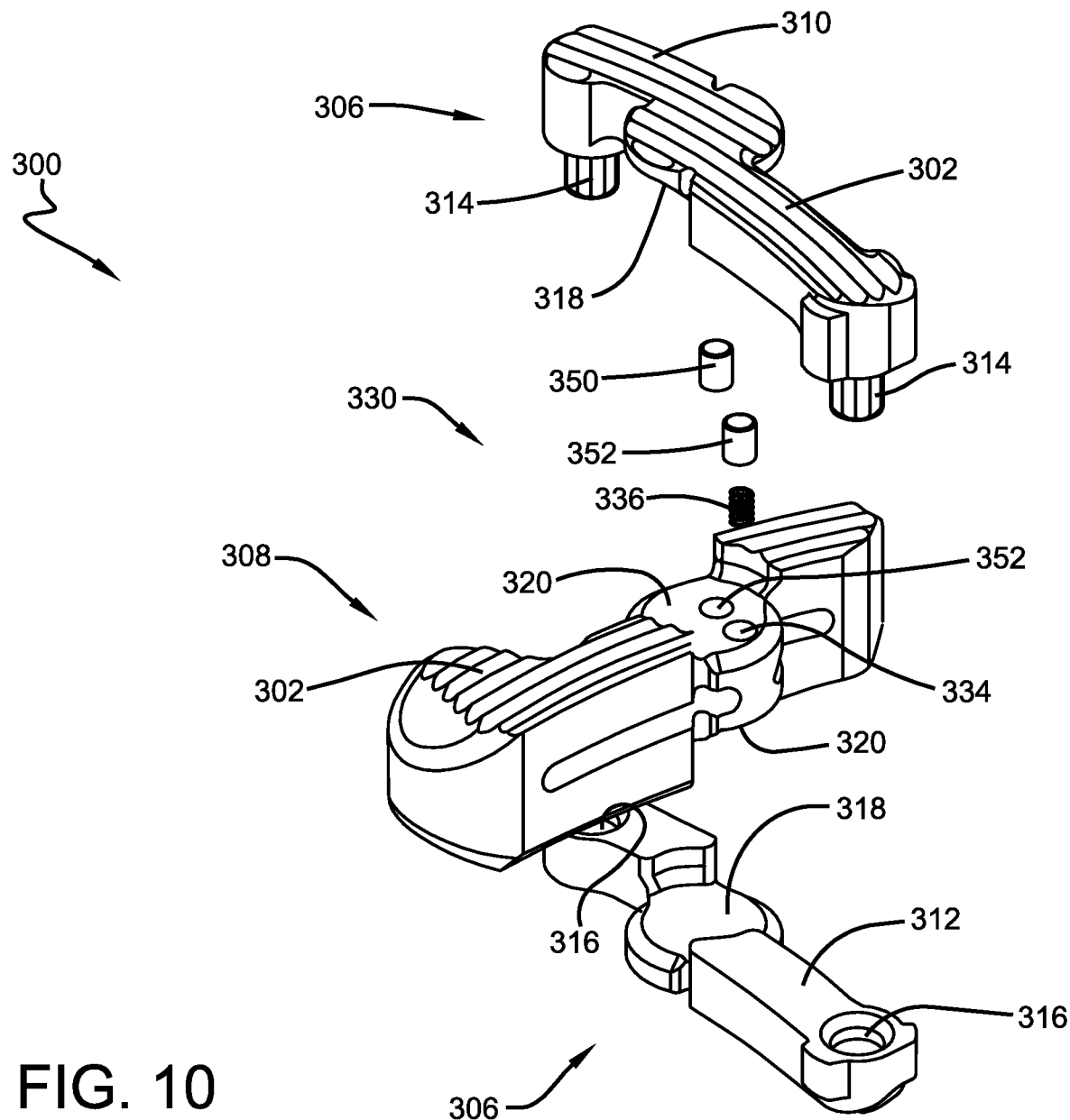
FIG. 10 is an assembly view of a spinal implant.
Figure 12:
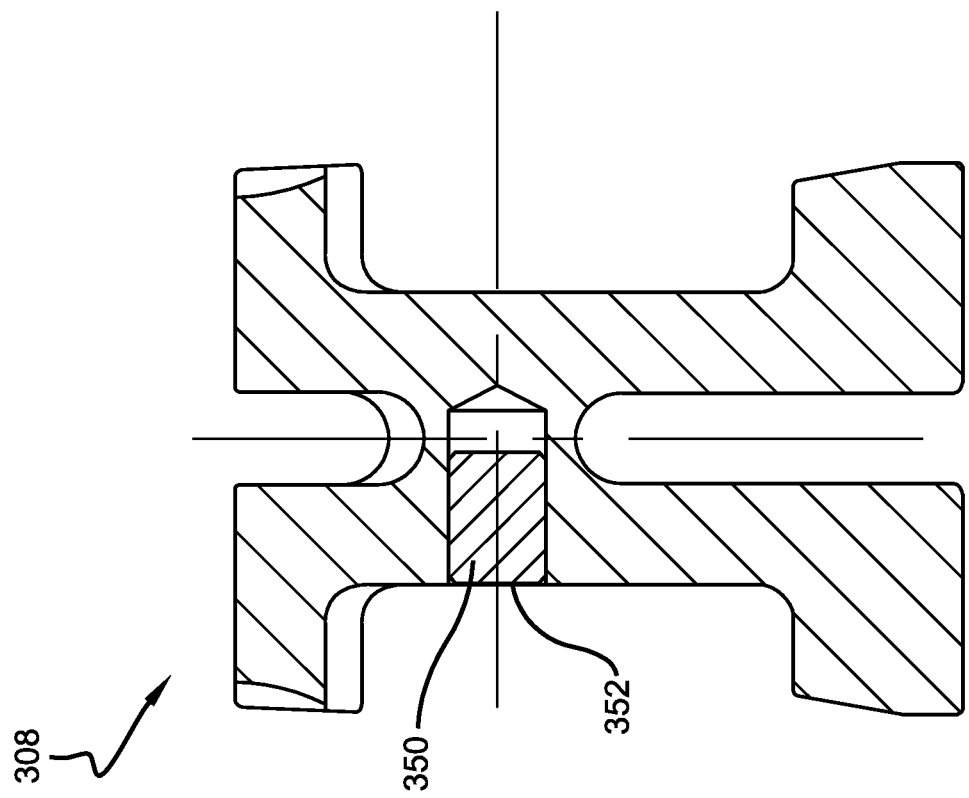
FIG. 12 is a view taken along the line 12-12 of FIG. 11.
Figure 11:
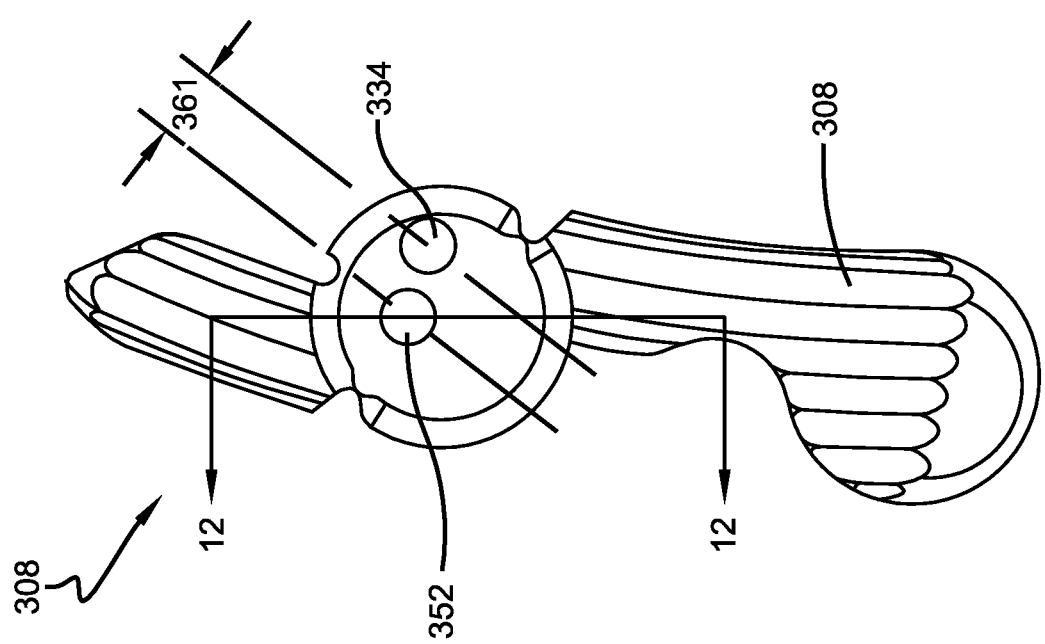
FIG. 11 is a top view of a spinal implant member.

With reference now to FIGS. 3-4 and 10, the implant 300 may include a first member 306 and a second member 308 that pivots with respect to the first member 306 between the non-deployed condition (FIG. 3) and the deployed condition (FIG. 4). While the specific design of the first and second members may be any chosen with the sound judgement of a person of skill in the art, for the embodiment shown the first member 306 has first and second beams 310, 312 that interconnect via posts 314, 314 that extend from opposite ends of beam 310 and that are received in corresponding slots 316, 316 formed on opposite ends of beam 312. While the posts shown extend from the first beam and the slots are formed in the second beam, it should be understood that in other embodiments this could be reversed and in yet other embodiments one post could extend from each beam with a corresponding post receiving slot in the opposite beam. Each beam 310, 312 may have mid-portions with contact surfaces 318, 318. The contact surfaces 318, 318 may be planar with generally circular shapes, as shown. The contact surfaces 318, 318 may be positioned in cut-out areas of the beams, as shown. The second member 308 may have a mid-portion with contact surfaces 320, 320 on opposite sides. The contact surfaces 320, 320 may be planar with generally circular shapes and may be positioned in cut-out areas of the beam, as shown. When the implant is assembled together, contact surfaces 318, 318 may engage corresponding contact surfaces 320, 320 providing the pivotal connection between the first and second members 306, 308. The pivotal connection may be about pivot axis 320, shown in FIGS. 4-6, which may define the axial directions indicated.

With reference now to FIGS. 3, 5 and 10, a locking mechanism 330 may be used to lock the first member 306 to the second member 308 preventing the first member 306 from pivoting with respect to the second member 308 about the pivot axis 320. The locking mechanism 330 may also, in some embodiments, be adjusted to unlock the first member 306 from the second member 308 permitting the first member 306 to pivot with respect to the second member 308 about the pivot axis 320. In some embodiments, the locking mechanism 330 locks the first member 306 to the second member 308 only when the implant is in the deployed condition (shown, for example, in FIG. 5). In some embodiments, the locking mechanism 330 locks the first member 306 to the second member 308 automatically when the desired relative position between the first and second members 306, 308 has been achieved. In some embodiments, the locking mechanism 330 can be unlocked in more than one way, according to the needs of the surgeon.

Figure 13:
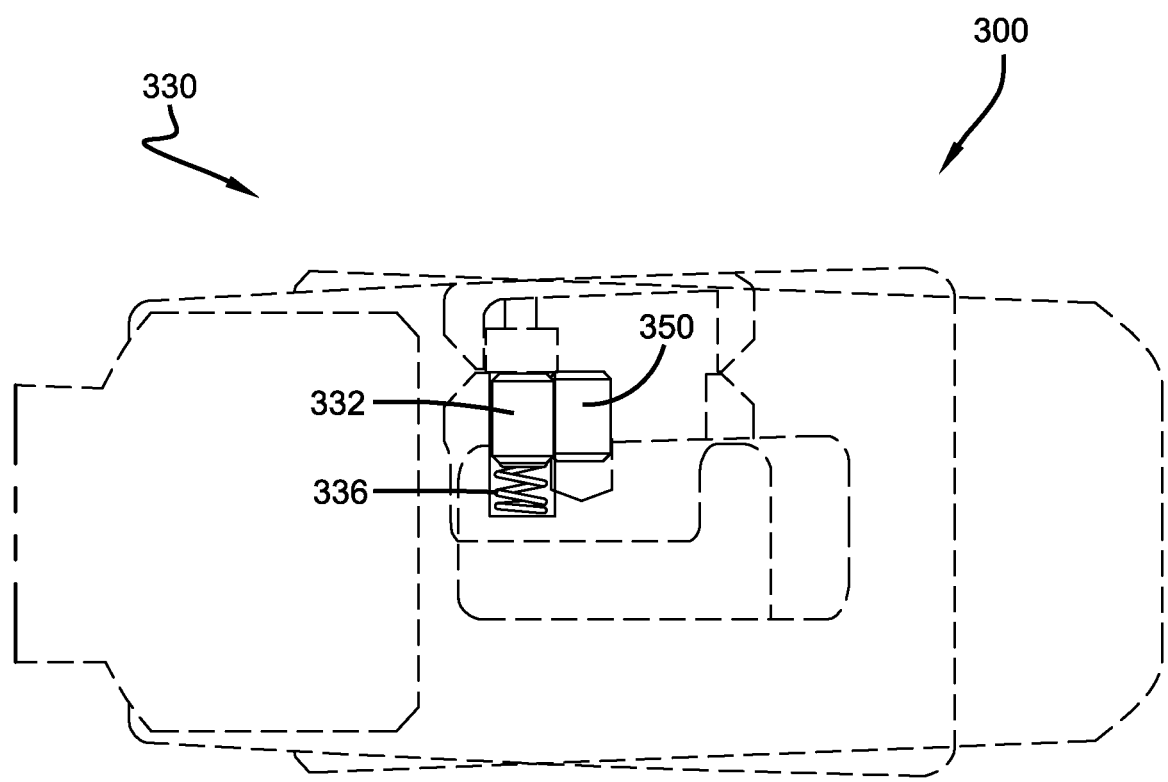
FIG. 13 is a side view of a spinal implant in a non-deployed condition as may be seen fluoroscopically with the relative positions of pins visible.
Figure 14:
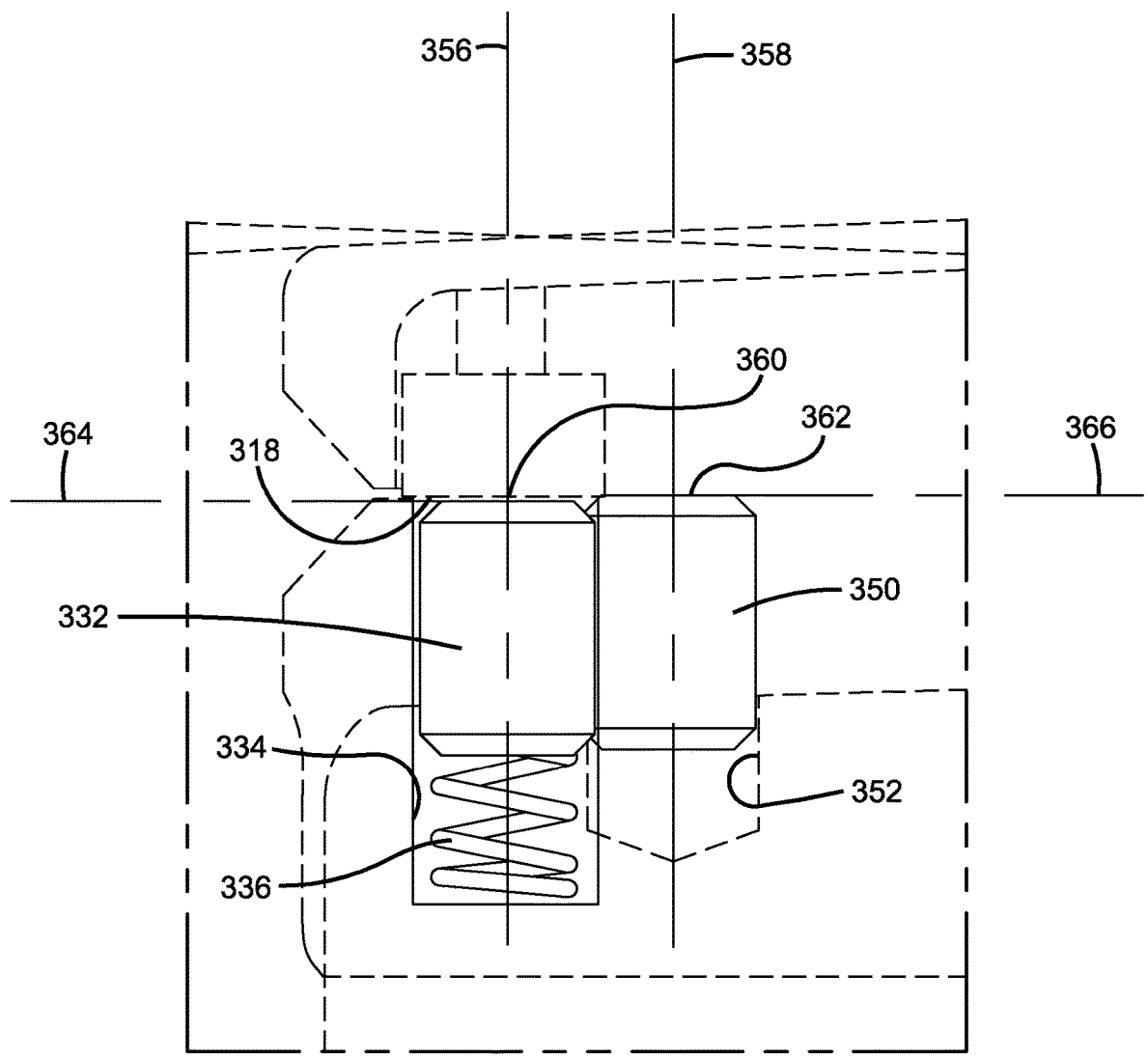
FIG. 14 is a close-up view of the pins shown in FIG. 13.
Figure 15:
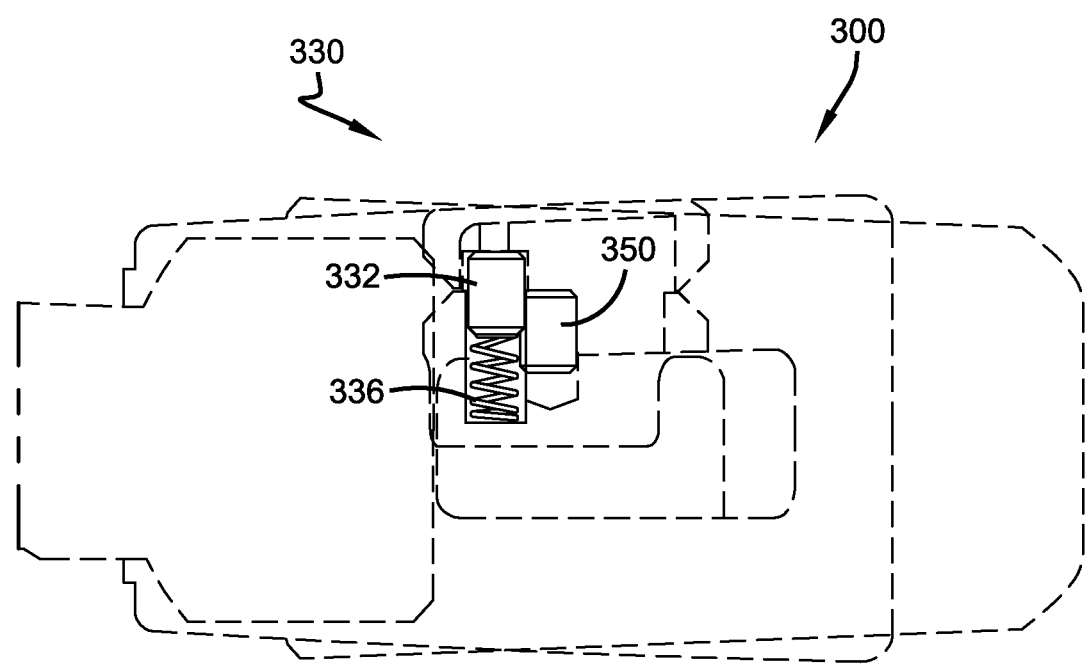
FIG. 15 is a view similar to that shown in FIG. 13 but with the spinal implant in a deployed condition.
Figure 16:
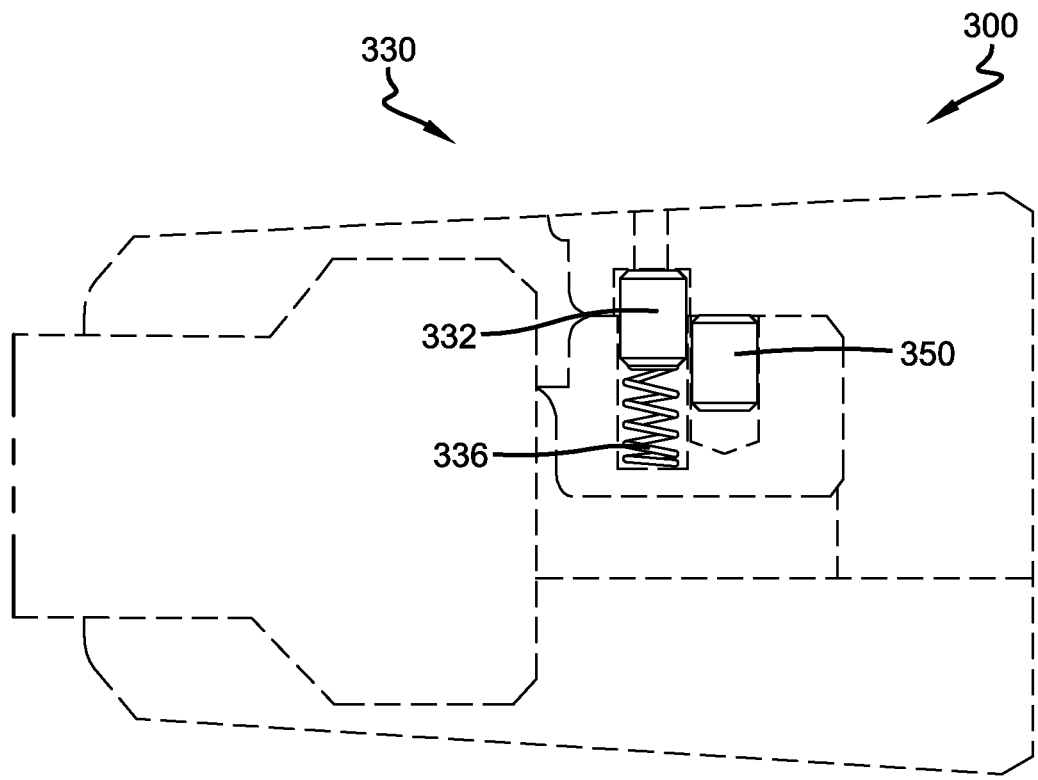
FIG. 16 is a view similar to that shown in FIG. 15 but from a lateral angle.
Figure 17:
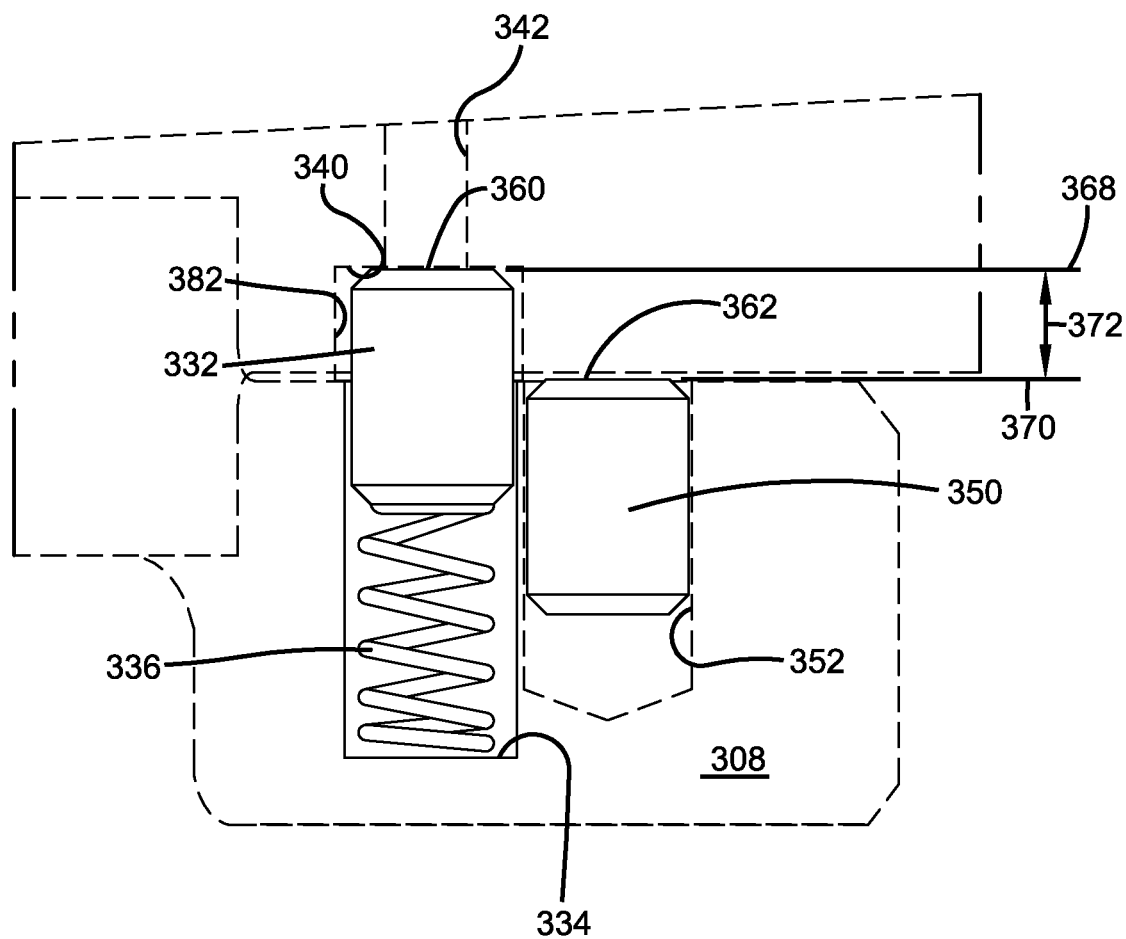
FIG. 17 is a close-up view of the pins shown in FIG. 16.

With reference now to FIGS. 10-11 and 13-17, for the embodiments shown, the locking mechanism 330 may include a pin 332 that is supported to the second member 308 and that is biased via a biasing force in an axial direction (upward in FIGS. 13-17). In some embodiments, pin 332 may be fluoroscopically detectable as distinct from the first and second members 306, 308 for purposes that will be discussed below. In one embodiment, the pin 332 is supported to second member 308 via placement within second member opening 334. In some embodiments, the biasing force is generated by a biasing force generator 336 in the form of a compression spring. The biasing force generator 336 may be supported within opening 334 and positioned between the second member 308 and the pin 332, as shown. With this arrangement, the biasing force generator 336 applies a biasing force to the pin 332 that biases the pin 332 in an axial direction (upward in FIGS. 13-17). The effect of the biasing force on the pin 332 may depend on the relative position of the first and second members 306, 308. When the first and second members 306, 308 are relatively positioned with an opening 338 formed in the first member 306 collinear with the pin 332, as shown in FIG. 15-17, the biasing force will move the pin 332 axially into the opening 338. Opening 338 may be defined by a surface 340 (FIG. 17) that a pin surface (upper surface in the FIGURES) of the pin 332 contacts, limiting how far the pin 332 can be moved by the biasing force into opening 338. When the pin 332 is positioned within opening 338 as just described, the locking mechanism 330 is in the locked condition as the pin 332 locks the first member 306 to the second member 308. In this condition, the first member 306 cannot rotate about the pivot axis 320 with respect to the second member 308. Note that the biasing force may be continual which causes the pin 332 to enter the opening 338 automatically when the opening 338 is collinear with the pin 332. The pin 332 and opening 338 may be positioned such that the locked condition only occurs when the implant is in the deployed condition. When the pin 332 is not collinear with the opening 338, as shown in FIGS. 13-14, the biasing force holds the pin 332 against the contact surface 318 of the first member 306, preventing the pin 332 from entering the opening 338. In this condition, the first member 306 can pivot about the pivot axis 320 with respect to the second member 308. This relative pivotal motion may be possible when the implant in in the non-deployed condition. It should be understood that though the use of only one pin has been described, one or more pins may be used as part of the locking mechanism 330 according to some aspects of the present teaching of this invention.

Figure 18:
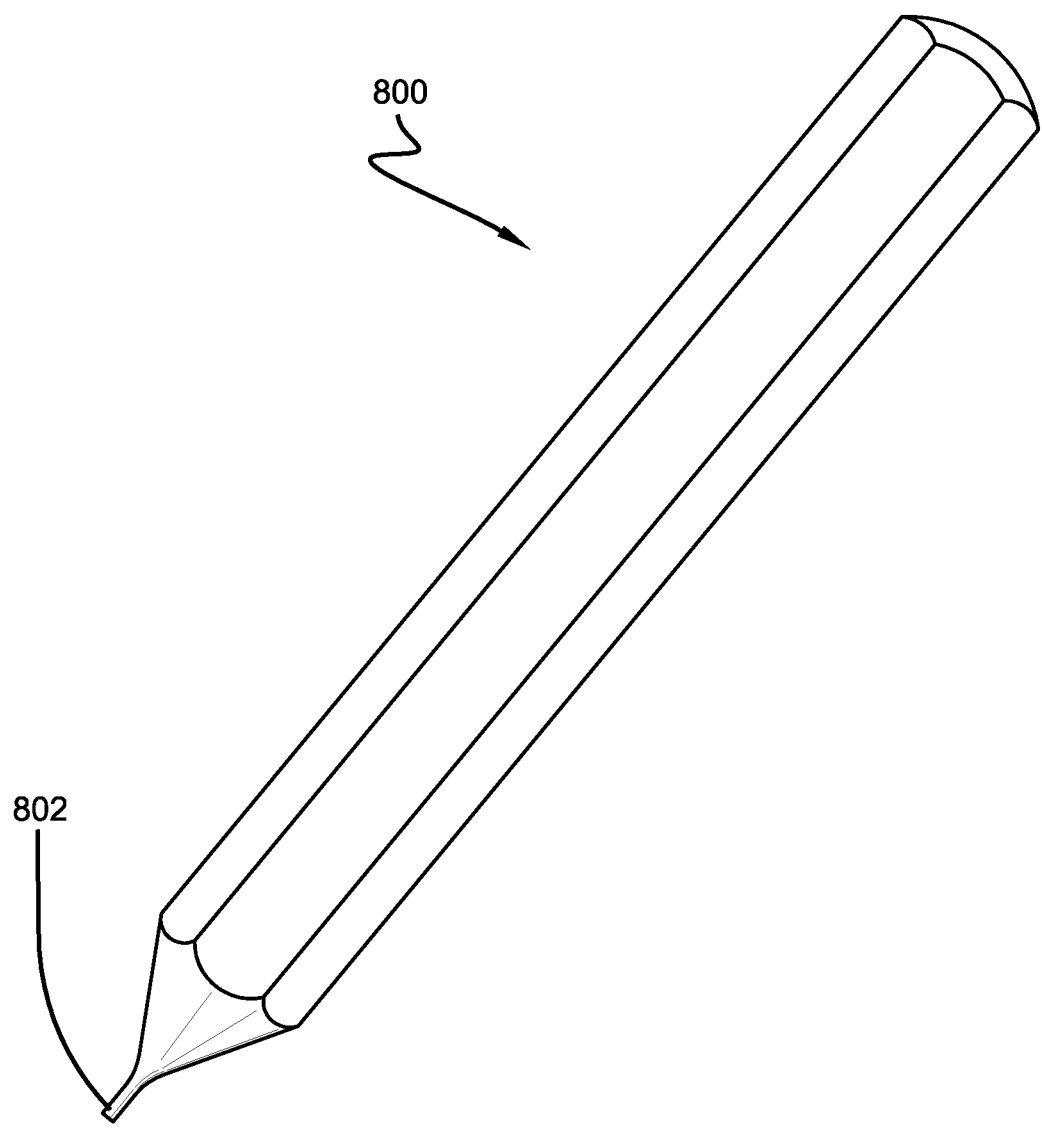
FIG. 18 is a side view of a lock release tool.

With reference now to FIGS. 4-5, 10, 13-14 and 17-18, according to some embodiments of this invention, the locking mechanism 330 may be unlocked, that is, the locking mechanism 330 may be adjusted to unlock the first member 306 from the second member 308 permitting the first member 306 to pivot with respect to the second member 308 about the pivot axis 320. The opening 338 may have opposite axial ends (top and bottom in the FIGURES). The pin 332 enters one axial end (the bottom as shown) as it creates the locked condition. The opposite axial end (the top as shown) may communicate with a cavity 342 (FIGS. 4 and 17) that also communicates outside the first member 306, as shown. The cavity 342 thus provides access to the pin 332. FIG. 18 shows a lock release tool 800. To adjust the locking mechanism 330 out of the locked condition, the surgeon may insert the tip 802 of the lock release tool 800 into the cavity 342 sufficient to contact the upper surface of the pin 332 and force the pin 332 out of the opening 338 in the first member 306 against the biasing force. This positions all of the pin 332 back into opening 334 in the second member 308 (shown in FIGS. 13-14) and thereby unlocks the locking mechanism 330. While maintaining the tip 802 against the pin 332 in this manner, the surgeon can easily pivot the first member 306 with respect to the second member 308. Once the unlocked condition has been achieved, the surgeon can simply remove the lock release tool 800. This use of release tool 800 may be used, for example, when the implant 300 has been inadvertently adjusted from its non-deployed condition into the deployed condition prior to placement within a patient.

Figure 19:
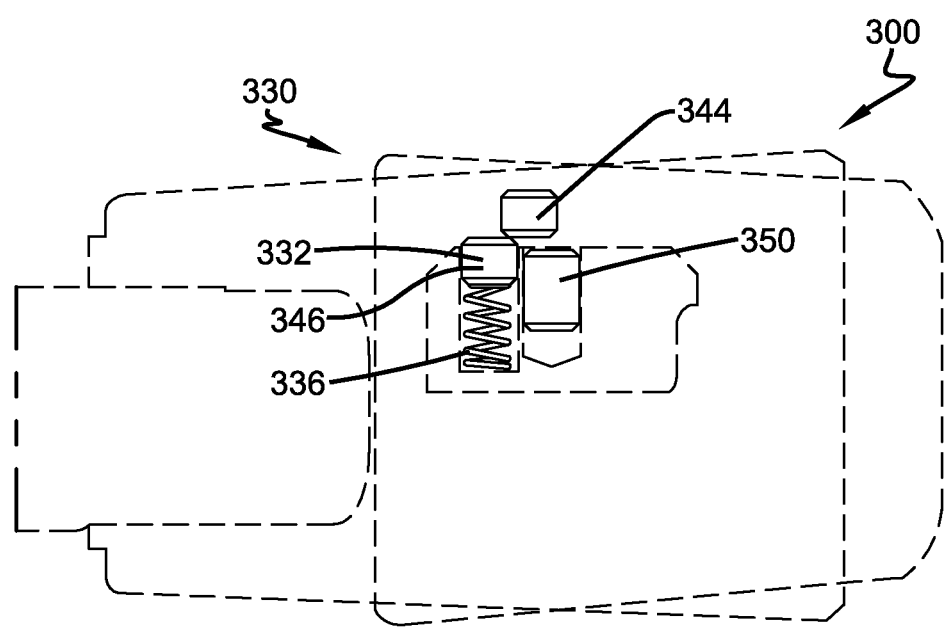
FIG. 19 is a view similar to that shown in FIG. 13 but with the spinal implant in a collapsed condition.
Figure 20:
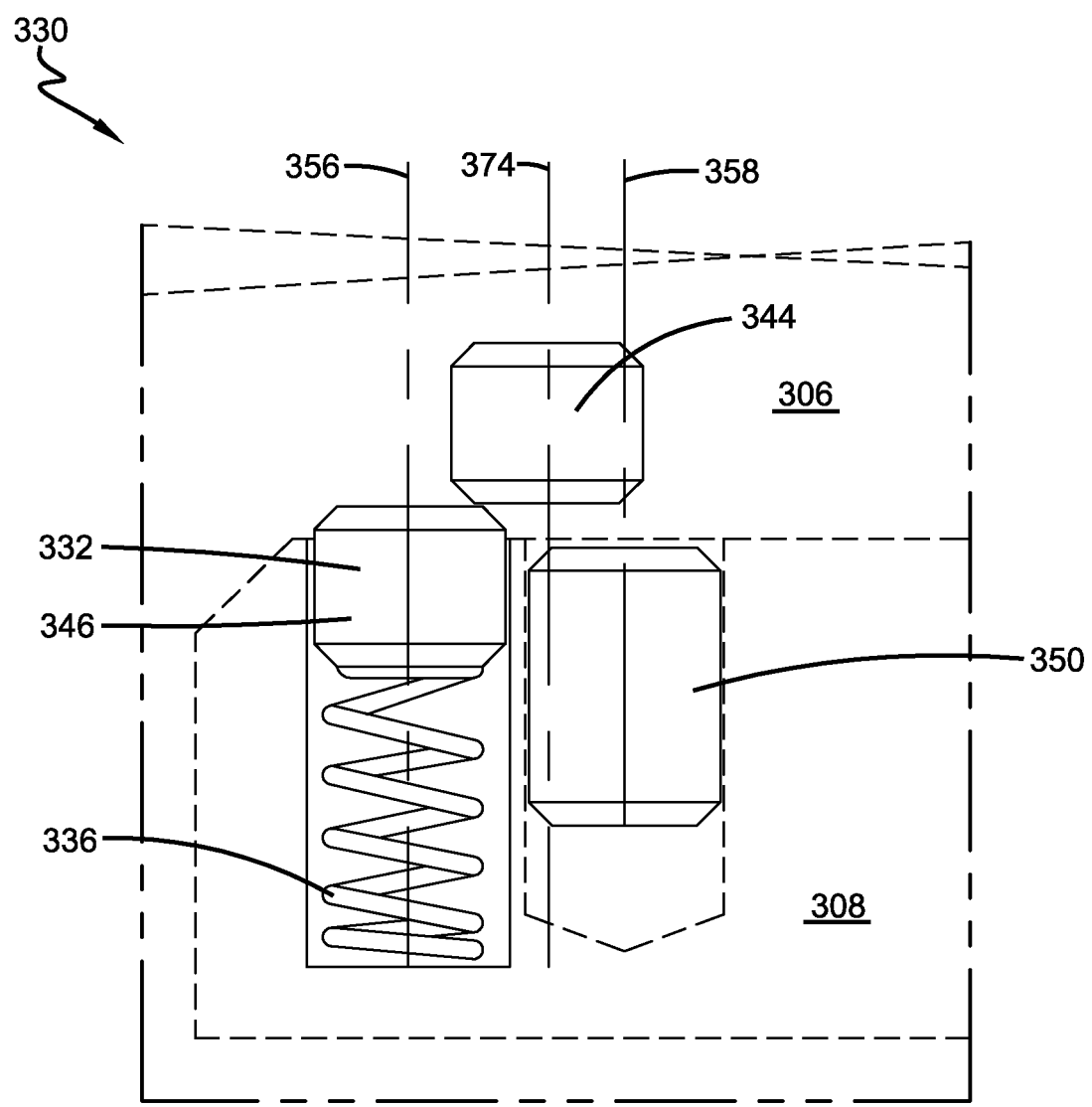
FIG. 20 is a close-up view of the pins shown in FIG. 19.

With reference now to FIGS. 5, 10 and 19-20, according to some embodiments of this invention, the locking mechanism 330 may be unlocked by separating the pin 332 into two (or more) portions. In one specific embodiment, the pin 332 may be sheared into two portions. This separation of the pin 332 may be used, for example, when the implant 300 is positioned within the vertebral space and has been deployed but needs to be collapsed and then removed. FIGS. 19-20 show the pin 332 separated into portions 344, 346. The surgeon may separate the pin 332 in a manner that will be discussed further below. Once separated, portion 344 may remain within in the opening 338 in first member 306 while portion 346 remains within opening 334 in the second member 308. In this way, the surgeon can rotate the first member 306 with respect to the second member 308 and then remove the implant 300. Note that when the implant is unlocked in this manner (separating pin 332), the implant can no longer be used with a patient.

With reference now to FIGS. 5 and 10-17, to assist the surgeon with more certain knowledge about the condition of the implant 300 (non-deployed or deployed)—especially when the implant is positioned within the patient's vertebral space—a pin 350 may be used as a reference with pin 332. Pin 350 may be fluoroscopically detectable as distinct from the first and second members 306, 308 and may be supported to either first member 306 or second member 308. For the embodiments shown, pin 350 is supported to the second member 308 via placement within second member opening 352. Pin 350 may be fixed to the second member such as, in one embodiment, by a press fit within opening 352. The surgeon may use the differing relative positions between pin 332 and pin 350 to determine the condition of the implant—non-deployed or deployed. In one embodiment, the surgeon may use the different relative axial positions between pins 332, 350 for this purpose.

With continuing reference to FIGS. 5 and 10-17, each pin may have a longitudinal axis that is parallel to the pivot axis 320. Specifically, as shown in FIG. 14, pin 332 may have a longitudinal axis 356 and pin 350 may have a longitudinal axis 358. These axes 356, 358 may, in some embodiments, also be the longitudinal axes of the corresponding openings 334, 352, respectively. Axes 356, 358 may be separated a distance 360, indicated in FIG. 11. Distance 360 may vary depending on the size of the implant but should be small enough to provide easy visualization for the surgeon during fluoroscopy. In some embodiments, distance 360 is not greater than 1.0 inches. In other embodiments, distance 360 is not greater than 0.8 inches. In other embodiments, distance 360 is not greater than 0.6 inches. In other embodiments, distance 360 is not greater than 0.4 inches. In other embodiments, distance 360 is not greater than 0.2 inches.

Still referring to FIGS. 5 and 10-17 but especially FIG. 14, pin 332 may have an axially upper most point 360 and pin 350 may have an axially upper most point 362. It should be noted that "upper most" assumes that the implant is positioned as shown in FIGS. 13-17. As well understood by persons of skill in the art, the actual position of the implant at any particular time will depend on the position of the patient and/or the desired position of the implant for the surgeon. Thus, in properly interpreting "axially upper most" it must be understood that the implant must be oriented as shown in FIGS. 13-17. A plane that simultaneously intersects the point 360 and is perpendicular to the pivot axis 320 when the implant is in the non-deployed condition is given reference 364 in FIG. 14. A plane that simultaneously intersects the point 362 and is perpendicular to the pivot axis 320 when the implant is in the non-deployed condition is given reference 366. A plane that simultaneously intersects the point 360 and is perpendicular to the pivot axis 320 when the implant is in the deployed condition is given reference 368 in FIG. 17. A plane that simultaneously intersects the point 362 and is perpendicular to the pivot axis 320 when the implant is in the deployed condition is given reference 370. Because both pins are fluoroscopically detectable as distinct from the first and second members 306, 308, the surgeon can easily see the relative positions of the pins 332, 350 using fluoroscopic imagery and thus easily determine the condition of the implant. To further assist the surgeon, in one embodiment the planes 364, 366 are coplanar, or near coplanar. In one specific embodiment, the axial distance between plane 364 and plane 366 is 0.2 inches or less. In another embodiment, the axial distance between plane 364 and plane 366 is 0.1 inches or less. In one specific embodiment, the axial distance between plane 368 and plane 370, distance 372, is 0.2 inches or more. In another embodiment, distance 372 is 0.3 inches or more. Thus, using fluoroscopy, the surgeon can quickly and easily determine the condition of the implant (non-deployed or deployed).

With reference now to FIGS. 5 and 10-20, the previously noted pin longitudinal axes can also be used to make it easy for the surgeon to determine when the implant 300 is unlocked by pin separation. Specifically, as shown in FIG. 20, pin portion 346 will maintain longitudinal axis 356 (since it remains in opening 334) and pin 350 will maintain longitudinal axis 358 (since it remains in opening 352). Pin portion 344, however, will have a longitudinal axis 374 (also parallel to the pivot axis 320) that is non-collinear with either of axis 356 or axis 358. Thus, using fluoroscopy, the surgeon can quickly and easily determine that pin 332 has separated and thus that the implant is unlocked. With this knowledge, the surgeon can pivot the first member 306 relative to the second member 308 sufficient to reduce the footprint so the implant 300 can be removed.

With reference now to FIGS. 10-20, pins 332, 350 can be sized and shaped and can be formed of any material chosen with the sound judgement of a person of skill in the art. As noted above, the pins 332, 350 may be formed of a material that makes them fluoroscopically detectable as distinct from the first and second implant members 306, 308. In one non-limiting embodiment, the pins 332, 350 are made of tantalum. The pins 332, 350, in the embodiments shown, are generally cylindrical in shape. Their diameters and axial heights can be chosen to match the size and use of the particular implant. In one embodiment, pins 332, 350 are similar in size and shape. In a more specific embodiment, shown, pins 332, 350 have the same size and shape. This simplifies implant construction.

Figure 21:
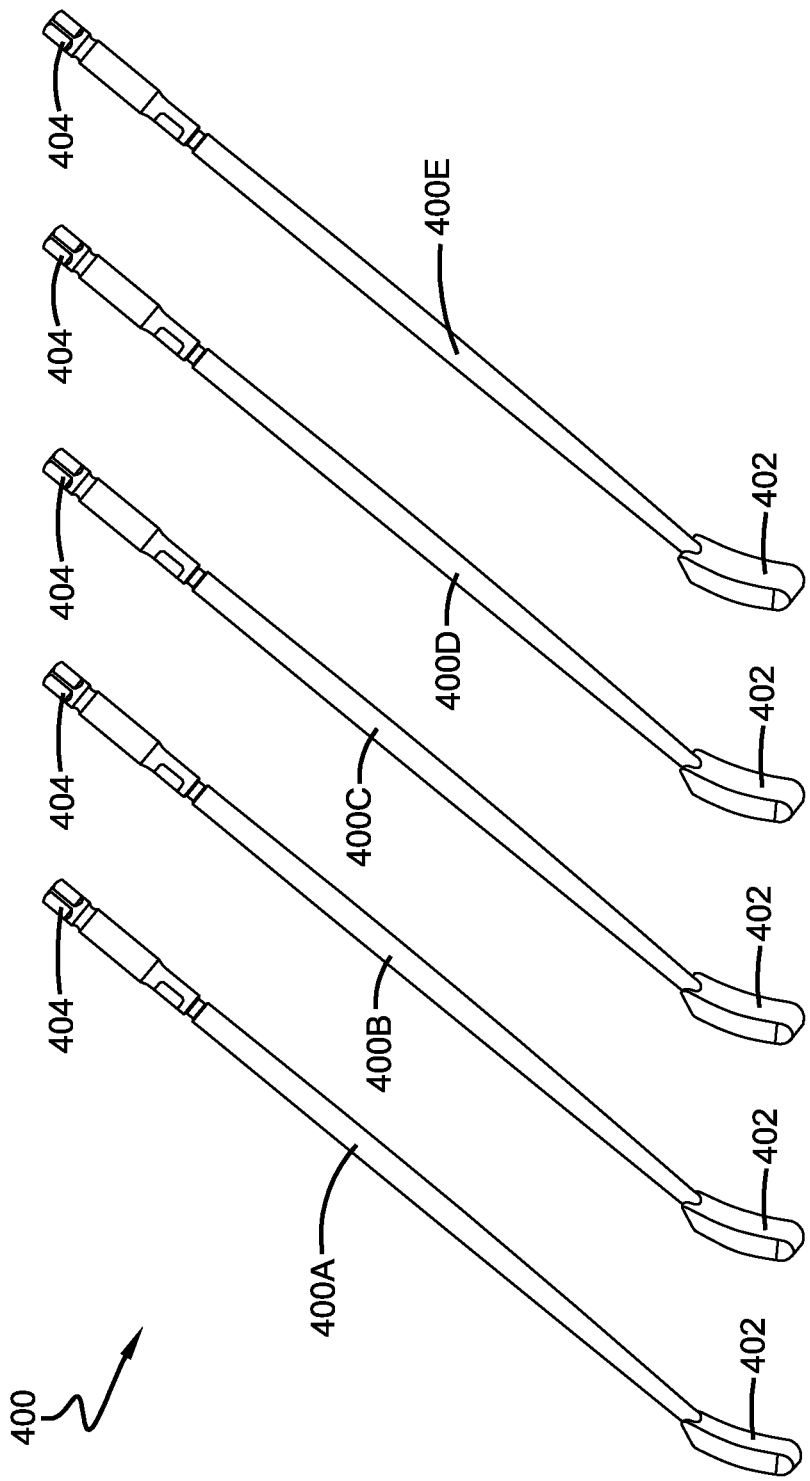
FIG. 21 shows several different sized trials.
Figure 23:
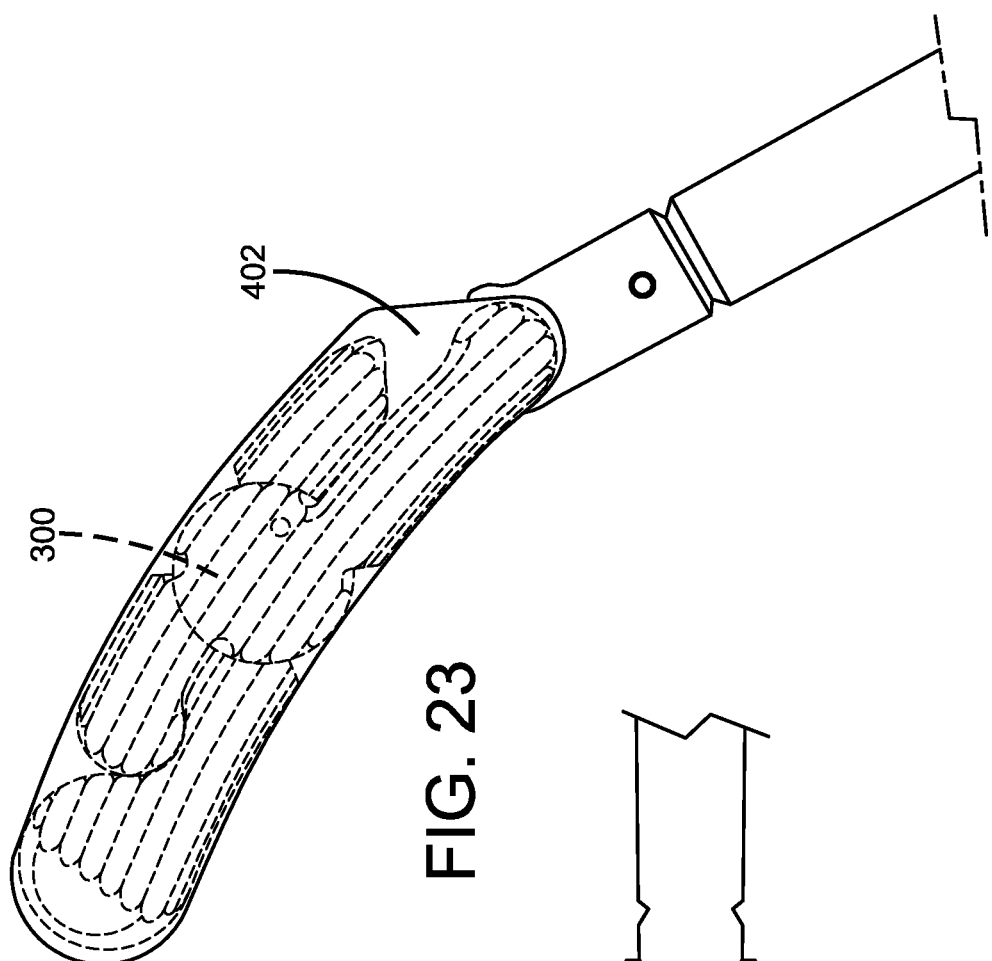
FIG. 23 is a top view illustrating how a trial's implant facsimile is the same size as a particular implant.
Figure 22:
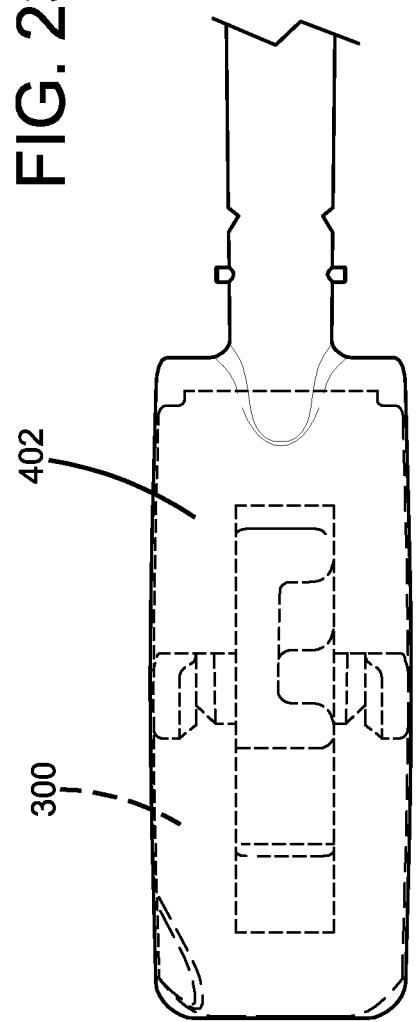
FIG. 22 is a side view illustrating how a trial's implant facsimile is the same size as a particular implant.

With reference now to FIGS. 21-25, the surgical instrumentation according to some aspects of the present teaching may include one or more trials used to determine what size of implant will be required for a particular patient. FIG. 21 shows five different trials 400, each given a lettered suffix A through E. Each trial 400 may have a longitudinally extending shaft with an implant facsimile 402 at its distal end and an attachment surface 404 at its proximal end. FIGS. 22-23 illustrate how each implant facsimile 402 may have dimensions corresponding to the dimensions of a particular non-deployed implant 300. The five trials 400 shown in FIG. 4 (400A-400E) may be the same except that the implant facsimiles 402 have different dimensions corresponding to different implant dimensions, as shown in FIGS. 7-9. It should be understood that while only five sized trials 400 are shown, any number of trials as chosen by a person of skill in the art may be provided for the surgeon.

Figure 25:
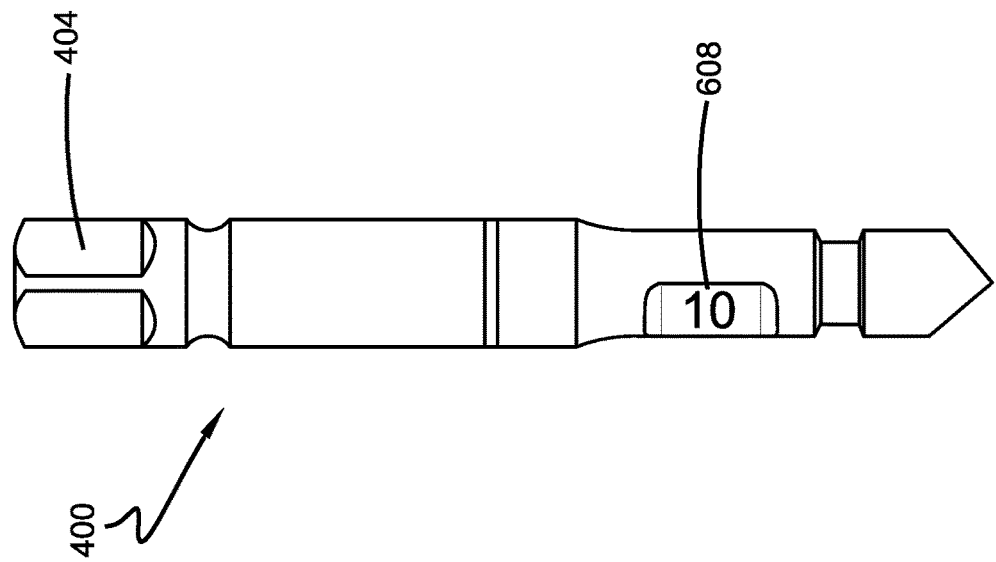
FIG. 25 is a side close-up view of a proximal end of a trial.
Figure 24:
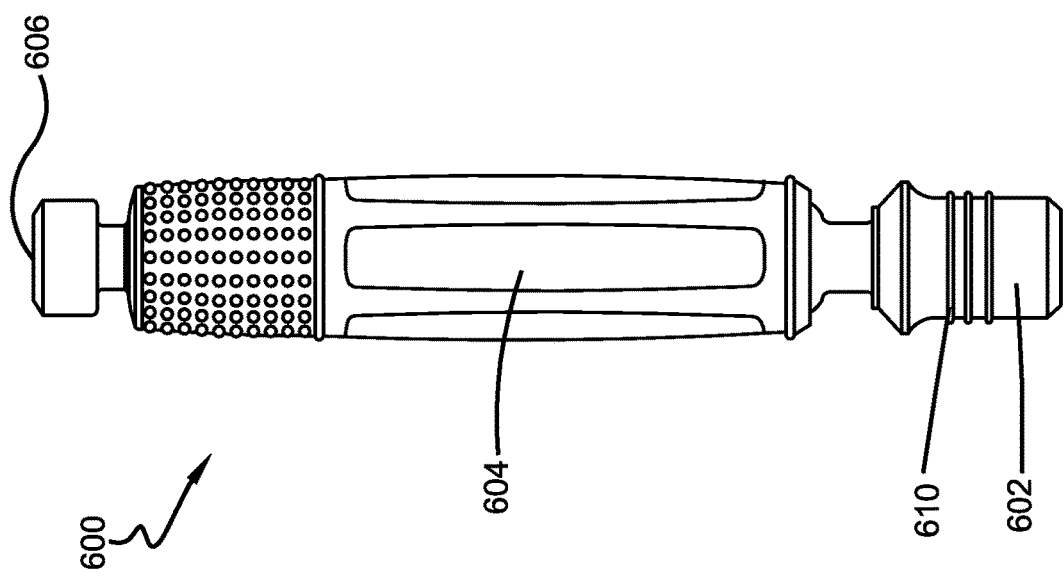
FIG. 24 is a side view of a handle designed to attach to different sized trials.
Figure 26:
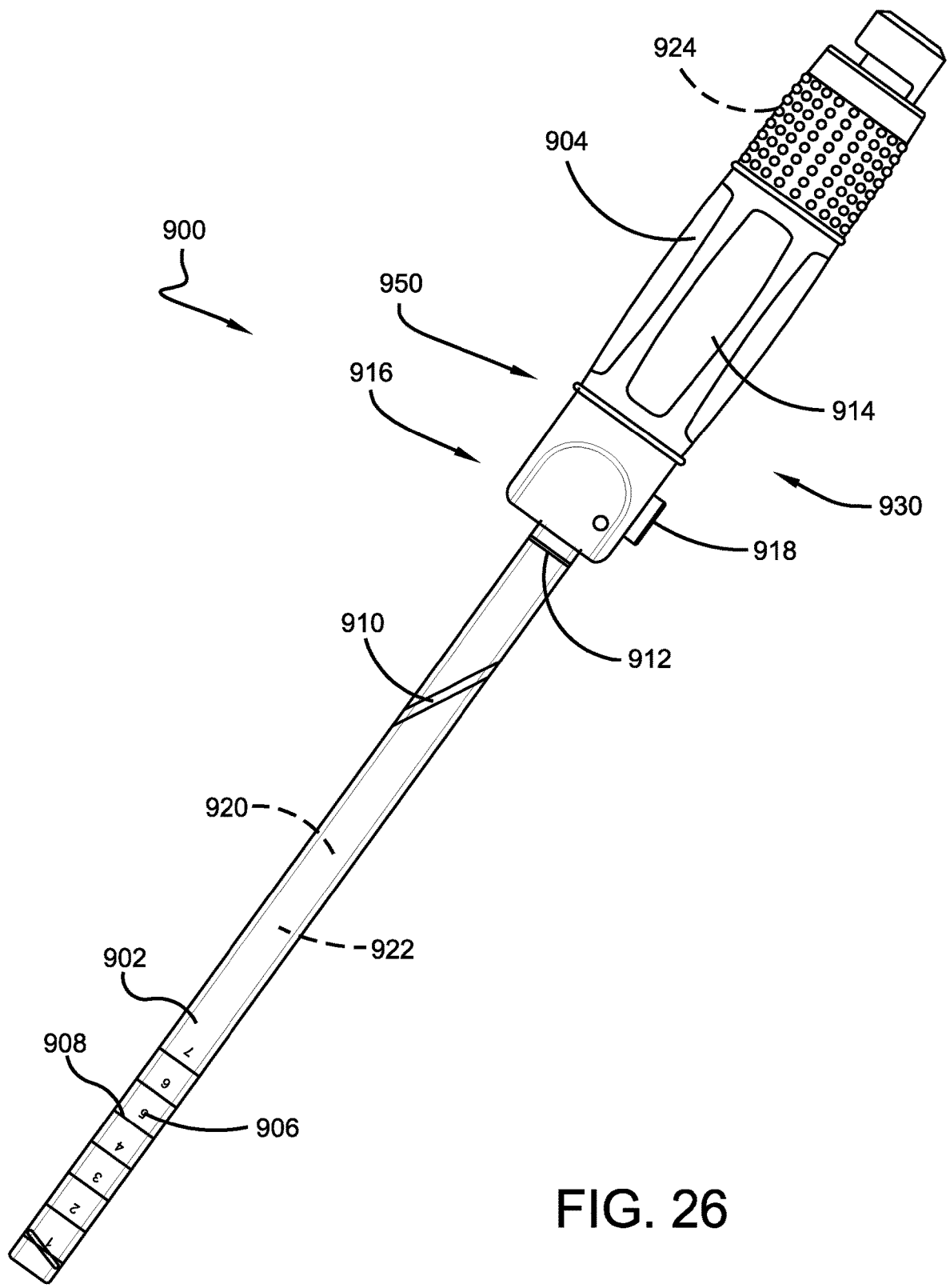
FIG. 26 is a side view of an inserter.
Figure 27:
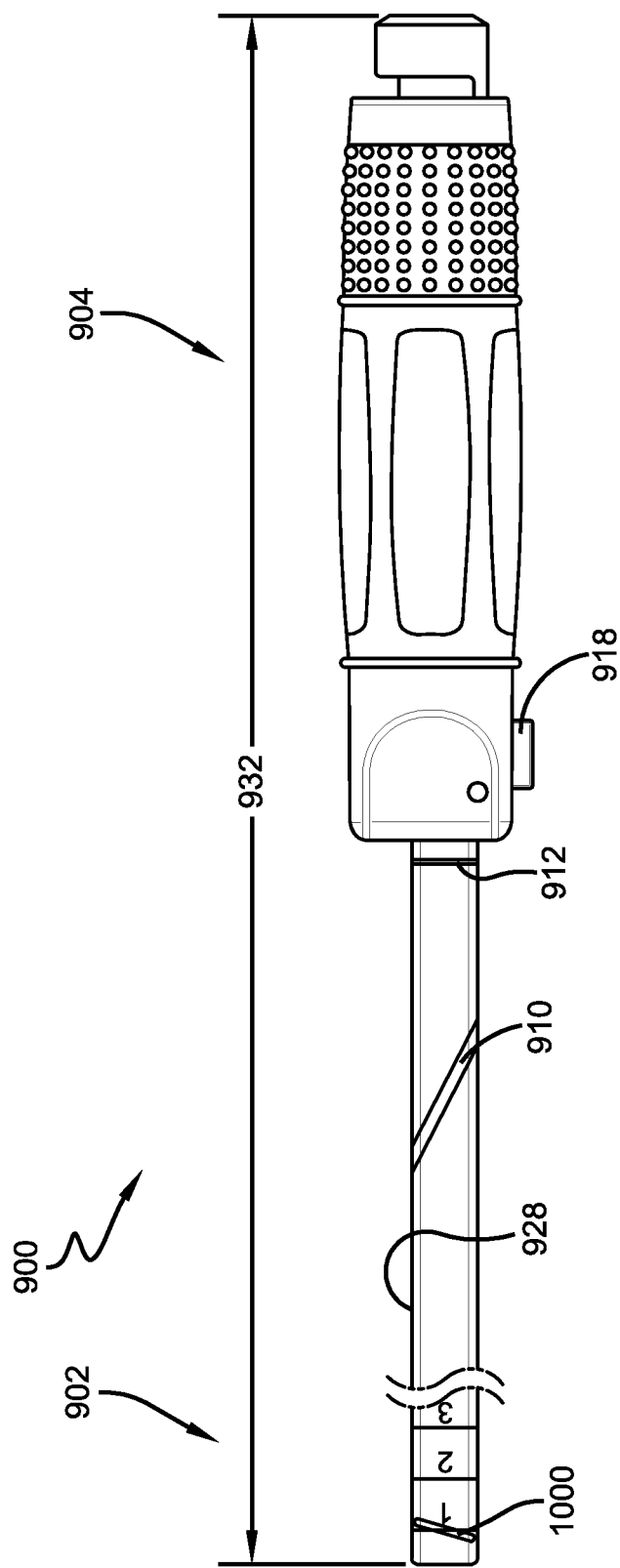
FIG. 27 is a side view of an inserter but with some portion removed for clarity.
Figure 28:
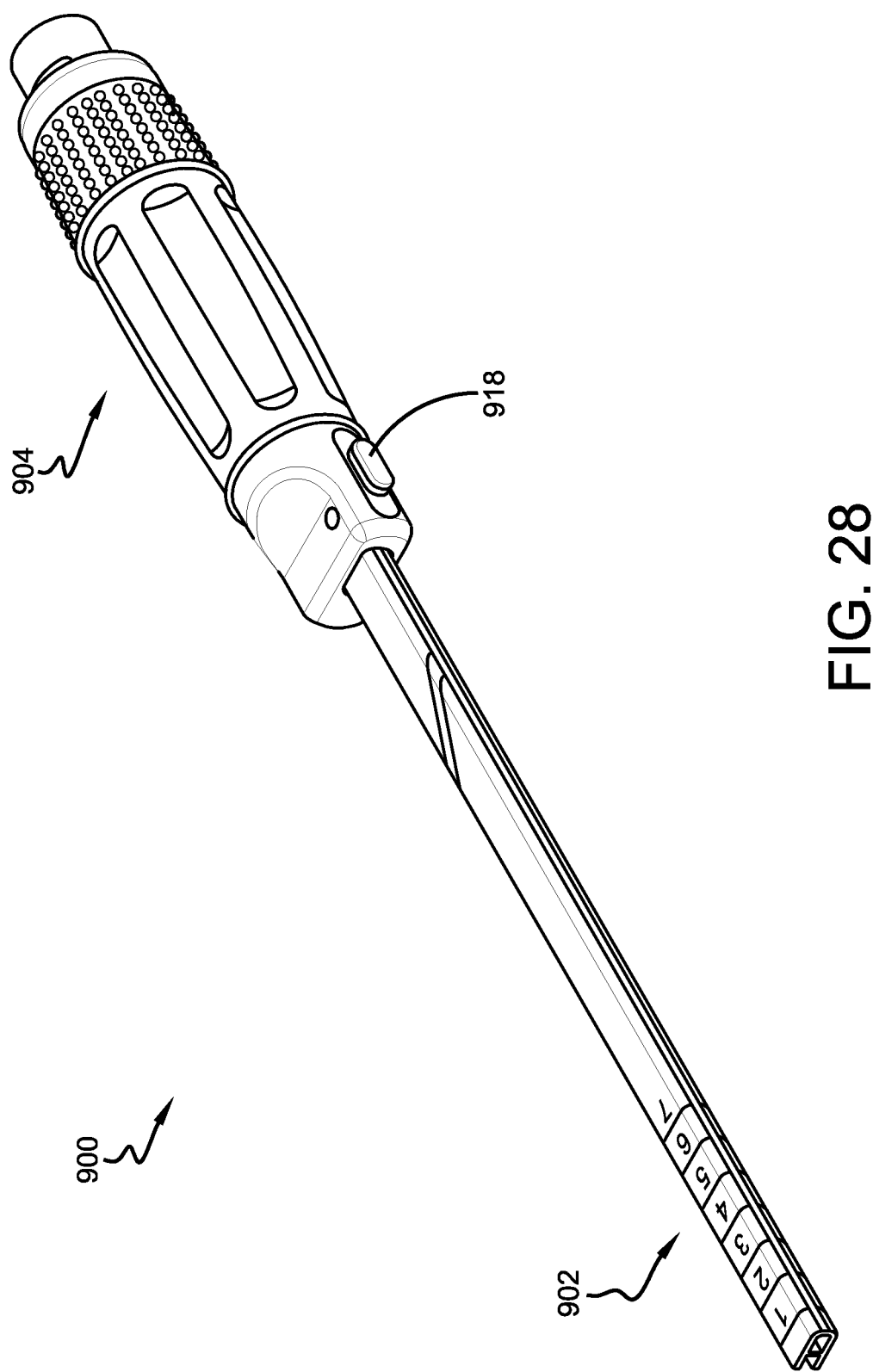
FIG. 28 is a side perspective view of an inserter.

FIG. 24 shows a handle 600 which may be used with any of the trials 400 shown in FIG. 21. The handle 600 may include a distal end with a trial receiving surface 602, a midsection with a grip surface 604, and a proximal end with a force receiving surface 606. The trial receiving surface 602 may be designed to engage with the attachment surface 404 of each trial 400. FIG. 25 shows the proximal end of a trial where the attachment surface 404 may be seen in more detail. The engagement between the trial receiving surface 602 and the attachment surface 404 can be any chosen with the sound judgment of a person of skill in the art. For the example shown, the trial receiving surface 602 comprises an opening shaped to receive the shape of the attachment surface 404. The attachment surface 404 may have an outer surface sized to match the inner surface of the opening defining the receiving surface 602. In this way, the surgeon has a socket style, "quick connect" attachment so that various trials 400 can be easily attached and detached from the handle 600 as the appropriate implant size is determined.

The distal end may include a textured surface 610 to provide a tactile response to the surgeon and to prevent slippage.

With reference now to FIGS. 21-25, each trial 400 may include an information surface 608 where information concerning the trial 400 can be provided for the surgeon. The information surface 608 may, for example, include information regarding the size of the implant facsimile at the distal end of that particular trial 400. The grip surface 604 of the handle 600 may be used by the surgeon when gripping the handle 600 and when using the handle along with the trial 400 that is attached to the handle 600. The force receiving surface 606 may be used when the surgeon determines a compression force should be supplied to the handle 600; such as when positioning the implant facsimile within the vertebral space to determine implant size.

With reference now to FIGS. 26-30, the surgical instrumentation according to some aspects of the present teaching may include an inserter 900 having a distal end portion 902, a proximal end portion 904 and, a longitudinal length 932. The outer surface of the proximal end portion 904 may serve as a handle for the surgeon and may include a grip surface 914 to improve this function. The outer surface of the distal end portion 902 may include markings to assist the surgeon in properly positioning the inserter 900 during surgery. The markings may include numerals 906 and/or lines 908 that indicate measurements (such as inches or centimeters) so that the surgeon can easily see how the inserter 900 is being positioned with respect to the patient. The markings may include lines 910 and 1000 (see FIGS. 26, 27 and 29) to indicate proper insertion angle 1002, shown in FIG. 29. In one example, the proper insertion angle 1002 is 25 degrees with respect to a plain 1004 that intersects the middle of the patient's spinal segment and is perpendicular to the operating table. Lines 910, 1000 may be predetermined to be parallel and perpendicular, respectively, with respect to the plain 1004 when the correct insertion angle 1002 is achieved to assure the surgeon that alignment is correct. The markings may include a line 912 that is used for implant deployment as will be discussed further below.

With reference now to FIGS. 26-33, the inserter 900 may be a tube having internal channels used to receive later to be described surgical instruments. In some embodiments, seen best in FIGS. 31 and 33, the inserter 900 has two distinct longitudinally extending channels 920, 922 that extend for at least most of the longitudinal length 932 to openings at the proximal and distal ends of the inserter 900. The channels 920, 922 may be separated by a wall 924 that may serve as a barrier between the channels 920, 922 preventing surgical instruments received in one channel from contacting surgical instruments simultaneously received in the other channel. A groove 928 may extend longitudinally in a wall of the distal end portion 902, providing an opening to the channel 920. The inserter 900 may be formed in any manner chosen with the sound judgment of a person of skill in the art. For the embodiments shown in FIG. 32, a grip 934 receives shaft 936 and an impact cap 938 is inserted within the grip 934. A rotational force converter 930 (FIG. 33), used as discussed below, may be positioned within the proximal end of channel 922, within the proximal end of the impact cap 938 in the embodiment shown.

Figure 33:
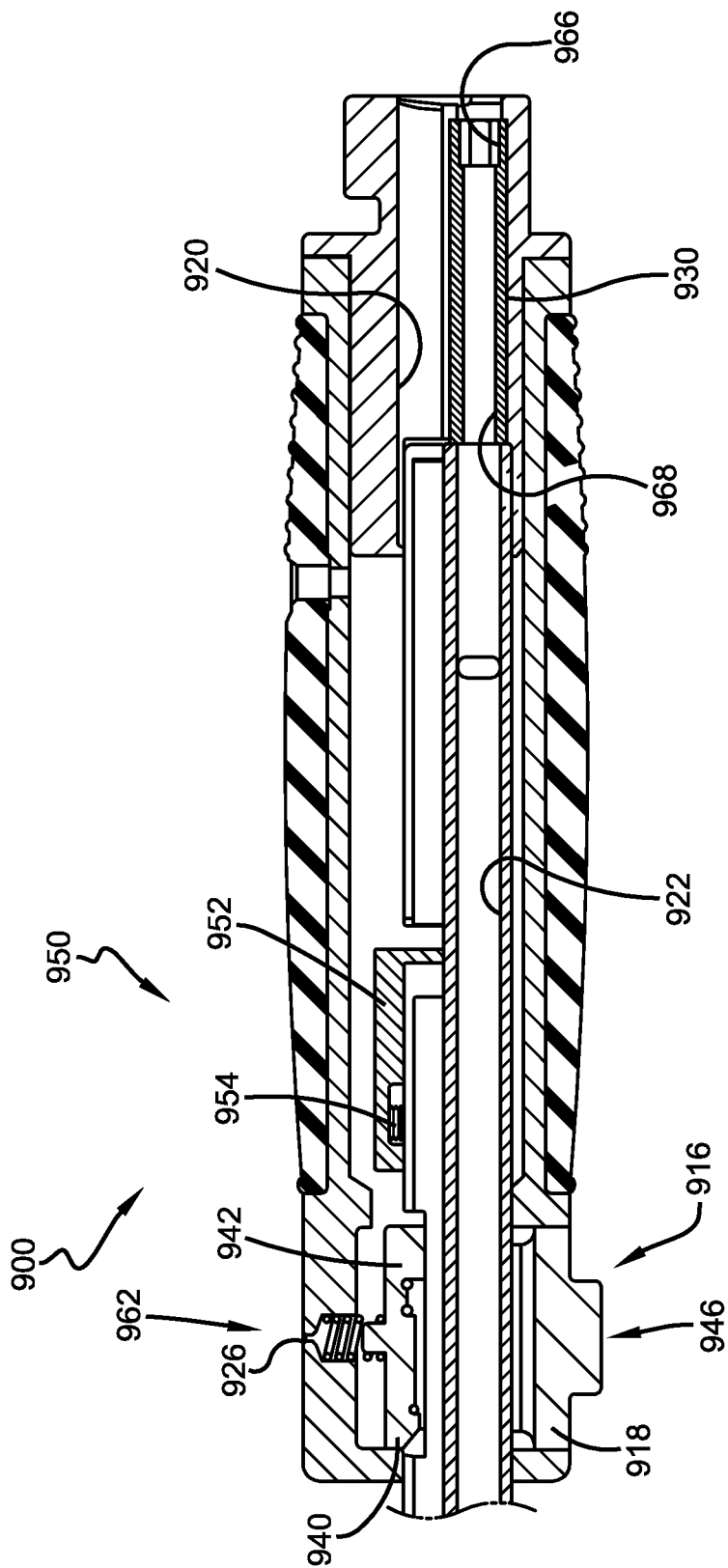
FIG. 33 is a side sectional view of a portion of an inserter.
Figure 34:
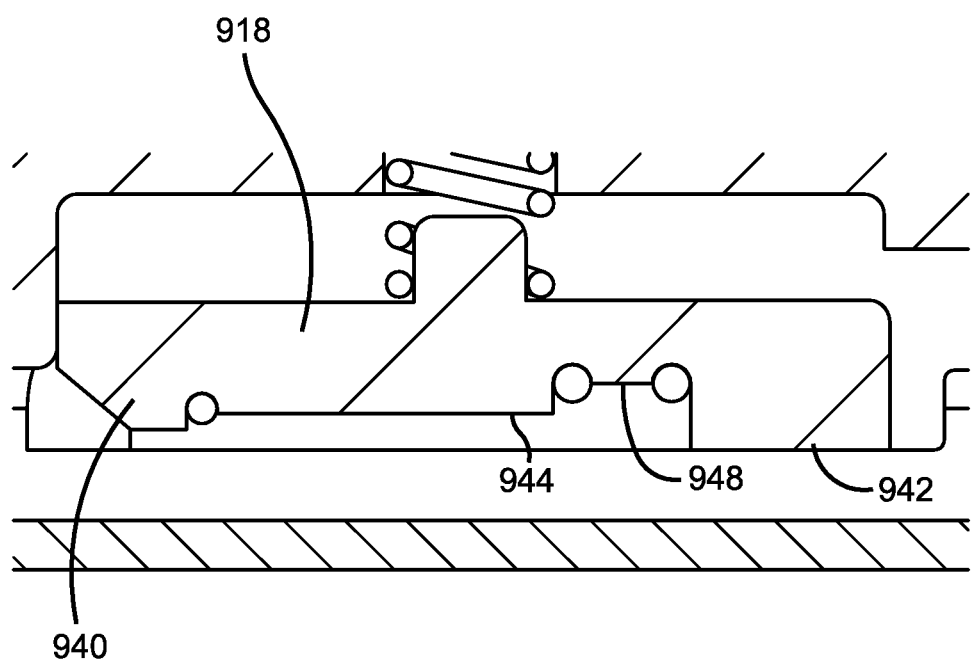
FIG. 34 is a close-up view of the movable button shown in FIG. 33.
Figure 35:
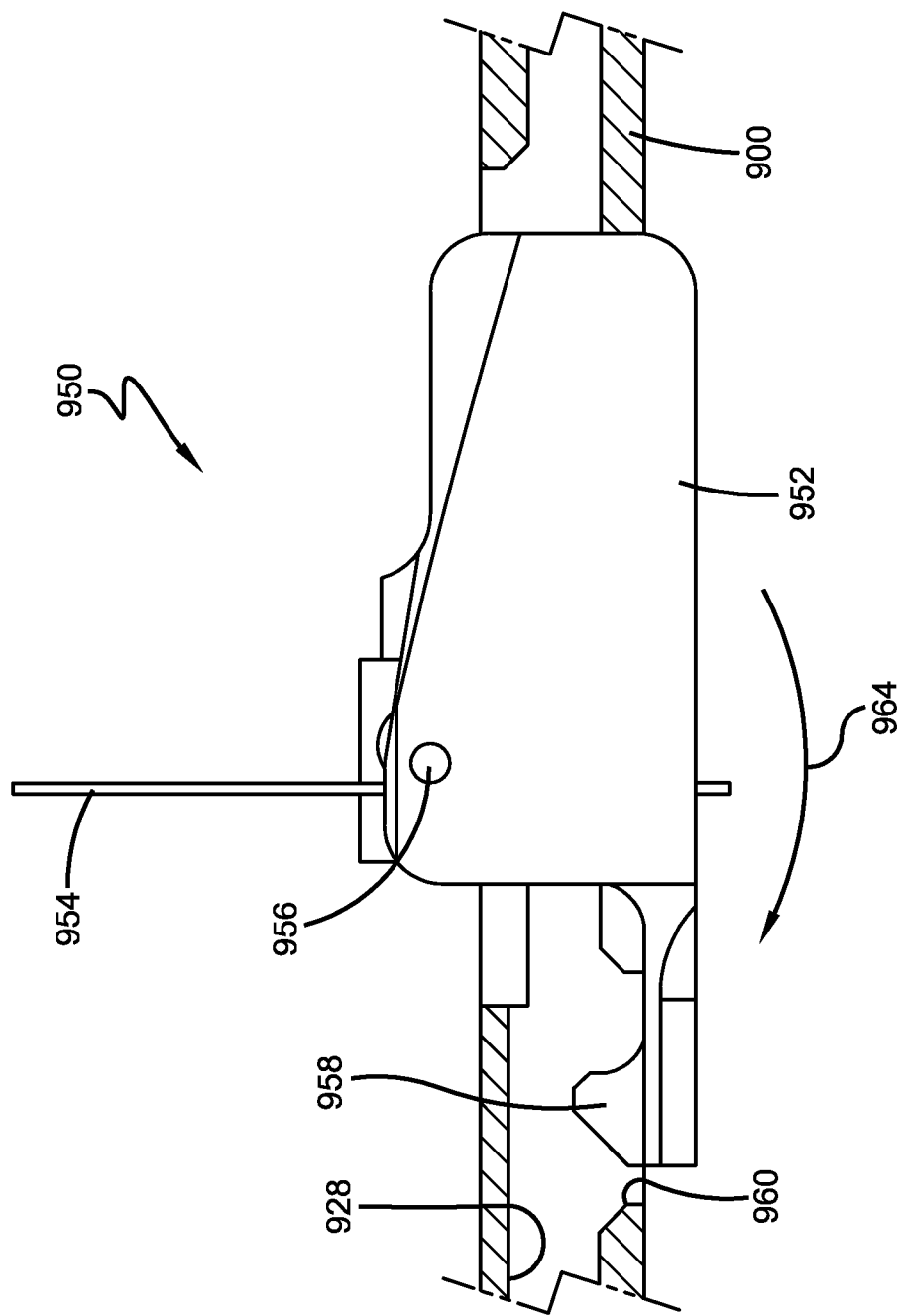
FIG. 35 is a top view of a latch mechanism.
Figure 36:
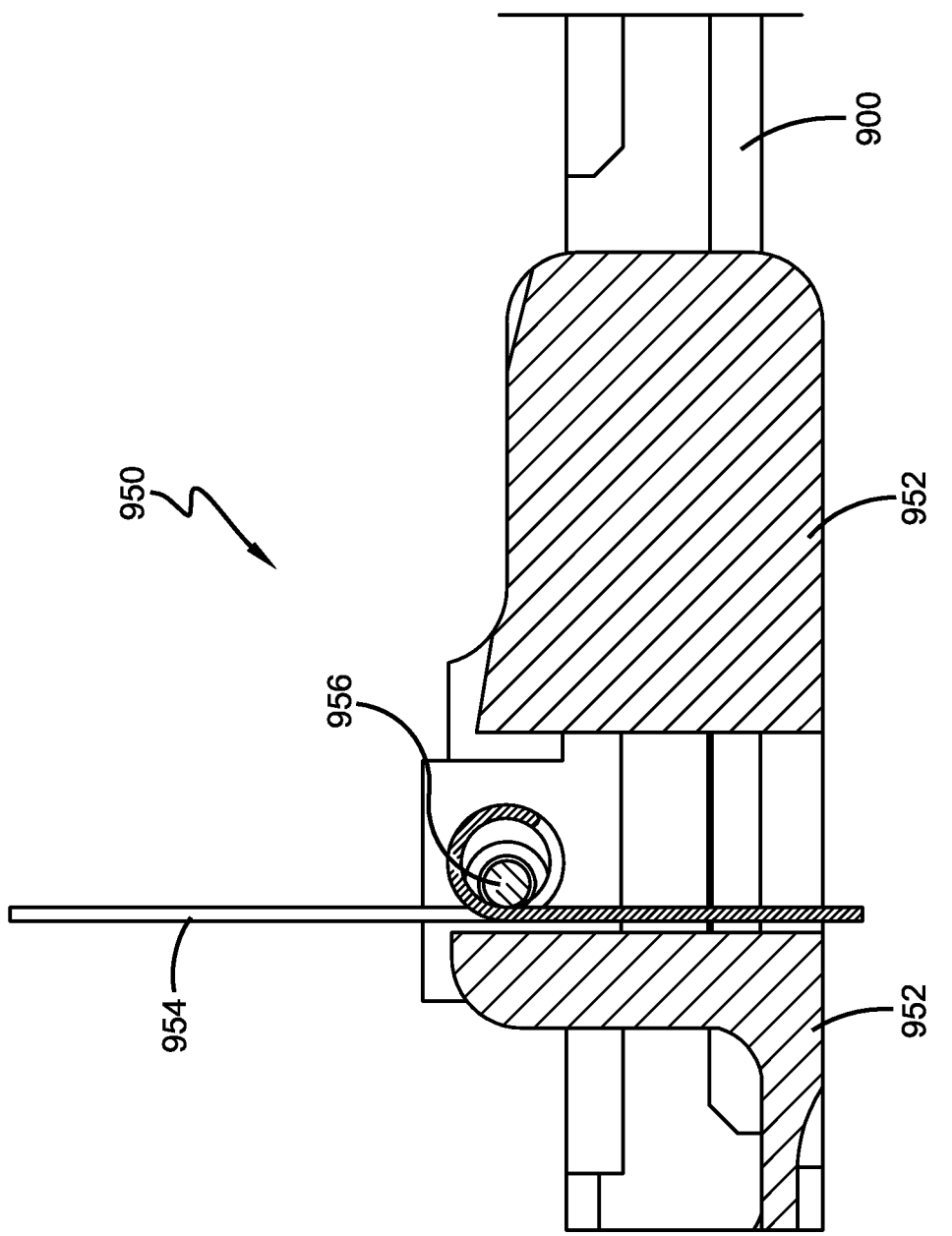
FIG. 36 is a view similar to that shown in FIG. 35 but with portions removed for clarity.
Figure 37:
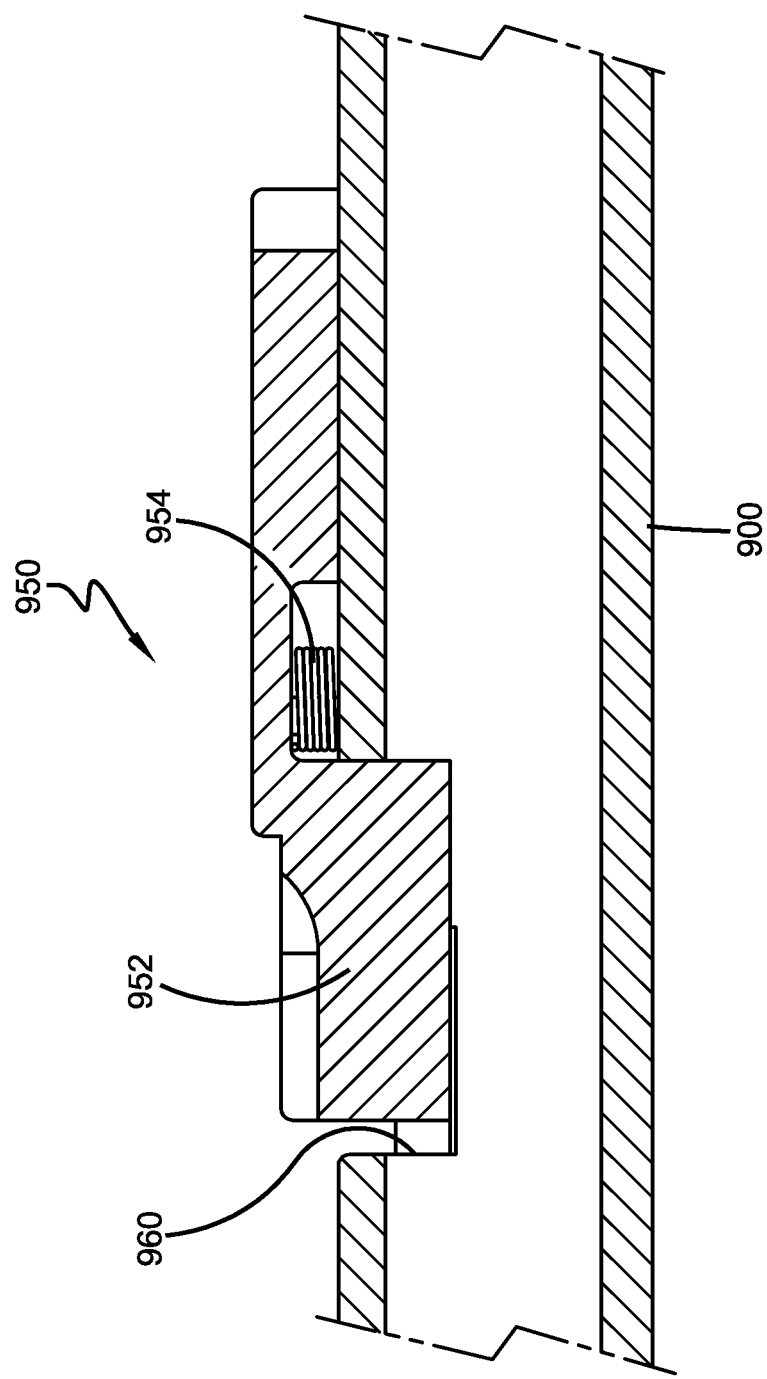
FIG. 37 is a side view of the latch mechanism shown in FIG. 35.
Figure 38:
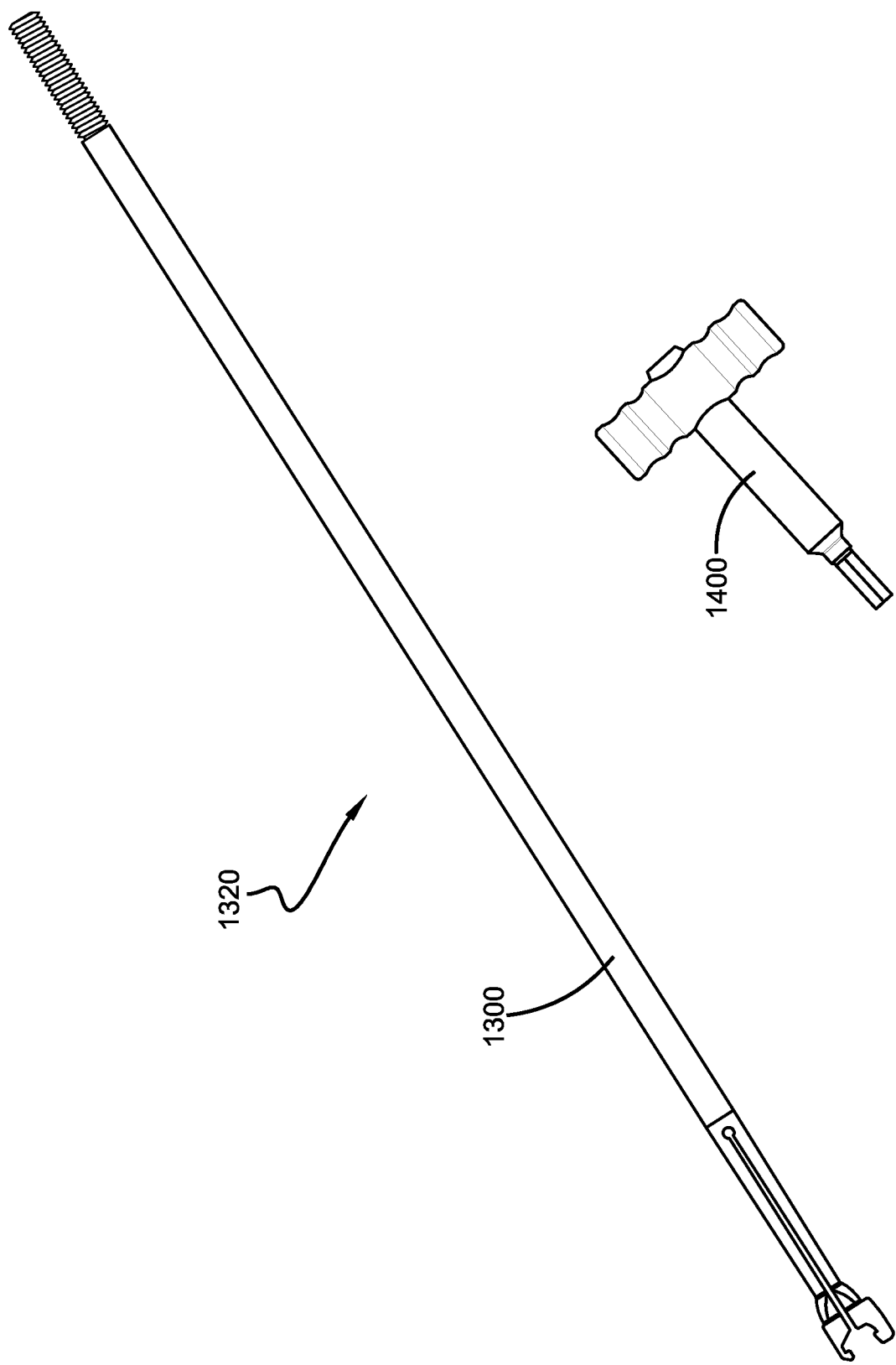
FIG. 38 shows an implant gripping mechanism.
Figure 42:
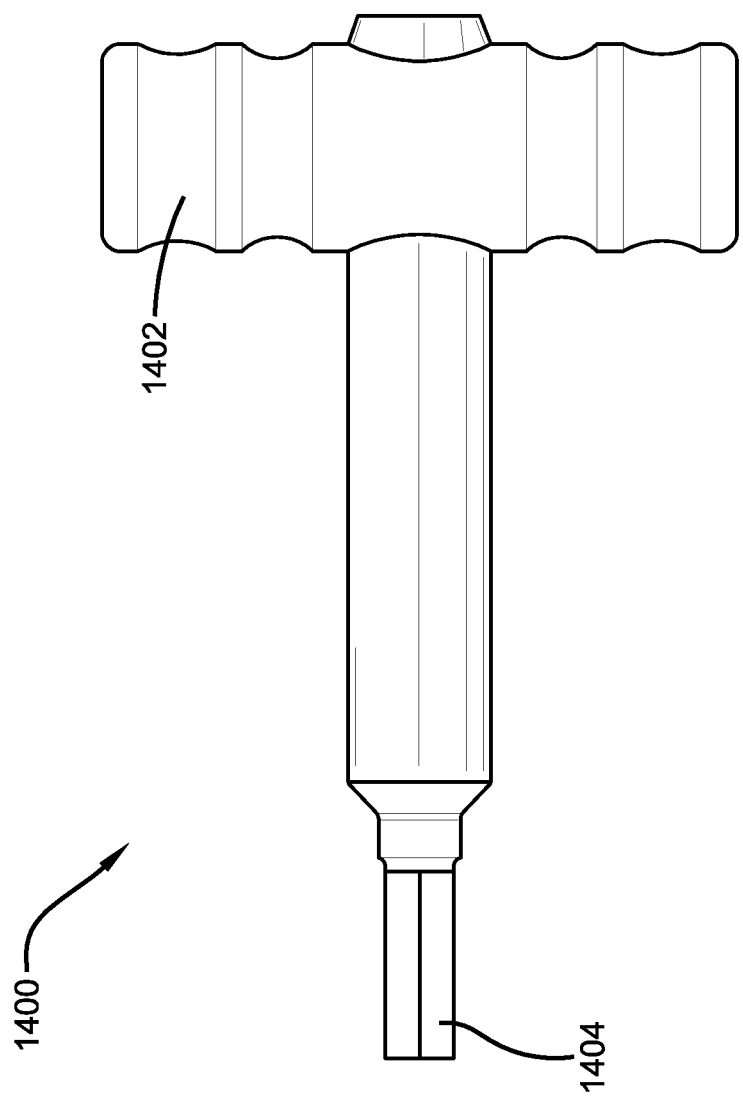
FIG. 42 is a side view of tool.

With reference now to FIGS. 26-28, 30 and 32-34, the inserter 900 may be equipped with one, and in some embodiments two, latch mechanisms that is/are used to engage surgical instruments to each other and/or to the inserter 900. Latch mechanism 916 may include a movable object 918 and a biasing device 926 that applies a biasing force to the movable object 918. In one embodiment, shown, the biasing device 926 is a compression spring. The movable object 918 may be a manually movable button 918, as shown. Button 918 may have, as shown in FIGS. 33-34, one side with a pair of tabs 940, 942 separated by a groove 944 and a second side with a contact surface 946. The groove 944 may have a cut-out portion 948. Latch mechanism 916 may be positioned within opening 948 (FIG. 32) in the inserter 900 with the biasing device 926 biasing the movable object 918 in direction 962 (FIG. 33) to bias contact surface 918 to extend out of the inserter 900, as shown.

With reference now to FIGS. 26 and 32-37, a latch mechanism 950 may include a movable object 952 and a biasing device 954 that applies a biasing force to the movable object 952. In one embodiment, shown, the biasing device 954 is a torsion spring. The movable object 952 may pivot about pin 956 and may have a tab 958. Latch mechanism 950 may be positioned on the inserter 900 with the biasing device 954 biasing the movable object 952 in direction 964 about pin 956 to bias tab 958 to extend into inserter opening 960, as shown. Latch mechanism 950 may be positioned within grip 934 proximal to latch mechanism 916, as shown. In embodiments where both latch mechanisms 916, 950 are used, it should be noted that the corresponding biasing forces bias tabs 940, 942 in a first direction (downward in FIGS. 27, 33 and into the page in FIG. 35) and bias tab 958 in a second direction (into the page in FIGS. 27, 33, 37 and upward in FIG. 35) that is at a right angle with respect to the first direction. As a result, the forces applied to the surgical instruments by the latch mechanisms are complementary.

With reference now to FIGS. 38-42, the surgical instrumentation according to some aspects of the present teaching of this invention may include an implant gripping mechanism 1320 used to grip or hold the implant and to release the implant. The gripping mechanism 1320 may include, in some embodiments, a gripping device 1300, a tool 1400 and the previously mentioned rotational force converter 930 (shown in FIG. 33). The gripping device 1300 may be an axle that extends longitudinally, as shown, and may have a distal end with a gripper 1302. The gripper 1302 may include a pair of opposing jaws 1304, 1304. The jaws 1304, 1304 may be designed to grip a portion of the implant and may be separated by a slot 1306 that extends proximally along the axle, as shown. A pair of markings 1308, 1310 may be positioned along the longitudinal axis of the gripping device 1300, as shown. The proximal end of the gripping device 1300 may include a connection surface 1312. According to some aspects of the present teaching of this invention, the connection surface 1312 may include threads on the outer surface of the gripping device 1300, as shown.

Figure 43:
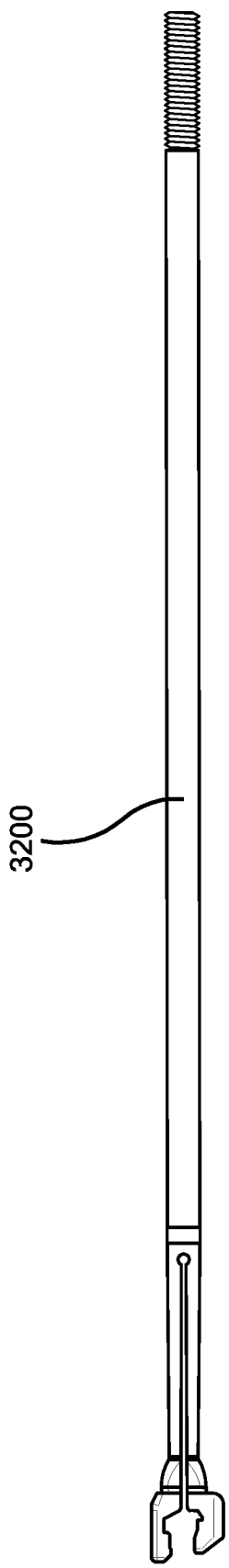
FIG. 43 is a side view of a gripping device 3200.
Figure 45:
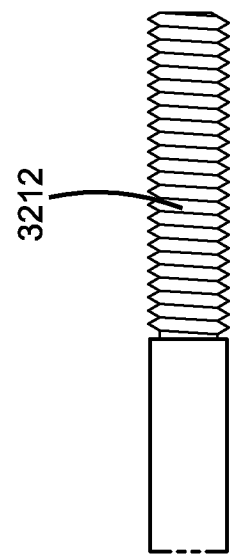
FIG. 45 is a close-up view of the proximal end of the gripping device shown in FIG. 43.
Figure 44:
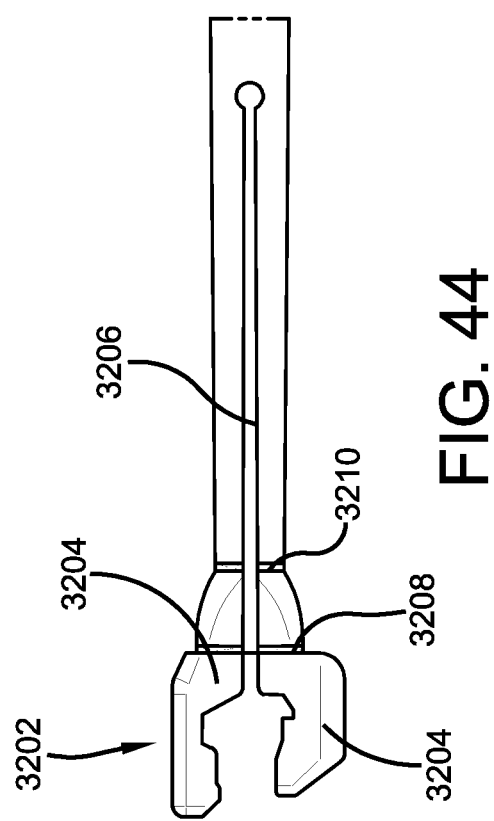
FIG. 44 is a close-up view of the distal end of the gripping device shown in FIG. 43.
Figure 47:
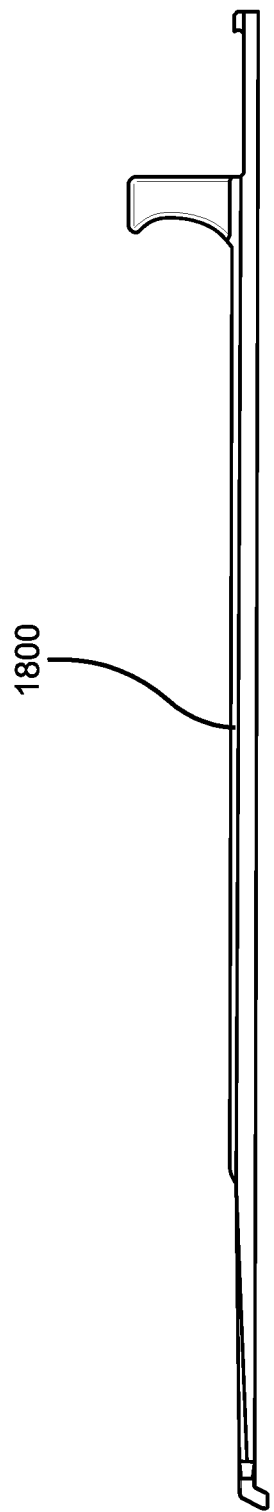
FIG. 47 is a side view of an inserter tamp.

With reference now to FIGS. 43-45, the surgical instrumentation according to some aspects of the present teaching of this invention may include an alternate gripping device 3200. Gripping device 3200 may, in some circumstances, be better suited for use in removing an implant from the vertebral space than gripping device 1300 described above. The gripping device 3200 may be an axle that extends longitudinally, as shown, and may have a distal end with a gripper 3202. The gripper 3202 may include a pair of opposing jaws 3204, 3204. The jaws 3204, 3204 may be designed to grip a portion of the implant and may be separated by a slot 3206 that extends proximally along the axle, as shown. The jaws 3204, 3204 may have a different shape than the jaws 1304, 1304 of the gripping device 1300 (FIG. 40) and may provide a wider mouth to make re-engagement to the implant in a constricted space (such as a vertebral space) easier for the surgeon. A pair of markings 3208, 3210 may be positioned along the longitudinal axis of the gripper 3200, as shown. The proximal end of the gripper 3200 may include a connection surface 3212. According to some aspects of the present teaching, the connection surface 3212 may include threads on the outer surface of the remover collet 3200, as shown.

With reference now to FIGS. 33 and 38-45, the tool 1400 may be used to adjust the gripping device 1300 via the rotational force converter 930. The tool 1400 may have a proximal end with a handle 1402 used by the surgeon when using the tool and a distal end with a connection surface 1404. The rotational force converter 930 may have a proximal end with a connection surface 966 designed to engage the connection surface 1404 of the tool 1400 and a distal end with a connection surface 968 designed to engage the connection surface 1312 of the gripping mechanism 1300. In one non-limiting embodiment, shown, the connection surface 1404 of the tool 1400 is a male hex wrench head that is received in a female hex wrench opening formed in the connection surface 966 of the rotational force converter 930 and the threaded connection surfaces 1312, 3212 of the gripping devices 1300, 3200 are received in a matching threaded opening formed in the connection surface 968 of the rotational force converter 930.

Figure 49:
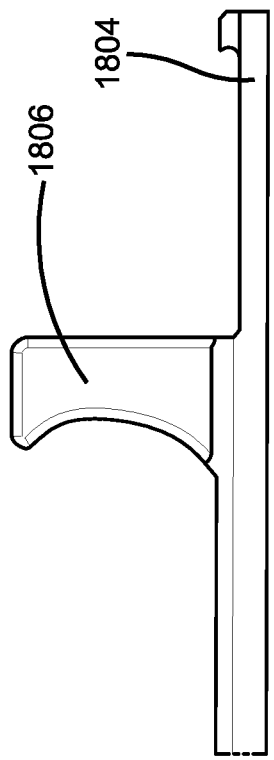
FIG. 49 is a close-up view of the proximal end of the inserter tamp shown in FIG. 47.
Figure 48:
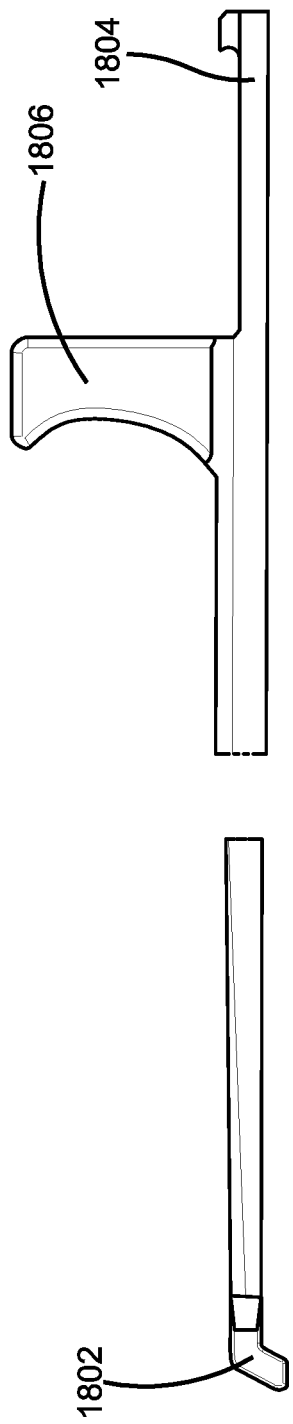
FIG. 48 is a close-up view of the distal end of the inserter tamp shown in FIG. 47.

With reference now to FIGS. 46-50, the surgical instrumentation according to some aspects of the present teaching of this invention may include an implant deployment mechanism 1500 used to deploy the implant. The implant deployment mechanism 1500 may include, in some embodiments, an inserter tamp 1800 and an impactor 2200. The inserter tamp 1800 may extend longitudinally, as shown, and may include a distal end with a contact surface 1802. The contact surface 1802 may extend downwardly, as shown in FIGS. 46 and 48. The proximal end of the inserter tamp 1800 may include a connection surface 1804. The connection surface 1804 may include a groove 1808 extending to a tab 1810. The tab 1810 may extend upwardly, as shown in FIGS. 46 and 49. A trigger 1806 may extend upwardly, as shown. Multiple sizes of inserter tamps may be provided to correspond to multiple implant sizes. Markings may be provided on the trigger 1806, as shown, to indicate the size of the inserter tamp. The impactor 2200 may extend longitudinally, as shown, and may include a distal end with a connection surface 2202 and a proximal end with a contact surface 2204. The connection surface 2202 may include a groove 2210 extending to a tab 2212. The tab 2212 may extend upwardly, as shown in FIG. 46. The impactor 2200 may include markings 2206 and 2208. The marking 2208 may indicate the size of the impactor so that the surgeon can choose the impactor corresponding to the implant to be deployed.

Figure 51:
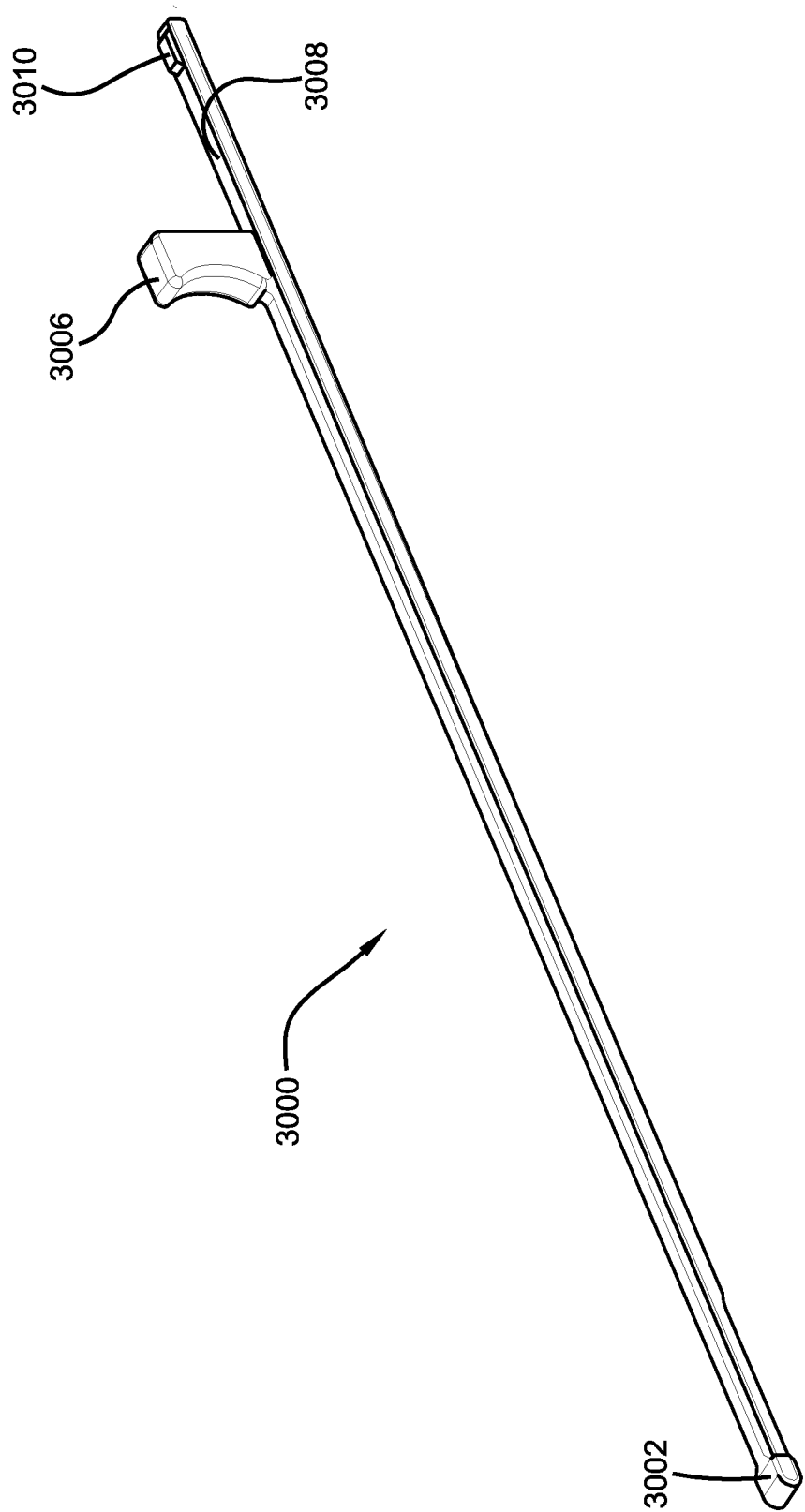
FIG. 51 is a perspective view of remover tamp.
Figure 52:
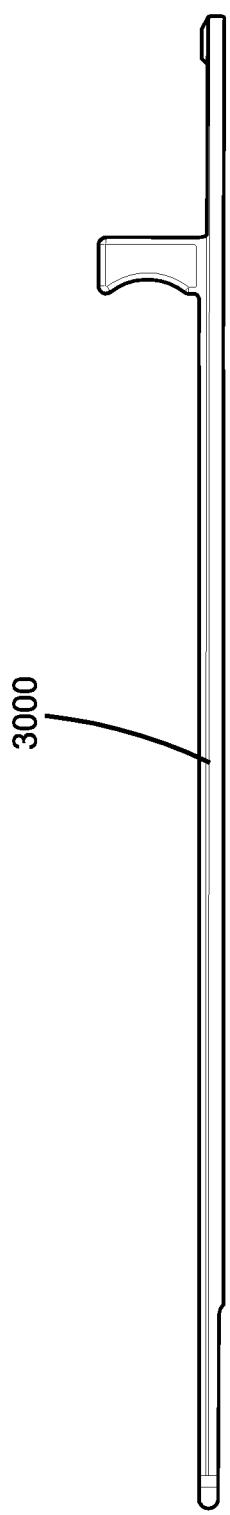
FIG. 52 is a side view of a remover tamp.
Figure 54:
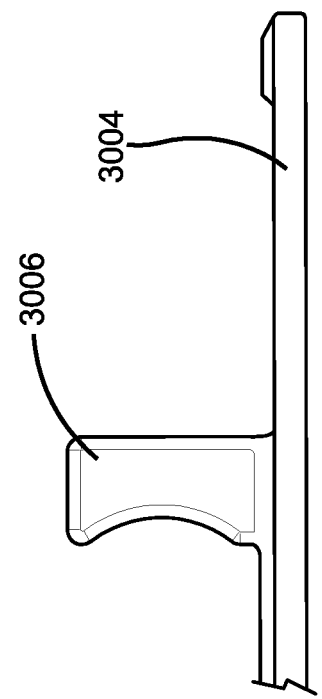
FIG. 54 is a close-up view of the proximal end of the remover tamp shown in FIG. 52.
Figure 53:
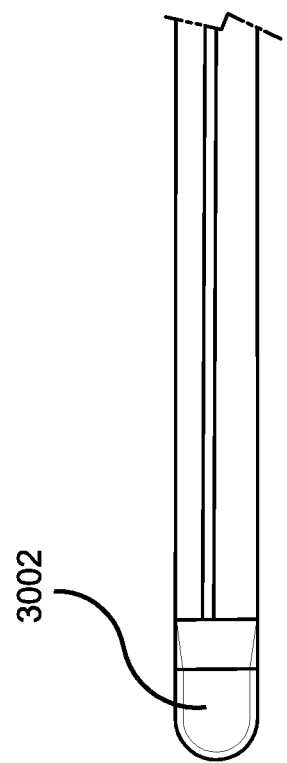
FIG. 53 is a close-up view of the distal end of the remover tamp shown in FIG. 52.

With reference now to FIGS. 51-54, the surgical instrumentation according to some aspects of the present teaching of this invention may include a remover tamp 3000. The remover tamp 3000 may extend longitudinally and may include a distal end with a contact surface 3002. The contact surface 3002 may extend distally as shown. The proximal end of the remover tamp 3000 may include a connection surface 3004. The connection surface 3004 may include a groove 3008 extending to a tab 3010. The tab 3010 may extend upwardly, as shown in FIGS. 51 and 54. A trigger 3006 may extend laterally, as shown. Multiple sizes of remover tamps may be provided to correspond to multiple implant sizes. Markings may be provided on the trigger, as shown, to indicate the size of the remover tamp. The remover tamp 3000 may be a little longer than the inserter tamp 1800 (FIGS. 46-49). In one embodiment, the distance from the proximal end of trigger 3006 to the proximal end of the remover tamp 3000 is greater than the distance from the proximal end of trigger 1806 to the proximal end of inserter tamp 1800.

Figure 55:
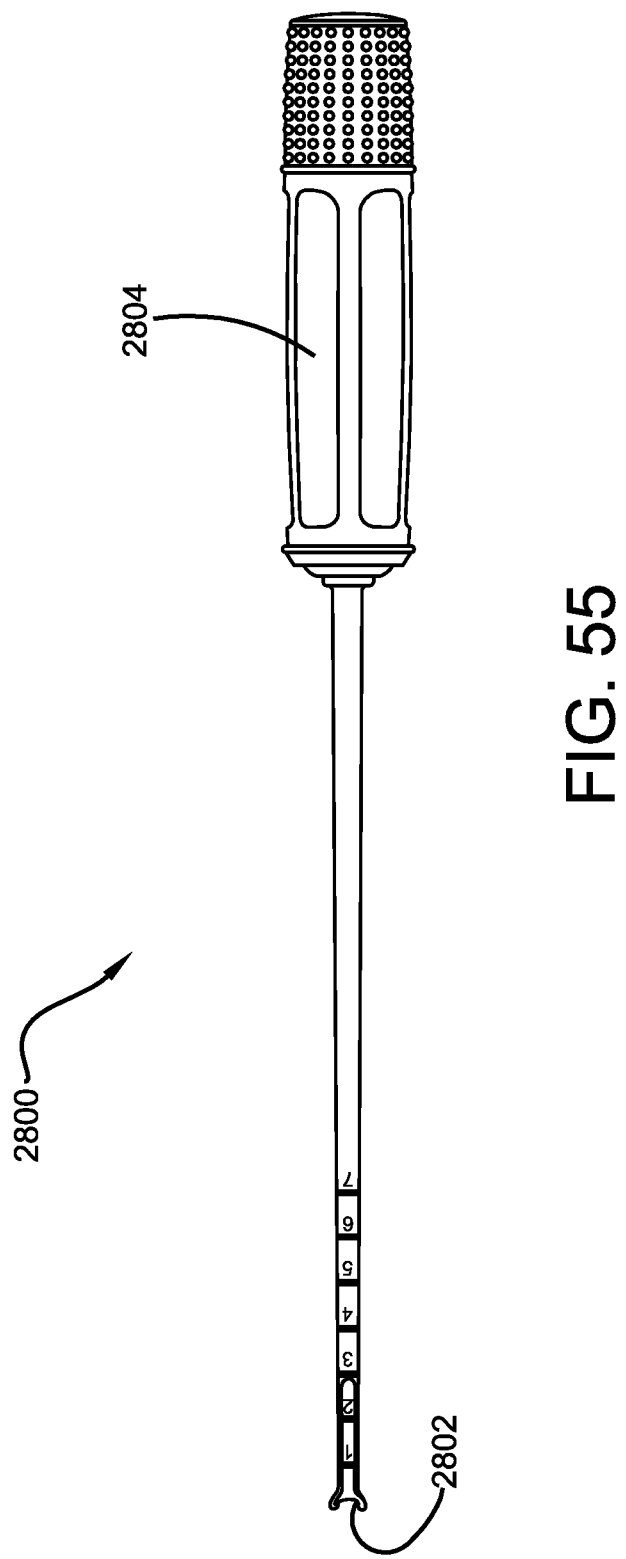
FIG. 55 is a side view of a freehand tamp.
Figure 56:
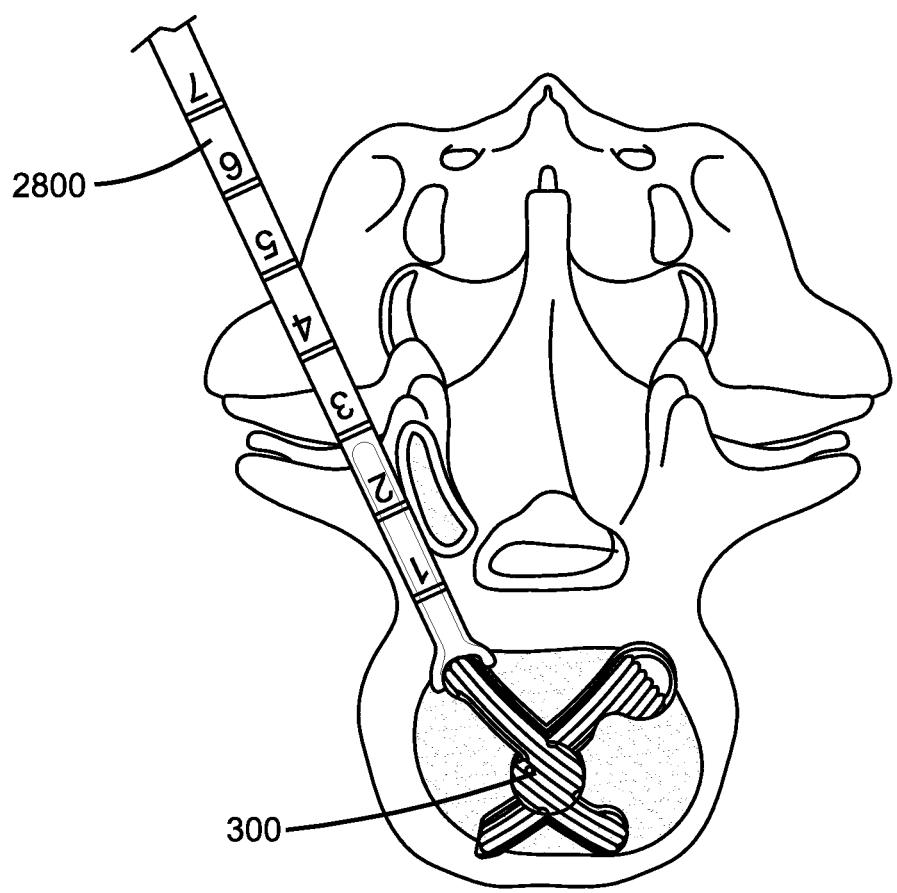
FIG. 56 illustrates a freehand tamp being used to adjust the position of an implant within a vertebral space.

With reference now to FIGS. 55-56, the surgical instrumentation according to some aspects of the present teaching of this invention may include a freehand tamp 2800. The freehand tamp 2800 may extend longitudinally, as shown, and may include a distal end with a contact surface 2802 and a proximal end with a handle 2804. The contact surface 2802 may be sized and shaped to match an outer surface of the implant 300 as shown in FIG. 56.

In what follows, the use of spinal implants and surgical instrumentation according to numerous embodiments will be described. Once the vertebral space 114, 212 (FIGS. 1 and 2) is prepared (including completion of distraction and endplate preparation), trials 400 (FIG. 21) may be used to determine the proper implant 300 size, as discussed above.

Figure 57:
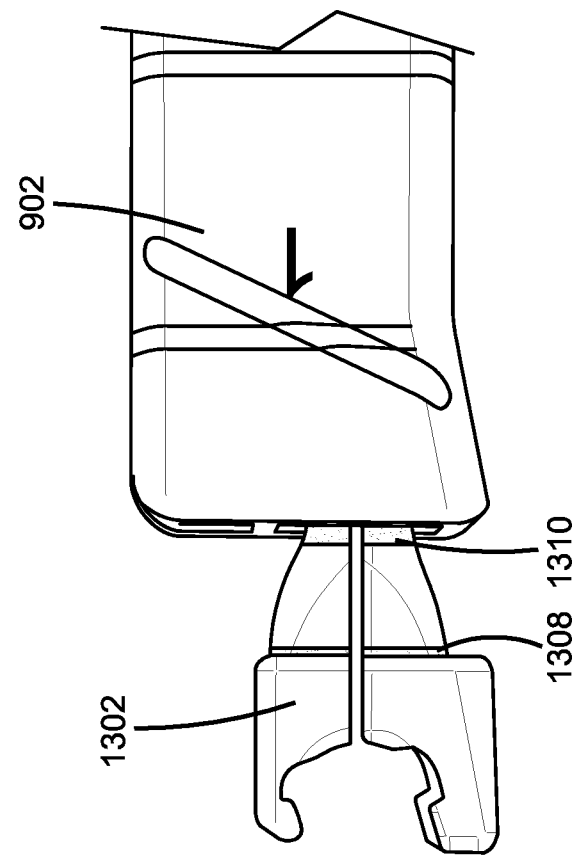
FIG. 57 is a close-up side view of the distal end of an inserter receiving a gripping device.
Figure 58:
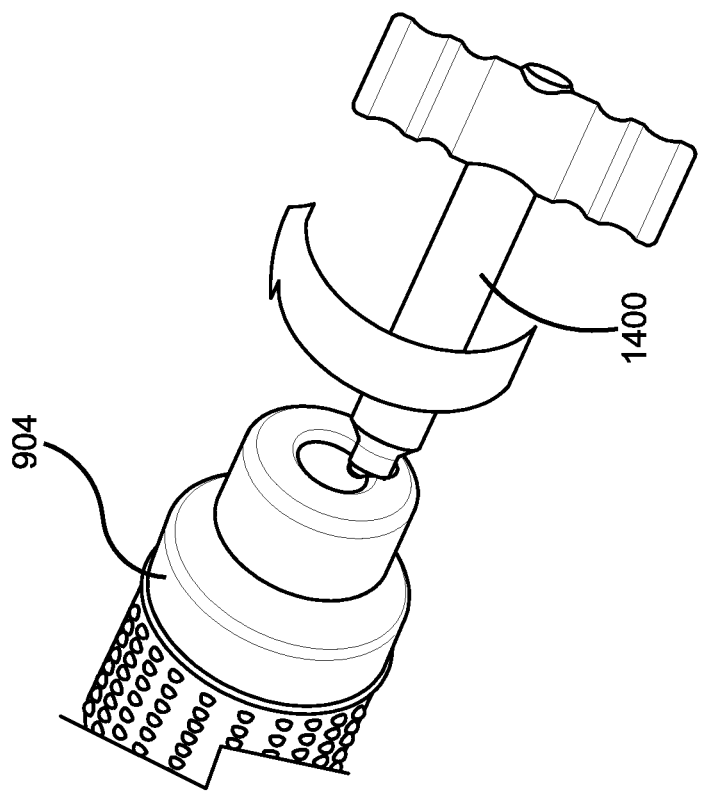
FIG. 58 is a close up perspective view of the proximal end of an inserter receiving a tool.
Figure 59:
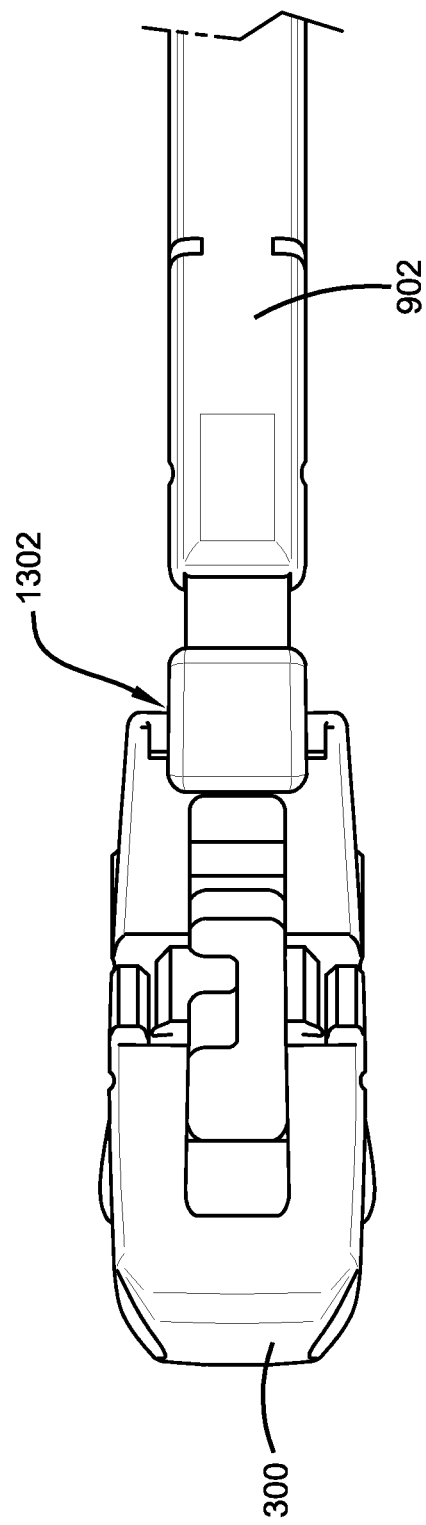
FIG. 59 is a side view showing an implant gripper gripping a spinal implant.
Figure 60:
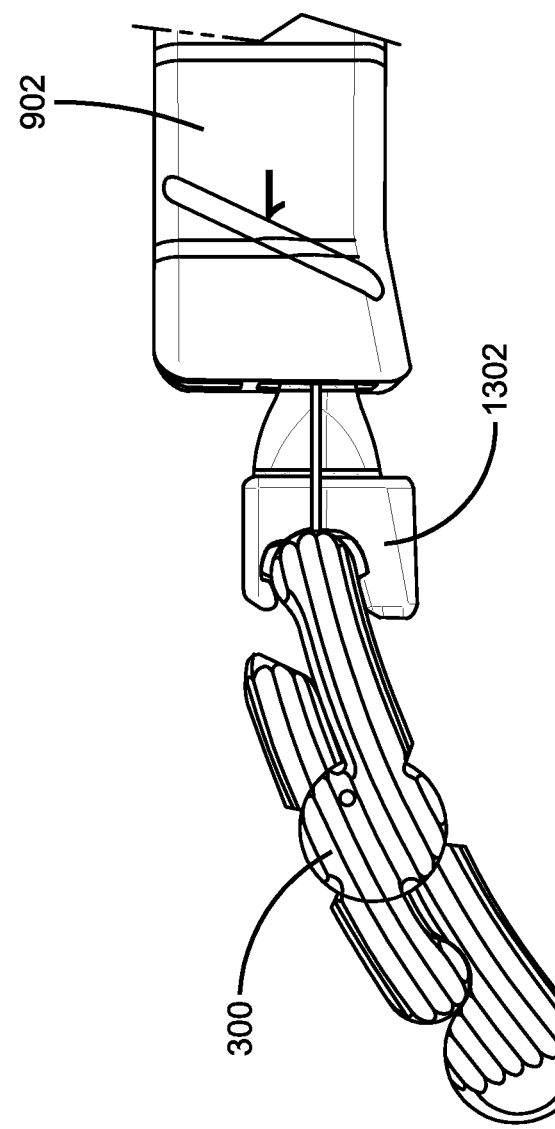
FIG. 60 is a top view of the implant gripper gripping a spinal implant shown in FIG. 59.
Figure 61:
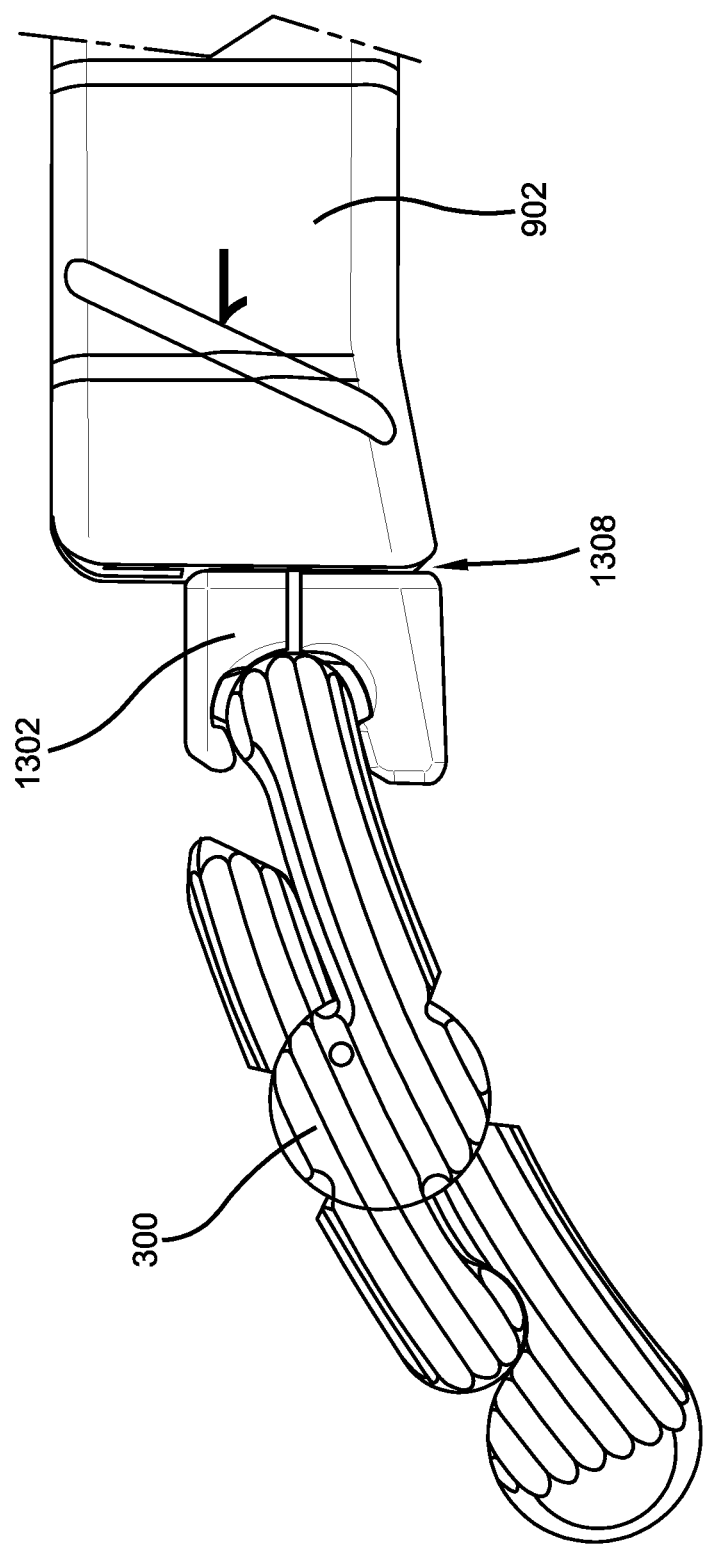
FIG. 61 is a top view of an implant gripper gripping a spinal implant.

With reference now to FIGS. 26, 33, 38-42 and 57-61, in order to grip the implant 300 with the implant gripping mechanism 1320, the gripping device 1300 may be attached to the inserter 900. Specifically, the proximal end of the gripping device 1300 may be inserted into the distal end of channel 922 with connection surface 1312 engaging connection surface 968 of the rotational force converter 930. The distal end of the tool 1400 may then be inserted into the proximal end of channel 922 with connection surface 1404 of the tool 1400 engaging connection surface 966 of the rotational force converter. The tool 1400 may then be rotated in a clockwise direction as indicated in FIG. 58. This rotation may cause the rotational force converter 930 to rotate in the same direction drawing the gripping device 1300 further into the inserter channel 922. The gripping device 1300 may be drawn into the inserter 900 until marking 1310 is aligned with the distal end of the distal end portion 902, as shown in FIG. 57. A portion of the implant 300, as shown in FIGS. 59-60, may then be centered and inserted within the gripper jaws 1304, 1304. The tool 1400 may then be rotated further in the clockwise direction, as shown in FIG. 58, until marking 1308 aligns with the distal end of the distal end portion 902 as shown in FIG. 61. This motion may cause the slot 1306 (FIG. 40) to narrow so that the gripper 1302 firmly grips the implant 300. In this way the tool 1400 can be used to adjust the gripper 1302 to grip the implant 300. Note that in the embodiment shown, the implant 300 is now juxtaposed to the distal end of the channel 922. With this arrangement, the implant 300 may be considered properly seated with respect to the inserter 900.

Figure 62:
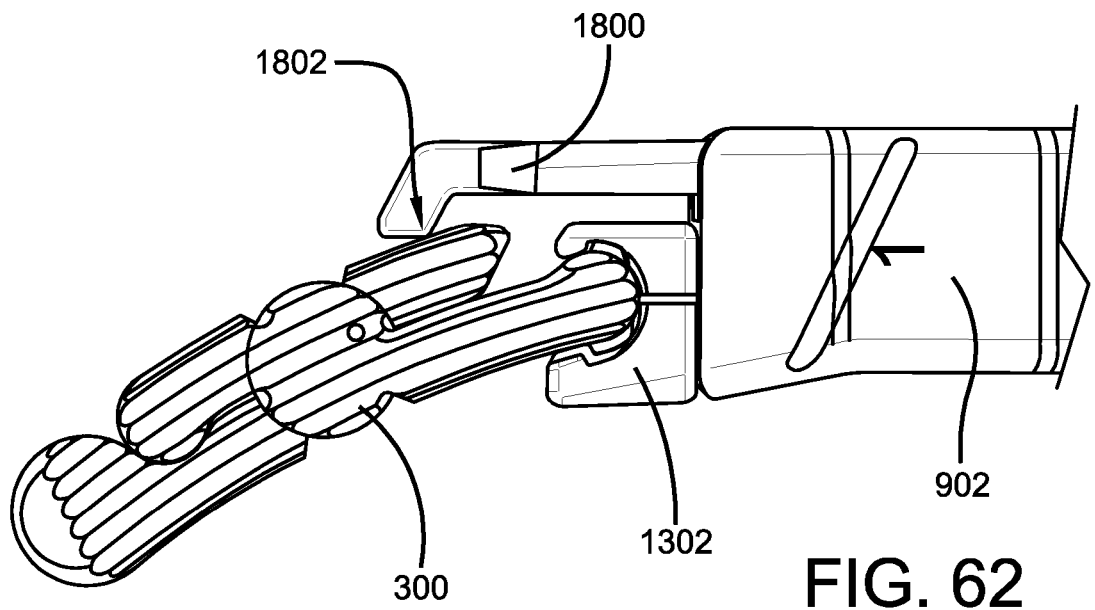
FIG. 62 is a top view of a gripper gripping a spinal implant and an inserter tamp inserter tamp holding the spinal implant in a collapsed condition.
Figure 63:
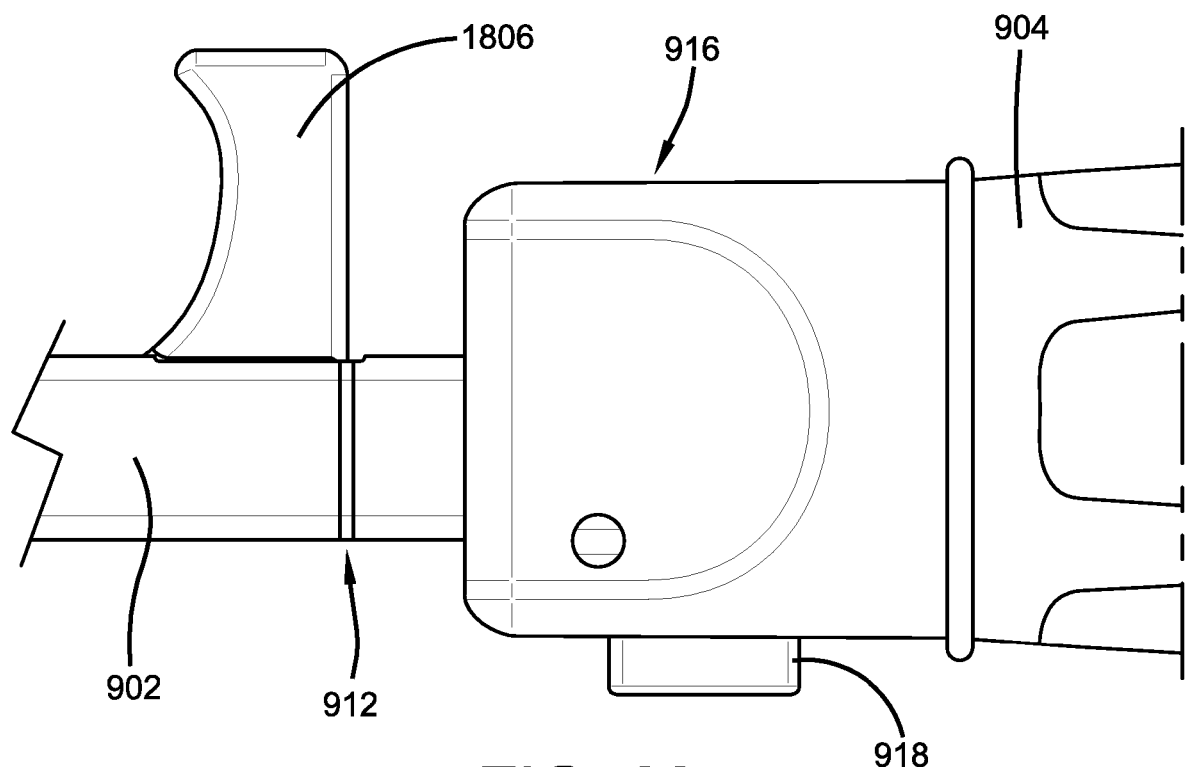
FIG. 63 is a close-up side view of a portion of an inserter receiving an inserter tamp.

With reference now to FIGS. 26, 33-37, 46-50 and 62-63, the implant deployment mechanism 1500 may be attached to the inserter 900. Specifically, the proximal end of the appropriate inserter tamp 1800 may be inserted into the distal end of channel 920 with trigger 1806 extending out of groove 928. As this insertion continues, connection surface 1804 may engage latch mechanism 916. Specifically, as the tamp 1800 is inserted, tab 1810 may contact tab 940 of the button 918, moving button 918 upward (in FIG. 33) overcoming the biasing force of biasing device 926 and the tab 1810 may then be received in groove 944 (while tab 940 is received in groove 1808) as the button 918 moves back downward (under the biasing force). The surgeon may hear an audible "click" as the tamp 1800 is latched to the inserter 900 in this way. Note that in some embodiments, one or both of the proximal end of tab 1810 and the distal end of tab 940 may be angled or curved to ease the contact between tabs 1810 and 940. For the embodiment shown in FIG. 34, the distal end of table 940 is angled for this purpose. The surgeon may then pull trigger 1806 (and thus tamp 1800) proximally to align the proximal edge of the trigger 1806 with the line 912 on the inserter as shown in FIG. 63. This motion may move tab 1810 into opening 948. Tab 1810 and opening 948 may be sized such that tab 1810 fits securely within opening 948. In this position the contact surface 1802 at the distal end of the inserter tamp 1800 contacts the implant 300, as shown in FIG. 62. This contact, along with the gripper 1302 holding a different part of the implant 300, as shown, maintains the implant 300 in the contracted or non-deployed condition. If the implant 300 is inadvertently locked into the expanded or deployed condition prior to insertion within the vertebral space, the implant 300 can be unlocked using lock release tool 800, as described above.

Figure 29:
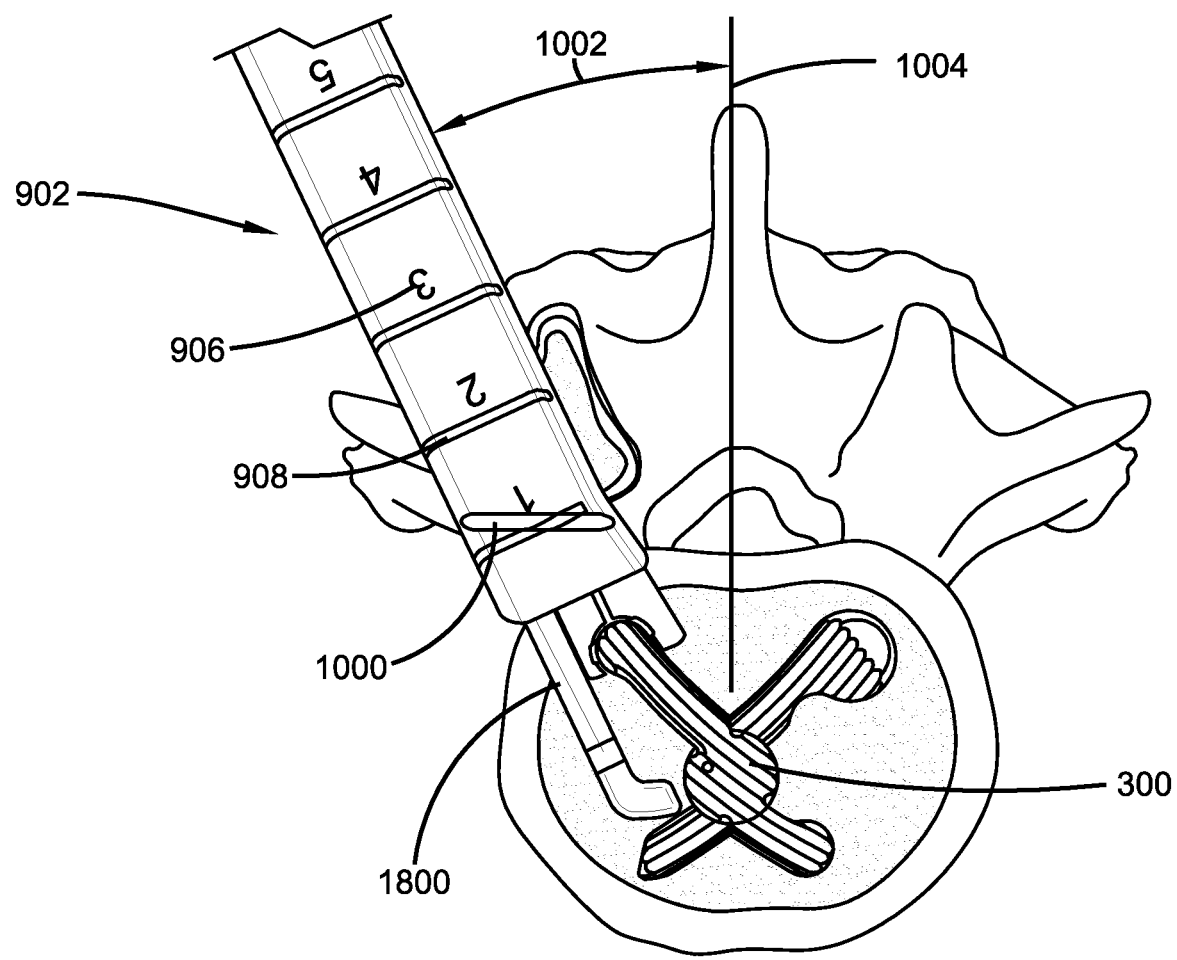
FIG. 29 illustrates an inserter being used to adjust an implant positioned within a vertebral space into a deployed condition.
Figure 30:
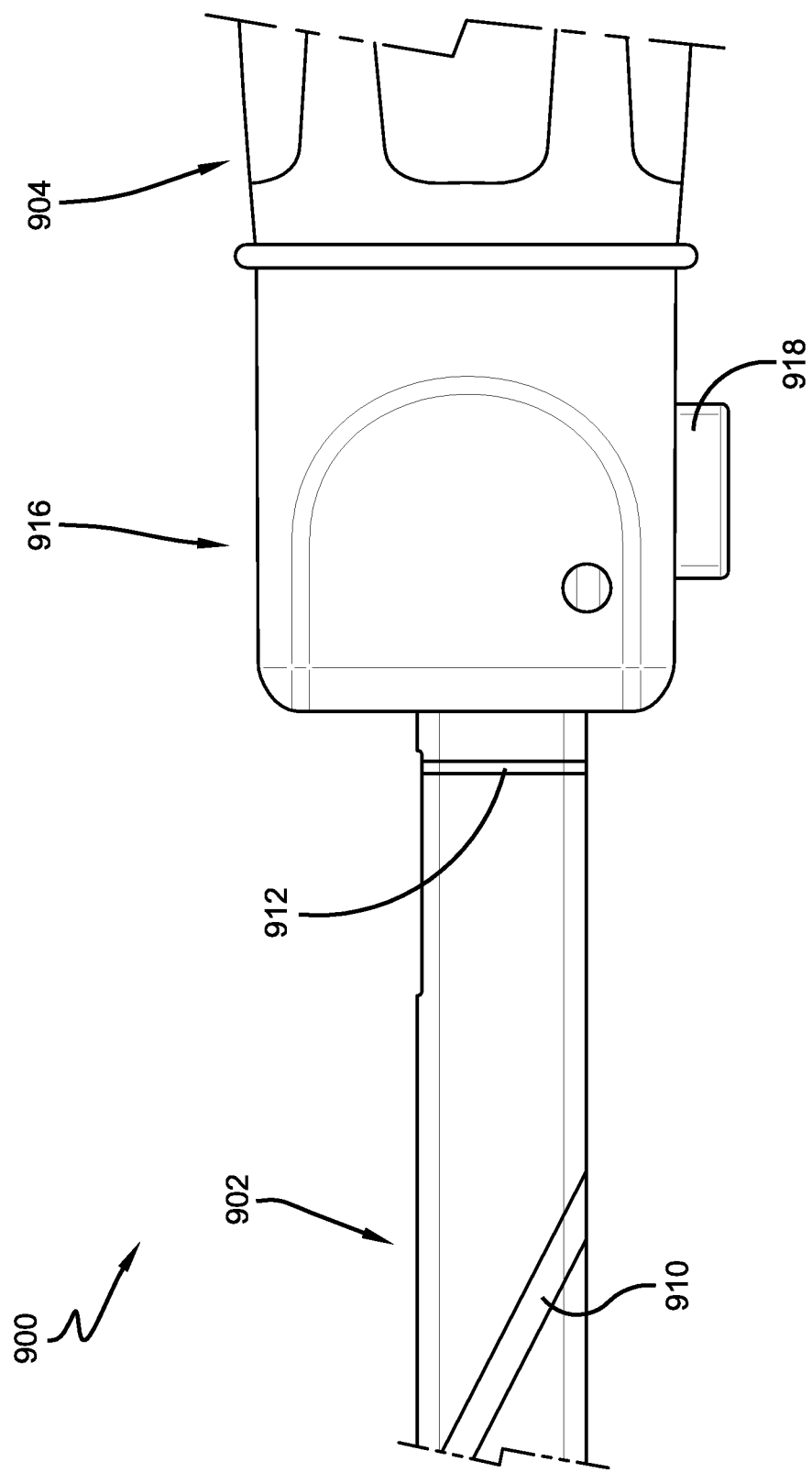
FIG. 30 is a close-up side view of a portion of the inserter shown in FIG. 26.
Figure 31:
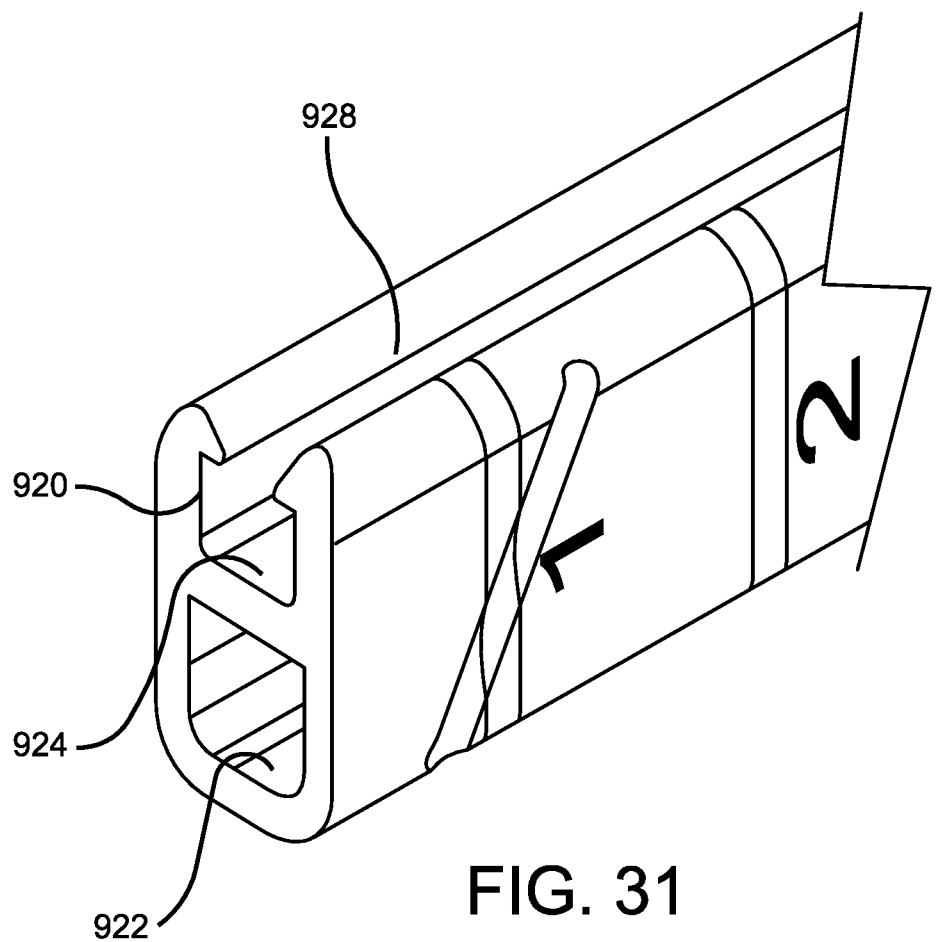
FIG. 31 is a close-up perspective view of the distal end view of an inserter.
Figure 32:
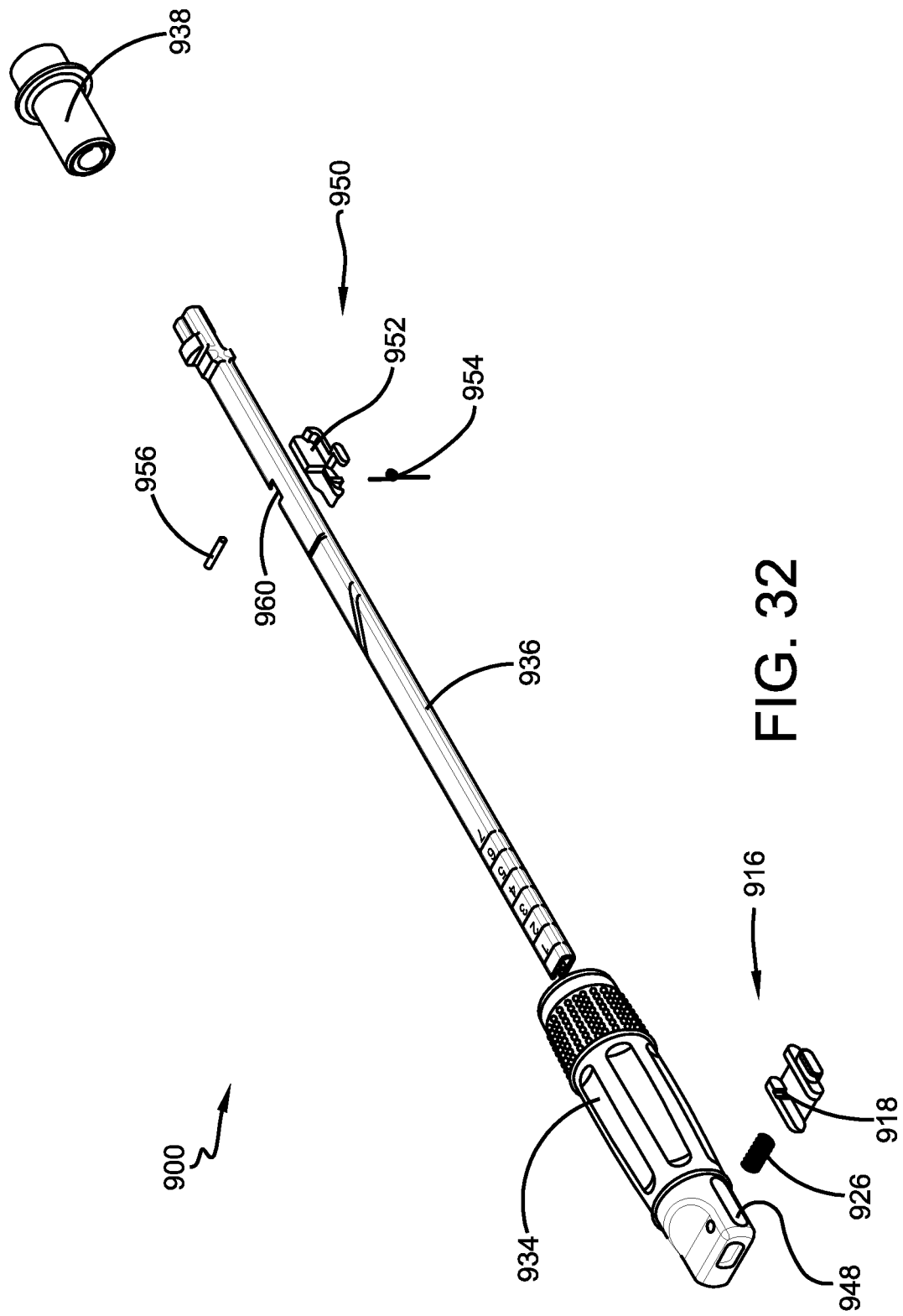
FIG. 32 is an assembly view of an inserter.
Figure 64:
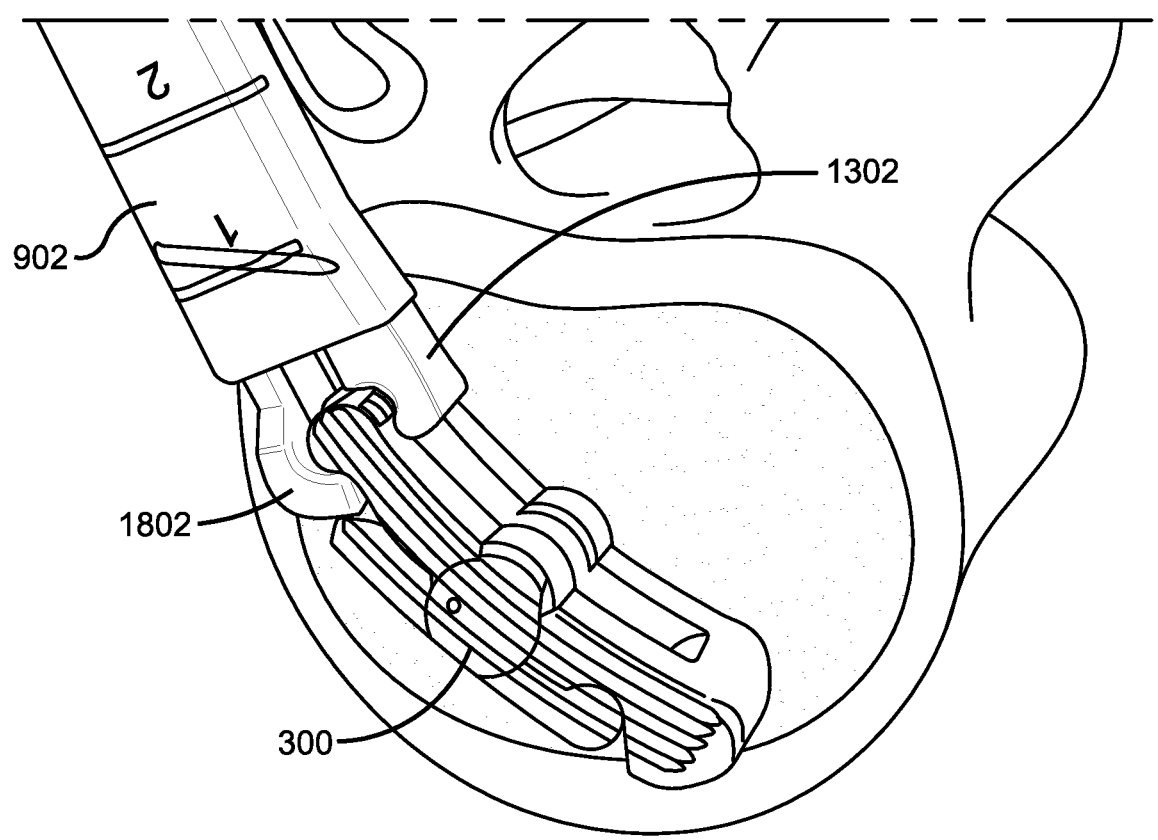
FIG. 64 illustrates an inserter being used to place a spinal implant within a vertebral space.
Figure 65:
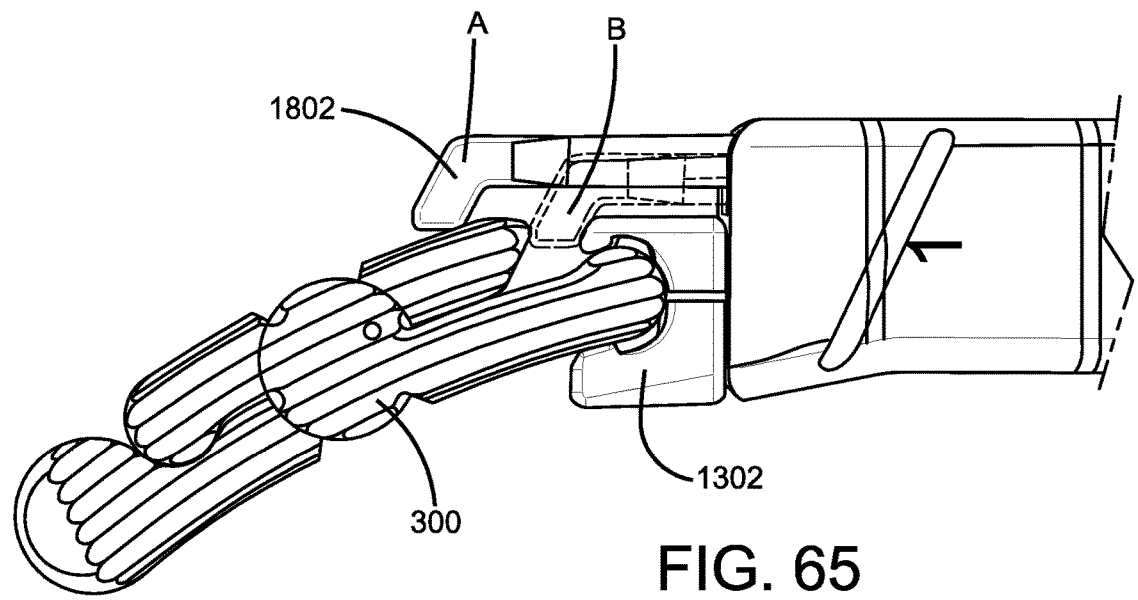
FIG. 65 is a top view of a gripper gripping a spinal implant and an inserter tamp being moved to enable implant deployment.
Figure 66:
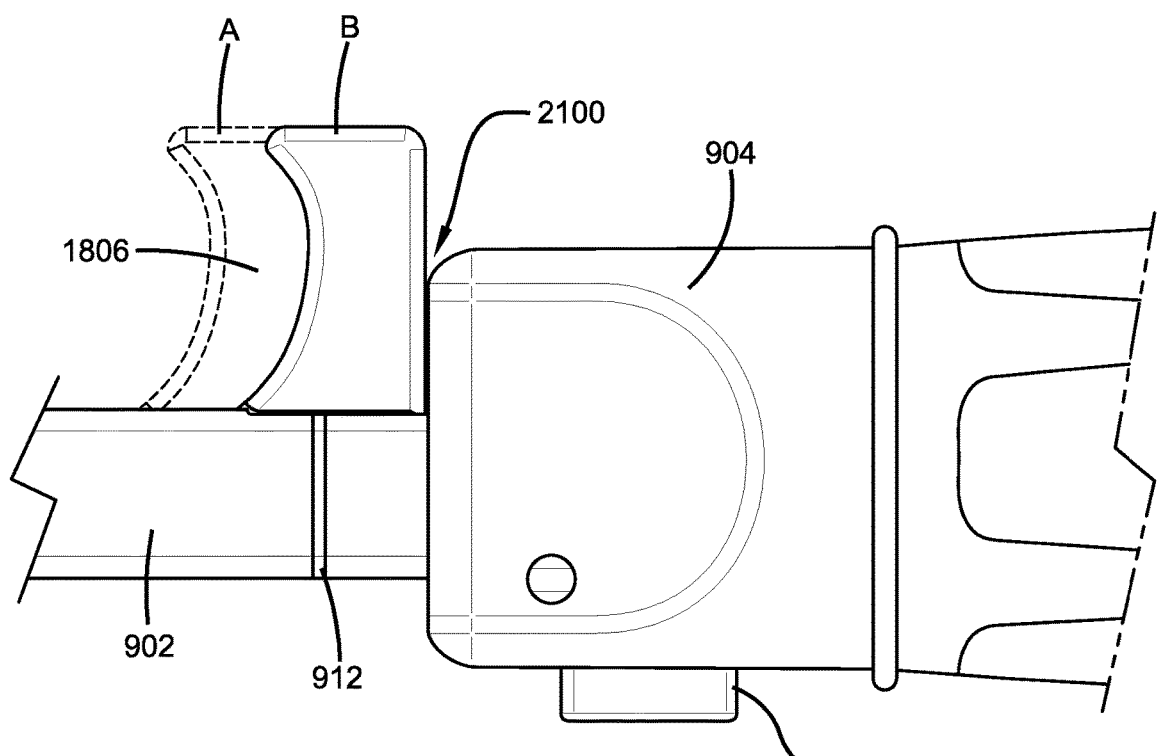
FIG. 66 is a close-up side view of a portion of an inserter and an inserter tamp being moved to enable implant deployment.

With the implant 300 properly attached to the inserter as shown in FIG. 62, the surgeon may insert the implant 300 to the proper location within the vertebral space, as illustrated in FIG. 64. Inserter markings lines 910 and 1000 (see FIGS. 26, 27 and 29) may be used to achieve proper insertion angle 1002 as shown in FIG. 29 and described above. To enable the implant 300 to be deployed within the vertebral space, the surgeon may adjust the inserter tamp 1800 out of the position where it holds the implant 300 in the contracted or non-deployed condition. This may be done by pressing contact surface 946 of button 918 inward against the biasing force (upward in FIG. 33) while simultaneously applying a proximal force to the trigger 1806 (and thus to the tamp 1800). This motion may move the trigger 1806 from position A to position B (FIG. 66) where the trigger 1806 contacts a distal surface of the proximal end portion 904 of the inserter 900 at location 2100. This motion may also move tamp tab 1810 under button tab 942. In some embodiments, this motion may also move tamp tab 1810 into contact with tab 958 of latch mechanism 950 (FIG. 35), pivoting object 952 while overcoming the biasing force of biasing device 954. This provides additional stability for holding the tamp 1800 in this position. This same motion of the tamp 1800 may simultaneously move the inserter tamp contact surface 1802 from position A to position B (FIG. 65). In this way, the contact surface 1802 no longer prevents the implant 300 from being deployed. Note that the latch mechanism 916 may prevent the tamp 1800 from being moved in this way unless the surgeon first manually adjust the latch mechanism 916 by pressing button 918.

Figure 68:
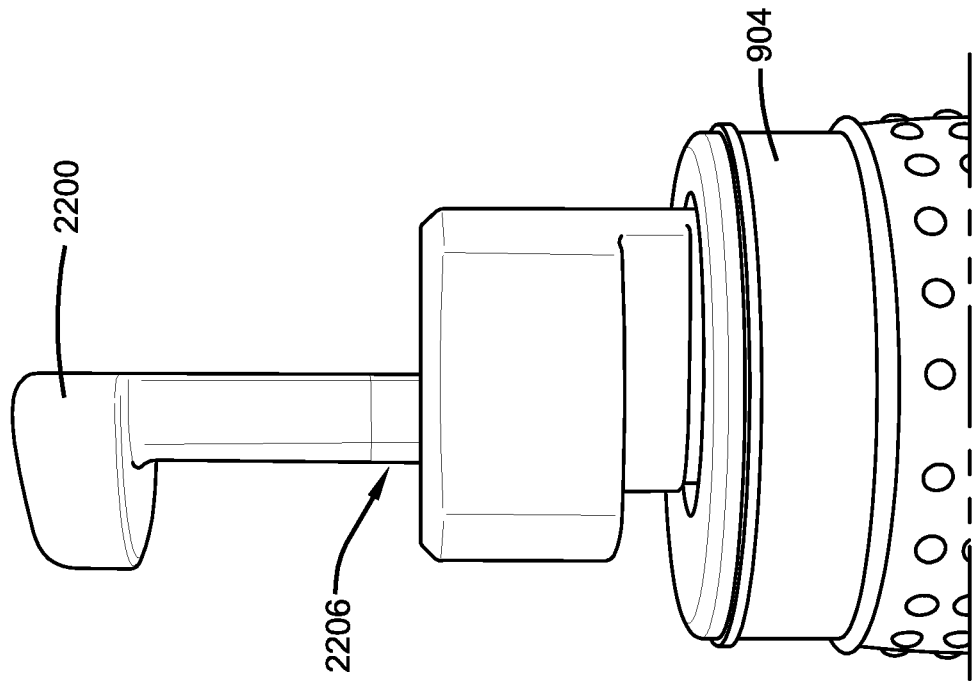
FIG. 68 is a side view of the proximal end of an inserter showing the impactor positioned within the inserter.
Figure 67:
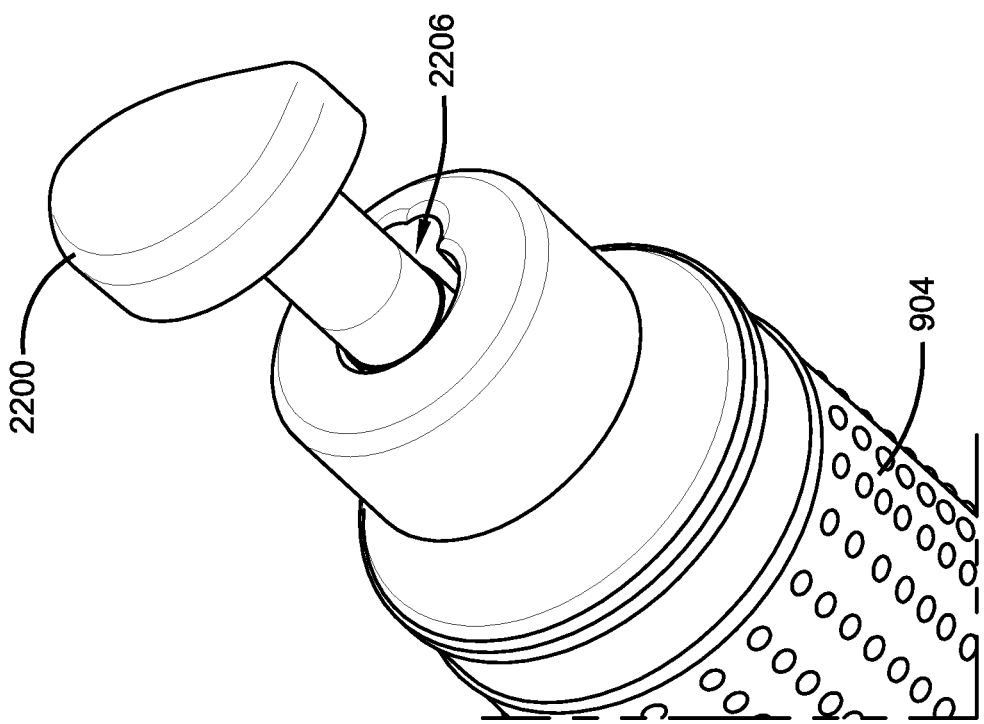
FIG. 67 is a perspective view of the proximal end of an inserter showing the impactor positioned within the inserter.
Figure 69:
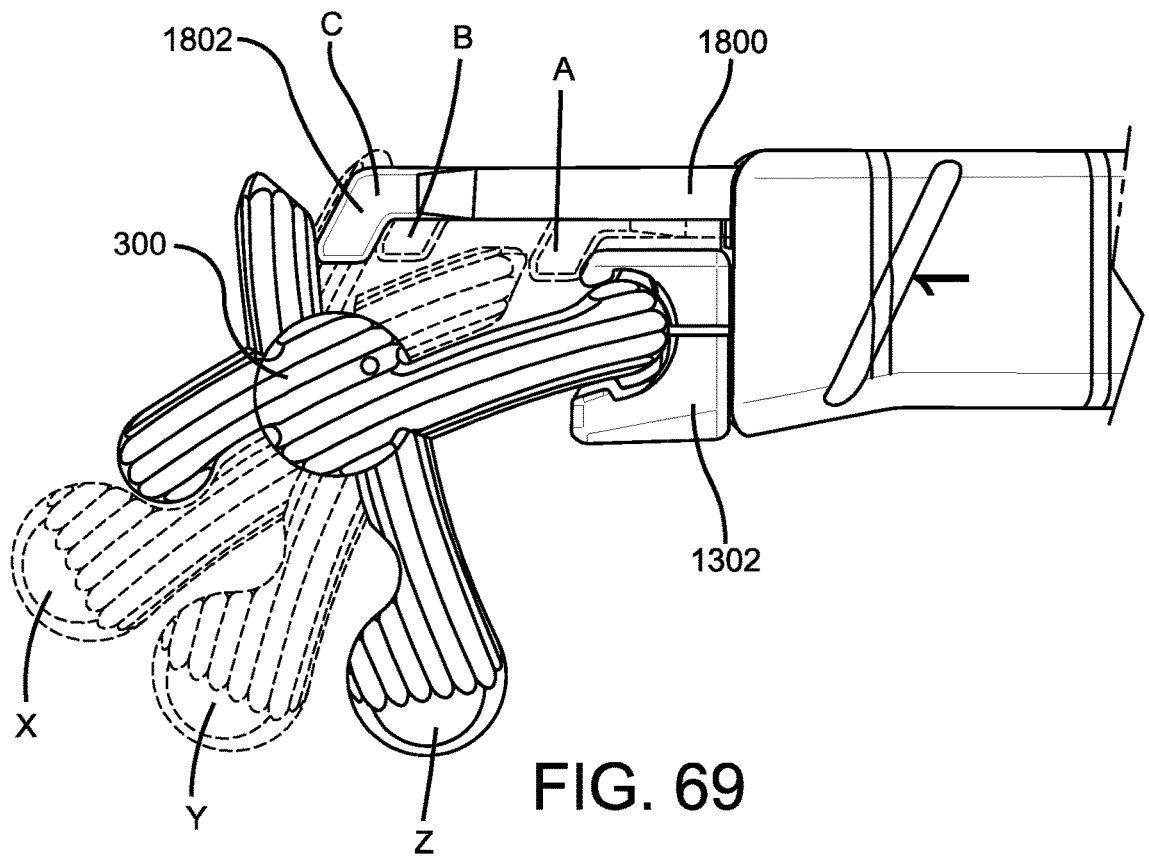
FIG. 69 is a top view of a gripper gripping a spinal implant and an inserter tamp being moved to deploy the spinal implant.
Figure 70:
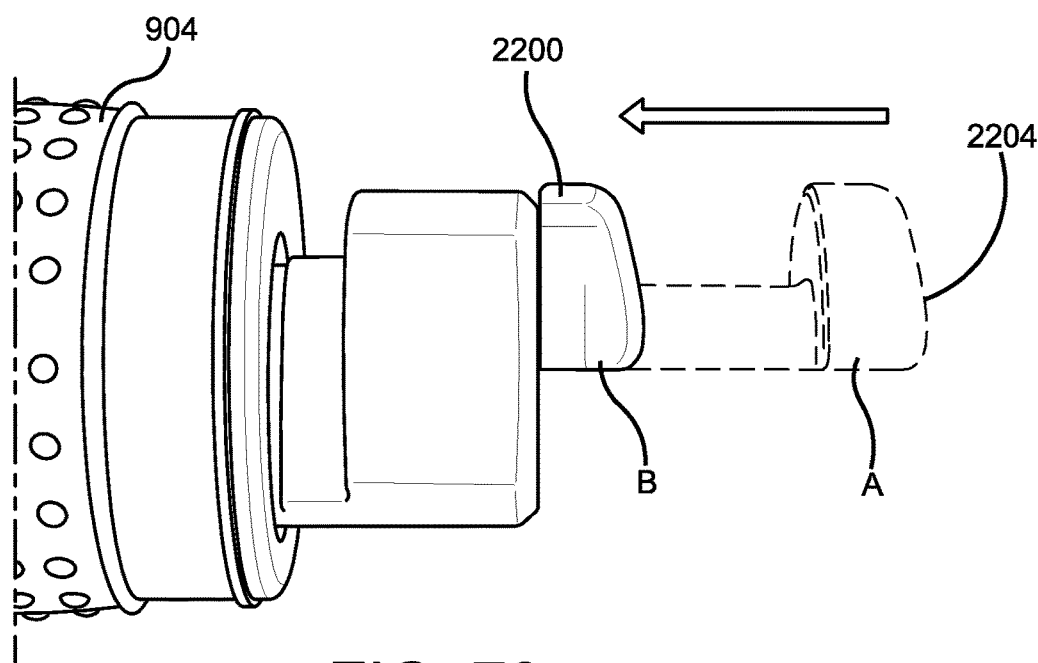
FIG. 70 is a side view of the proximal end of an inserter showing the impactor being moved to deploy the spinal implant.
Figure 71:
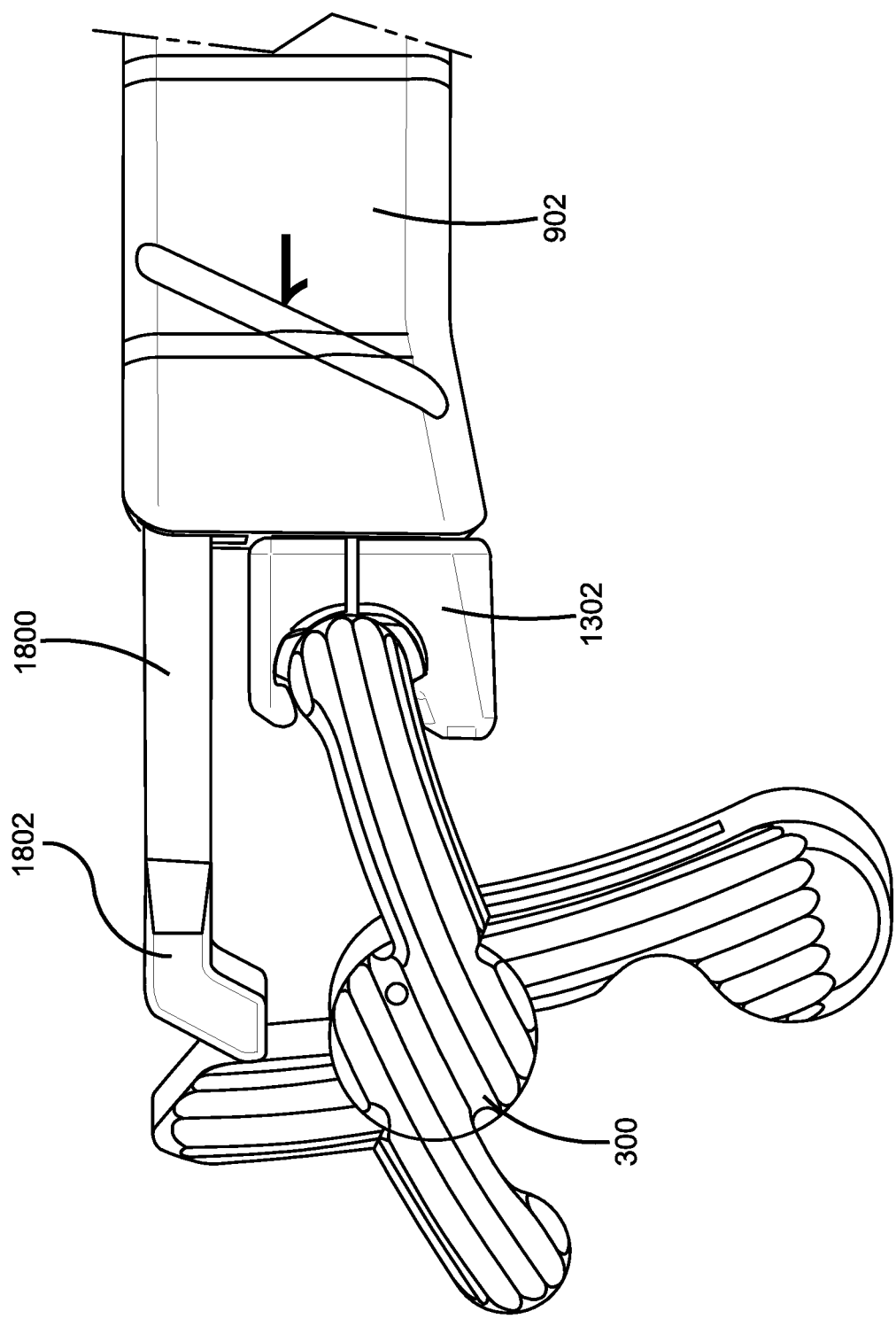
FIG. 71 is a top view of a gripper gripping a spinal implant and an inserter tamp extended to deploy the spinal implant.

With reference now to FIGS. 26, 33, 46-50 and 67-71, once the correct impactor has been selected, the surgeon may insert the distal end of the impactor 2200 into the proximal end of channel 920. The surgeon may push the impactor 2200 into the inserter 900 until marking 2206 is positioned at the proximal end of the inserter 900 as shown in FIGS. 67 and 68. In this condition, the contact surface 2202 of the impactor 2200 may contact the proximal end of the inserter tamp 1800 within channel 920. To adjust the tamp 1800 to deploy the implant 300, the surgeon may then use a mallet or other device against contact surface 2204 to move the impactor 2200 within the inserter 900. Specifically, the impactor 2200 may be moved from position A to position B (FIG. 70). This movement causes the contact surface 2202 of the impactor 2200 (see FIG. 50) to apply a force to the inserter tamp 1800 causing it to move from position A to position B to position C (FIG. 69). This movement of the inserter tamp 1800 causes the implant 300 to deploy by moving in turn from position X to position Y to position Z, also shown in FIG. 69. This distal movement of the impactor 2200 also moves impactor tab 2212 into button groove 944 and button tab 942 into impactor groove 2210. In this way, the impactor 2200 is latched to the inserter 900. FIG. 71 also shows the implant 300 in the deployed condition. The surgeon may use fluoroscopy and the relative positions of pins 332, 350, as described above, to confirm that the implant 300 is locked into the deployed condition.

With reference now to FIGS. 26, 33, 55-56 and 72-73, with the implant 300 positioned and deployed within the vertebral space, the surgeon may then detach the inserter 900 from the implant 300. This may be accomplished by rotating the tool 1400 in a counterclockwise direction, as shown in FIG. 73. This rotation may cause the rotational force converter 930 to rotate in the same direction extending the gripping device 1300 distally further out of the inserter 900 which in turn may cause the slot 1306 to enlarge so that the gripper 1302 releases the implant 300 as illustrated in FIG. 72. The surgeon may then remove the inserter 900 from the vertebral space. If desired, the surgeon may then adjust the position of the implant 300 with the freehand tamp 2800 (FIGS. 55-56), gripping the handle 2804, as needed.

With reference now to FIGS. 26, 33, 35-37 and 73-75, the surgical instruments may be disassembled from the inserter 900. FIG. 74 illustrates how the impactor 2200 and the inserter tamp 1800 may be easily removed. First, the button 918 may be pressed inwardly (upwardly in FIG. 74) to overcome the biasing force of biasing device 926 and thus to open the latch mechanism 916. While holding the button 918 in the inward position, the impactor 2200 and the inserter tamp 1800 are no longer latched and thus can easily be pulled out of the inserter channel 920 in directions A and B, respectively. The button 918 can then be released. Note that latch mechanism 950, if used, does not prevent removal of these components. To remove the gripping device 1300, the tool 1400 may be rotated in the counterclockwise direction as shown in FIG. 73. This rotation may cause the rotational force converter 930 to rotate in the same direction extending the gripping device 1300 distally further out of the inserter 900 until the rotational force converter 930 releases (disengages) the gripping device 1300. The gripping device 1300 can then, as shown in FIG. 75, simply be pulled out of the inserter channel 922 in direction C.

Figure 76:
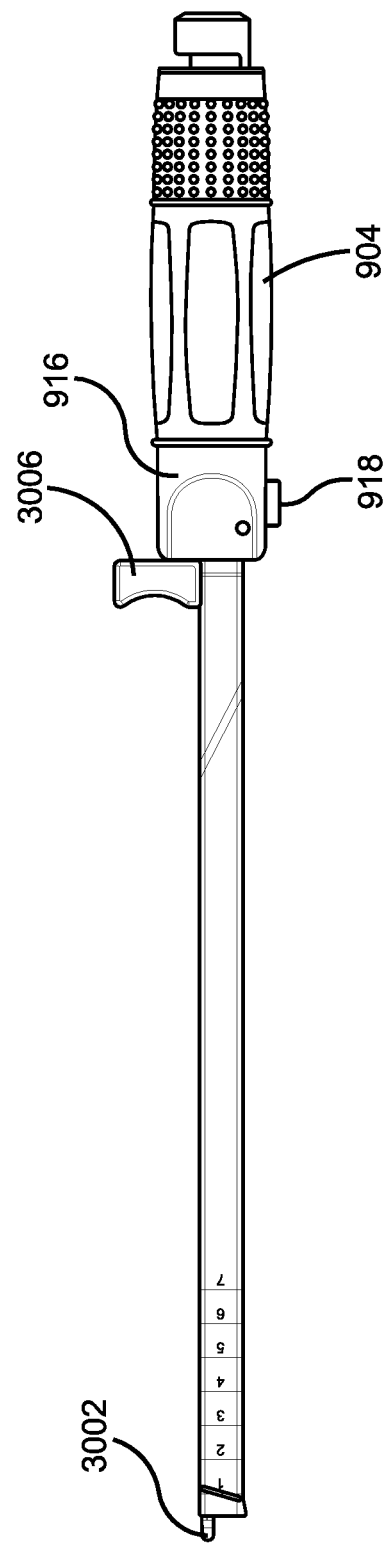
FIG. 76 is a side view showing a remover tamp being inserted into an inserter.
Figure 77:
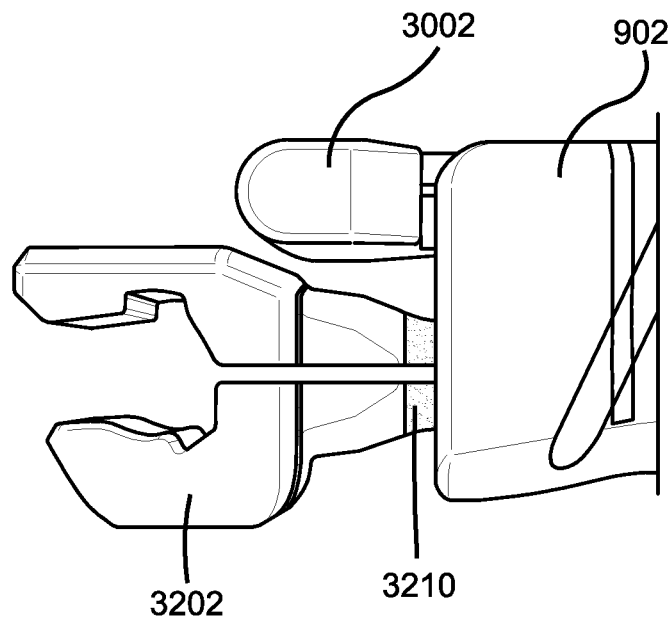
FIG. 77 is a close-up side view of the distal end of an inserter showing a remover tamp and gripping device.
Figure 78:
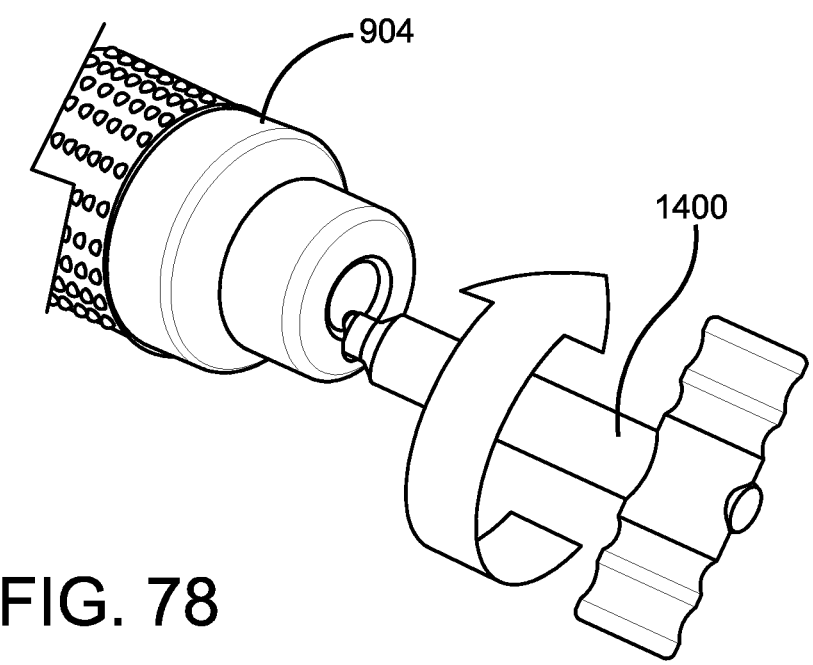
FIG. 78 is a perspective view of the proximal end of an inserter showing a tool being rotated to close a gripping device.
Figure 79:
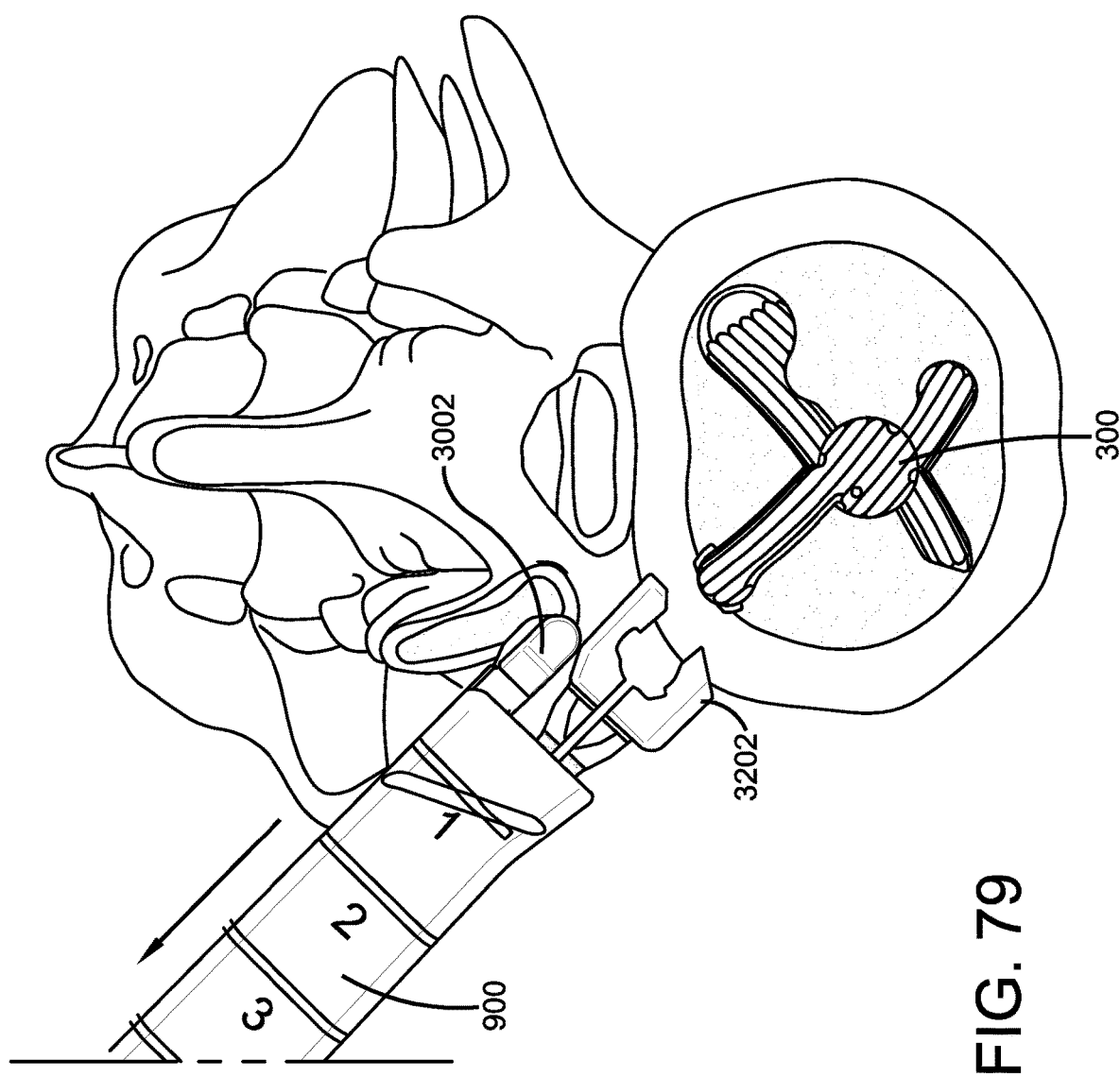
FIG. 79 illustrates a remover tamp and gripping device being positioned to engage a deployed spinal implant within a vertebral space.
Figure 80:
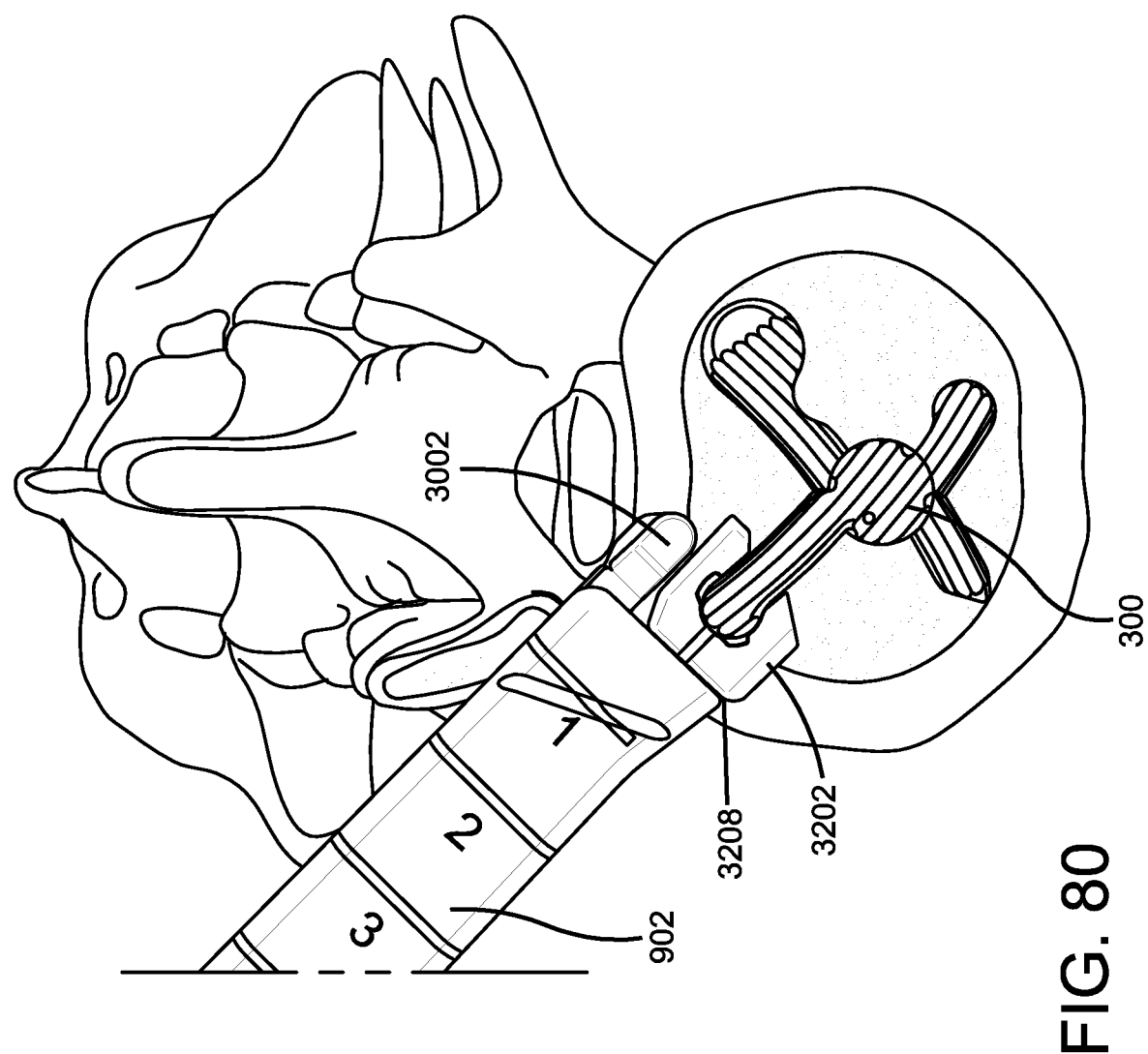
FIG. 80 illustrates a gripping device gripping a deployed spinal implant within a vertebral space.

With reference now to FIGS. 26, 33, 51-54, 76-80, in some cases, it may be necessary to remove the implant 300 from the vertebral space. In this case, the appropriate remover tamp 3000 may be attached to the inserter 900 in the same manner as inserter tamp 1800, described above. The result is shown in FIG. 76 with the trigger 3006 contacting a distal surface of the proximal end portion 904 of the inserter 900. Gripping device 3200 may be attached to the inserter in the same manner as gripping device 1300, described above. In this way, tool 1400 may be rotated in clockwise direction as indicated in FIG. 78 drawing gripping device 1300 to the position shown in FIG. 77. The inserter 900 may then be inserted into the vertebral space, as illustrated in FIG. 79, until the grip mechanism 3202 is positioned around an outer surface of the implant 300. The tool 1400 may then be rotated further in the clockwise direction, as shown in FIG. 78, until the marking 3208 is flush with the distal end of the inserter as illustrated in FIG. 80. This indicates that the grip mechanism 3202 has a tight grip on the implant 300.

With reference now to FIGS. 19-20, 26, 33, 46-54 and 81-83, impactor 2200 may be used, as disclosed above and illustrated in FIG. 82. The surgeon may use a mallet or other device against contact surface 2204 to move impactor 2200 from position A to position B. This motion may cause the contact surface 2202 of the impactor 2200 (see FIG. 50) to apply additional force to the remover tamp 3000 causing it to extend from position A to position B as shown in FIG. 81.

Figure 83:
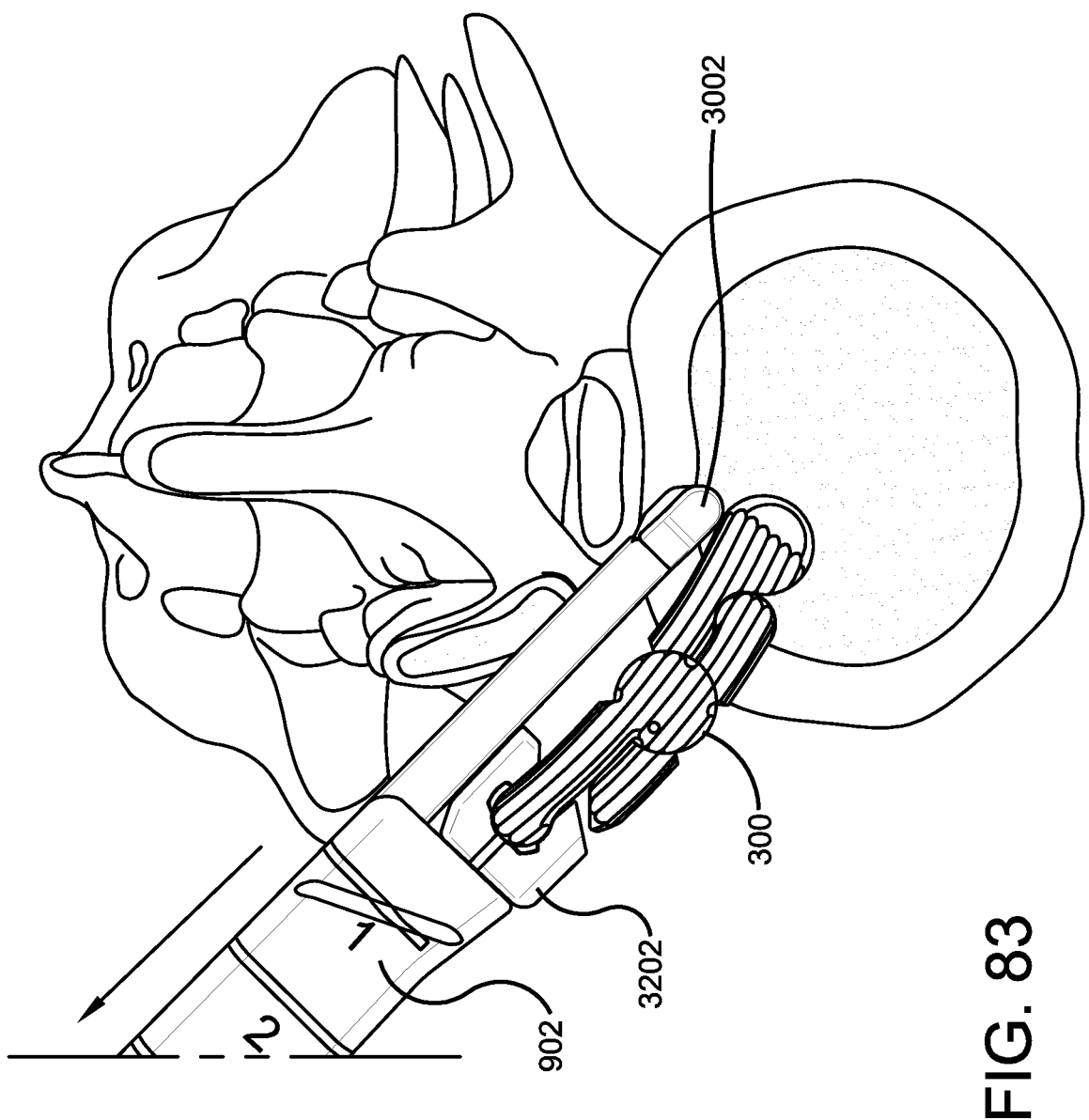
FIG. 83 illustrates a collapsed implant being removed from a vertebral space.

This extension of the tamp 3000 causes the implant 300 to adjust from the deployed condition to the collapsed condition as indicated in FIG. 81. This collapsing of the implant 300 may cause pin 332 to separate as shown in FIGS. 19-20 and described above. The surgeon may use fluoroscopy and the relative positions of pins 332 (now in the form of pin portions 344 and 346) and 350, as described above, to confirm that the implant 300 is unlocked and in the collapsed condition. With the implant 300 now maintained in the collapsed condition, it can then be removed from the vertebral space as shown in FIG. 83. The impactor 2200, remover tamp 3000 and gripping device 3200 may be removed from the inserter 900 in the same way as the previously described impactor, inserter tamp and gripping device.

In the patent claims that follow, it should be understood that any component referred to as being "associated" is not being claimed positively but rather indicates the environment in which the claimed invention is used. Thus, for two non-limiting examples, if a patent claim includes "surgical instrumentation for use with an associated vertebral space" or "surgical instrumentation for use with an associated spinal implant" then Applicant's intent is that infringement does not require a vertebral space or a spinal implant. Rather, infringement only requires the surgical instrumentation used with a vertebral space or spinal implant.

Having thus described the invention, it is now claimed:

We claim:

1. Surgical instrumentation for use with (1) an associated vertebral space comprising a first vertebral body having a first endplate; and, a second vertebral body adjacent the first vertebral body having a second endplate; and, (2) an associated spinal implant having first and second contact surfaces designed to contact the first and second endplates, respectively; a first member; and, a second member that is movable with respect to the first member to deploy the spinal implant; the surgical instrumentation comprising:
    an inserter comprising: a proximal end; a distal end; a longitudinal length; a first longitudinally extending channel that extends for at least most of the longitudinal length; and, a second distinct longitudinally extending channel that extends for at least most of the longitudinal length;
    an implant gripping mechanism comprising: (1) a gripping device having: a proximal end; a distal end; and, a gripper positioned at the distal end of the gripping device; and, (2) a tool; and,
    an implant deployment mechanism comprising: (1) an inserter tamp having: a proximal end; and, a distal end; and, (2) an impactor;
    wherein the implant gripping mechanism is operable to: (1) position at least a portion of the gripping device within the first longitudinally extending channel; and, (2) access the proximal end of the gripping device through the proximal end of the first longitudinally extending channel with the tool to adjust the gripper to grip the associated spinal implant with the spinal implant juxtaposed to the distal end of the first longitudinally extending channel; and,
    wherein the implant deployment mechanism is operable to: (1) position at least a portion of the inserter tamp within the second longitudinally extending channel; and, (2) access the proximal end of the inserter tamp through the proximal end of the second longitudinally extending channel with the impactor to adjust the distal end of the inserter tamp to deploy the associated spinal implant while the gripper grips the associated spinal implant within the associated vertebral space.

2. The surgical instrumentation of claim 1 wherein:
    the inserter further comprises a latch mechanism comprising a biasing force generator that receives the proximal end of the inserter tamp; and,
    the latch mechanism must be manually adjusted before the inserter tamp can be adjusted to deploy the associated spinal implant.

3. The surgical instrumentation of claim 1 wherein:
    the impactor has a proximal end and a distal end;
    the inserter further comprises a latch mechanism comprising a biasing force generator that receives the proximal end of the inserter tamp and the distal end of the impactor; and,
    the latch mechanism must be manually adjusted before the inserter tamp and impactor can be removed from the inserter.

4. The surgical instrumentation of claim 1 wherein:
    the impactor has a proximal end and a distal end; and,
    the distal end of the impactor contacts the proximal end of the inserter tamp to deploy the associated spinal implant.

5. The surgical instrumentation of claim 1 wherein the inserter tamp is manually adjustable into:
    a first position where the distal end of the inserter tamp prevents the associated spinal implant from deploying; and,
    a second position where the distal end of the inserter tamp deploys the associated spinal implant.

6. The surgical instrumentation of claim 5 wherein the inserter tamp is manually adjustable into:
    a third position where the distal end of the inserter tamp does not prevent the associated spinal implant from deploying and does not deploy the associated spinal implant.

7. The surgical instrumentation of claim 1 wherein the inserter tamp comprises a trigger that extends laterally outside the inserter and is used to manually position the inserter tamp within the second longitudinally extending channel.

8. The surgical instrumentation of claim 1 further comprising:
    a remover tamp having: a proximal end; and, a distal end; and,
    wherein the implant deployment mechanism is operable to: (1) remove the inserter tamp from the inserter; (2) position at least a portion of the remover tamp within the second longitudinally extending channel; and, (3) access the proximal end of the remover tamp through the proximal end of the second longitudinally extending channel with the impactor to adjust the distal end of the remover tamp to collapse the associated spinal implant while the gripper grips the associated spinal implant within the associated vertebral space.

9. The surgical instrumentation of claim 1 further comprising:
    a rotational force converter that: has a proximal end; has a distal end; and, is positioned within the first longitudinally extending channel; and,
    wherein the proximal end of the rotational force converter receives the tool and the distal end of the rotational force converter receives the proximal end of the gripping device.

10. The surgical instrumentation of claim 1 wherein the gripping device is longitudinally adjustable with respect to the inserter into:

a first relative position where the gripper does not grip the associated spinal implant; and, a second relative position where the gripper does grip the associated spinal implant.

11. A method for use with an associated vertebral space comprising a first vertebral body having a first endplate and a second vertebral body adjacent the first vertebral body having a second endplate; the method comprising the steps of:
(A) providing a spinal implant having first and second contact surfaces designed to contact the first and second endplates, respectively; a first member; and, a second member that is movable with respect to the first member to deploy the spinal implant;
(B) providing surgical instrumentation comprising:
    (1) an inserter comprising: a proximal end; a distal end; a longitudinal length; a first longitudinally extending channel that extends for at least most of the longitudinal length; and, a second distinct longitudinally extending channel that extends for at least most of the longitudinal length;
    (2) an implant gripping mechanism comprising: (a) a gripping device having: a proximal end; a distal end; and, a gripper positioned at the distal end of the gripping device; and, (b) a tool; and,
    (3) an implant deployment mechanism comprising: (a) an inserter tamp having: a proximal end; and, a distal end; and, (b) an impactor;
(C) providing the surgical instrumentation to be operable to:
    (1) position at least a portion of the gripping device within the first longitudinally extending channel;
    (2) access the proximal end of the gripping device through the proximal end of the first longitudinally extending channel with the tool to adjust the gripper to grip the spinal implant with the spinal implant juxtaposed to the distal end of the first longitudinally extending channel;
    (3) position at least a portion of the inserter tamp within the second longitudinally extending channel; and,
    (4) access the proximal end of the inserter tamp through the proximal end of the second longitudinally extending channel with the impactor to adjust the distal end of the inserter tamp to deploy the spinal implant while the gripper grips the spinal implant within the associated vertebral space.

12. The method of claim 11 wherein:
step (B)(1) comprises the step of: providing the inserter with a latch mechanism comprising a biasing force generator;
step (C)(3) comprises the step of: engaging the proximal end of the inserter tamp to the latch mechanism; and,
providing the surgical instrumentation to require manual adjustment of the latch mechanism before the inserter tamp can be adjusted to deploy the associated spinal implant.

13. The method of claim 11 wherein:
step (B)(1) comprises the step of: providing the inserter with a latch mechanism comprising a biasing force generator;
step (B)(3)(b) comprises the step of: providing the impactor with a proximal end and a distal end;
step (C)(3) comprises the step of: engaging the proximal end of the inserter tamp to the latch mechanism;
step (C)(4) comprises the step of: engaging the distal end of the impactor to the latch mechanism; and,
providing the surgical instrumentation to require manual adjustment of the latch mechanism before the inserter tamp and impactor can be removed from the inserter.

14. The method of claim 11 wherein step (C) comprises the step of providing the inserter tamp to be manually adjustable into:
a first position where the distal end of the inserter tamp prevents the spinal implant from deploying; and,
a second position where the distal end of the inserter tamp deploys the spinal implant.

15. The method of claim 14 wherein step (C) comprises the step of providing the inserter tamp to be manually adjustable into:
a third position where the distal end of the inserter tamp does not prevent the spinal implant from deploying and does not deploy the associated spinal implant.

16. The method of claim 11 wherein:
step (B)(1) comprises the step of: providing the inserter with a longitudinally extending groove that provides an opening to the second longitudinally extending channel;
step (B)(3) comprises the step of: providing the inserter tamp with a trigger;
step (C)(3) comprises the step of: positioning the inserter tamp using the trigger extended out of the groove.

17. The method of claim 11 wherein:
step (B) comprises the step of: providing a remover tamp having a proximal end and a distal end; and,
step (C) comprises the steps of:
    removing the inserter tamp from the inserter;
    positioning at least a portion of the remover tamp within the second longitudinally extending channel; and,
    accessing the proximal end of the remover tamp through the proximal end of the second longitudinally extending channel with the impactor to adjust the distal end of the remover tamp to collapse the spinal implant while the gripper grips the associated spinal implant within the associated vertebral space.

18. The method of claim 11 wherein:
step (B)(1) comprises the step of: providing the inserter with a rotational force converter that: has a proximal end; has a distal end; and, is positioned within the first longitudinally extending channel;
step (C)(1) comprises the step of: engaging the proximal end of the gripping device to the distal end of the rotational force converter; and,
step (C)(2) comprises the step of: engaging the tool to the proximal end of the rotational force converter.

19. The method of claim 11 wherein step (C) comprises the step of providing the gripping device to be longitudinally adjustable with respect to the inserter into:
a first relative position where the gripper does not grip the spinal implant; and,
a second relative position where the gripper does grip the spinal implant.

20. The method of claim 11 wherein:
step (A) comprises the steps of:
    providing the first member with a first opening;
    providing the second member to be pivotal with respect to the first member about a pivot axis defining axial directions;
    providing the spinal implant with a first pin that is: fluoroscopically detectable as distinct from the first and second members; supported to the second member; and, biased via a biasing force in an axial direction;

providing a second pin that is: fluoroscopically detectable as distinct from the first and second members; and, supported to one of the first member and the second member;

step (C) comprises the step of: providing the spinal implant to be operable by pivoting the first member with respect to the second member about the pivot axis when positioned within the associated vertebral space between:

a non-deployed condition where:
(a) the first vertebral body endplate contact surface faces the first vertebral body and has a first effective footprint area;
(b) the second vertebral body endplate contact surface faces the second vertebral body;
(c) the first pin is prevented from entering the first opening;
(d) the first member is pivotal with respect to the second member about the pivot axis; and,
(e) fluoroscopic imaging indicates a first relative axial position between the first and second pins;

a deployed condition where:
(a) the first vertebral body endplate contact surface faces the first vertebral body and has a second effective footprint area that is larger than the first effective footprint area;
(b) the second vertebral body endplate contact surface faces the second vertebral body;
(c) the biasing force positions the first pin at least partially within the first opening;
(d) the first pin locks the first member to the second member preventing the first member from pivoting with respect to the second member about the pivot axis; and,
(e) fluoroscopic imaging indicates a second relative axial position between the first and second pins that is different from the first relative axial position between the first and second pins.

* * * * *